United States Patent
Ahmad et al.

(10) Patent No.: US 9,586,900 B2
(45) Date of Patent: Mar. 7, 2017

(54) PYRROLONE OR PYRROLIDINONE MELANIN CONCENTRATING HORMONE RECEPTOR-1 ANTAGONISTS

(71) Applicant: BRISTOL-MYERS SQUIBB COMPANY, Princeton, NJ (US)

(72) Inventors: Saleem Ahmad, Wall, NJ (US); Guohua Zhao, Princeton, NJ (US); William N. Washburn, Titusville, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 5 days.

(21) Appl. No.: 14/425,507

(22) PCT Filed: Sep. 3, 2013

(86) PCT No.: PCT/US2013/057766
§ 371 (c)(1),
(2) Date: Mar. 3, 2015

(87) PCT Pub. No.: WO2014/039411
PCT Pub. Date: Mar. 13, 2014

(65) Prior Publication Data
US 2015/0218093 A1    Aug. 6, 2015

Related U.S. Application Data

(60) Provisional application No. 61/696,983, filed on Sep. 5, 2012.

(51) Int. Cl.
| | | |
|---|---|---|
| C07D 207/273 | (2006.01) |
| C07D 207/327 | (2006.01) |
| C07D 401/12 | (2006.01) |
| C07D 409/12 | (2006.01) |
| A61K 31/4015 | (2006.01) |
| A61K 31/4025 | (2006.01) |
| A61K 31/4439 | (2006.01) |
| C07D 403/12 | (2006.01) |
| C07D 207/27 | (2006.01) |

(52) U.S. Cl.
CPC ...... *C07D 207/273* (2013.01); *C07D 207/27* (2013.01); *C07D 207/327* (2013.01); *C07D 401/12* (2013.01); *C07D 403/12* (2013.01); *C07D 409/12* (2013.01)

(58) Field of Classification Search
CPC .............. C07D 207/273; C07D 401/12; C07D 409/12; C07D 207/327; A61K 31/4015; A61K 31/4025; A61K 31/4439
USPC ...... 548/518, 544, 519; 544/141; 546/278.7; 514/423, 425, 429, 422
See application file for complete search history.

(56) References Cited

U.S. PATENT DOCUMENTS

| | | | |
|---|---|---|---|
| 3,674,836 A | 7/1972 | Creger |
| 4,027,009 A | 5/1977 | Grier et al. |
| 4,379,785 A | 4/1983 | Weyer et al. |
| 4,639,436 A | 1/1987 | Junge et al. |
| 4,759,923 A | 7/1988 | Buntin et al. |
| 4,904,769 A | 2/1990 | Rauenbusch |
| 5,447,954 A | 9/1995 | Gribble et al. |
| 5,488,064 A | 1/1996 | Sher |
| 5,491,134 A | 2/1996 | Sher et al. |
| 5,541,204 A | 7/1996 | Sher et al. |
| 5,594,016 A | 1/1997 | Ueno et al. |
| 5,612,359 A | 3/1997 | Murugesan |
| 5,698,527 A | 12/1997 | Kim |
| 5,770,615 A | 6/1998 | Cheng et al. |
| 5,776,983 A | 7/1998 | Washburn et al. |
| 6,043,265 A | 3/2000 | Murugesan et al. |
| 6,414,002 B1 | 7/2002 | Cheng et al. |
| 6,414,126 B1 | 7/2002 | Ellsworth et al. |

FOREIGN PATENT DOCUMENTS

| | | |
|---|---|---|
| DE | 196 22 222 A1 | 12/1997 |
| EP | 0 818 448 A1 | 1/1998 |
| EP | 0 675 714 B1 | 1/1999 |
| EP | 0 992 496 A1 | 4/2000 |
| EP | 1 022 272 A1 | 7/2000 |

(Continued)

OTHER PUBLICATIONS

STN Registry Database entry for CAS RN 1346843-67-1, Published in database on Dec. 1, 2011.*
Borowsky, B. et al., "Antidepressant, anxiolytic and anorectic effects of a melanin-concentrating hormone-1 receptor antagonist", Nature Medicine, vol. 8, No. 8, pp. 825-830 (2002) and vol. 8, No. 9, p. 639 (2002) (corrigenda).
Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).

(Continued)

*Primary Examiner* — Alicia L Otton
*Assistant Examiner* — Sagar Patel
(74) *Attorney, Agent, or Firm* — Barry H. Jacobsen; Yong Lu

(57) ABSTRACT

The present invention provides compounds of Formula (I): as defined in the specification and compositions comprising any of such novel compounds. These compounds are melanin concentrating hormone receptor-1 (MCHR1) antagonists which may be used as medicaments.

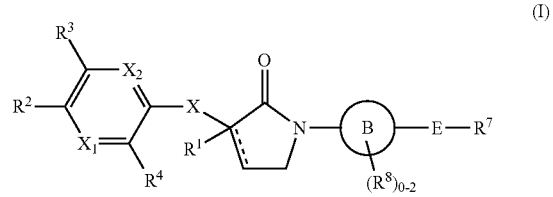

10 Claims, No Drawings

(56) References Cited

FOREIGN PATENT DOCUMENTS

| GB | 2 304 106 A | 3/1997 |
|---|---|---|
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/39077 | 7/2000 |
| WO | WO 00/50574 | 8/2000 |
| WO | WO 2004/047755 | 6/2004 |
| WO | WO 2004/110994 | 12/2004 |
| WO | WO 2005/072740 | 8/2005 |
| WO | WO 2006/019020 | 2/2006 |
| WO | WO 2006/044775 | 4/2006 |
| WO | WO 2006/082010 | 8/2006 |
| WO | WO 2006/134317 | 12/2006 |
| WO | WO 2010/104818 | 9/2010 |

OTHER PUBLICATIONS

Bundgaard, H., ed., Design of Prodrugs, Elsevier Science Publishers B.V., publ. (1985).

Bundgaard, H., "Prodrugs as a means to improve the delivery of peptide drugs", Advanced Drug Delivery Reviews, vol. 8, pp. 1-38 (1992).

Gehlert, D.R. et al., "Preclinical Evaluation of Melanin-Concentrating Hormone Receptor 1 Antagonism for the Treatment of Obesity and Depression", The Journal of Pharmacology and Experimental Therapeutics, vol. 329, No. 2, pp. 429-438 (2009).

Gennaro, A.R., ed., Remington's Pharmaceutical Sciences, 18th Edition, pp. xv-xvi, Mack Publishing Company, publ. (1990).

Greene, T.W. et al., Protective Groups in Organic Synthesis, Second Edition, pp. ix-x, John Wiley & Sons, Inc., publ. (1991).

Greene, T.W. et al., Protective Groups in Organic Synthesis, Third Edition, pp. xi-xii, John Wiley & Sons, Inc., publ. (1999).

Hara, S., "Ileal $Na^+$/bile acid cotransporter inhibitors", Drugs of the Future, vol. 24, No. 4, pp. 425-430 (1999).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Kokkotou, E. et al., "Melanin-concentrating hormone as a mediator of intestinal inflammation", Proc. Natl. Acad. Sci., vol. 105, No. 30, pp. 10613-10618 (2008).

Kowalski, T.J. et al., "Melanin-concentrating hormone-1 receptor antagonism decreases feeding by reducing meal size", European Journal of Pharmacology, vol. 497, pp. 41-47 (2004).

Larock, R.C., Comprehensive Organic Transformations: A Guide to Functional Group Preparations, pp. xiii-xxviii, VCH Publishers, Inc., publ. (1989).

Lewis, Sr., R.J., Hawley's Condensed Chemical Dictionary, Thirteenth Edition, John Wiley & Sons, Inc., publ. (1997).

Ljung, B. et al., "AZ 242, a novel PPARα/β agonist with beneficial effects on insulin resistance and carbohydrate and lipid metabolism in ob/ob mice and obese Zucker rats", Journal of Lipid Research, vol. 43, pp. 1855-1863 (2002).

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", Journal of Medicinal Chemistry, vol. 41, No. 6, pp. 973-980 (1998).

Salisbury, B.G., "Hypocholesterolemic activity of a novel inhibitor of cholesterol absorption, SCH 48461", Atherosclerosis, vol. 115, pp. 45-63 (1995).

Semmelhack, M.F., ed., Comprehensive Organic Synthesis: Selectivity, Strategy & Efficiency in Modern Organic Chemistry, vol. 4: "Additions to and Substitutions at C—C π-Bonds", pp. v-vi, Pergamon Press, Inc., publ. (1991).

Takekawa, S. et al., "T-226296: a novel, orally active and selective melanin-concentrating hormone receptor antagonist", European Journal of Pharmacology, vol. 438, pp. 129-135 (2002).

Testa, B. et al., Hydrolysis in Drug and Prodrug Metabolism: Chemistry, Biochemistry, and Enzymology, pp. xi-xx, Wiley-VCH GmbH & Co., publ. (2003).

Widder, K.J. et al., eds., Section III: "Prodrugs", Methods in Enzymology, vol. 112, pp. 309-396, Academic Press, Inc., publ. (1985).

Yajima, K. et al., "Combination therapy with PPARγ and PPARα agonists increases glucose-stimulated insulin secretion in db/db mice", Am. J. Physiol. Endocrinol. Metab., vol. 284, pp. E966-E971 (2003) and vol. 285, p. E926 (2003) (corrigenda).

* cited by examiner

PYRROLONE OR PYRROLIDINONE MELANIN CONCENTRATING HORMONE RECEPTOR-1 ANTAGONISTS

The present application is a 371 of International Application No. PCT/US2013/057766 filed on Sep. 3, 2013, which claims priority benefit of US, provisional application Ser. No.: 61/696,983, filed Sep. 5, 2012; each of which is fully incorporated by reference herein.

FIELD OF THE INVENTION

The present invention relates to novel pyrrolone or pyrrolidinone melanin concentrating hormone receptor-1 (MCHR1) antagonists, pharmaceutical compositions, processes of preparing, and therapeutic and prophylactic uses thereof. Diseases treated and/or prevented include obesity, diabetes and related diseases ameliorated by antagonizing MCHR1 receptor.

BACKGROUND OF THE INVENTION

Several lines of pharmacological and genetic evidence support the role of melanin concentrating hormone receptor-1 (hereafter "MCHR1") as a modulator of food intake and body weight. Central administration of melanin concentrating hormone (MCH) increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; Takekawa, S. et al., *Eur. J. Pharmacol.*, 438:129-135 (2002); Borowsky, B. et al., *Nat. Med.*, 8:825-830 (2002); Kowalski, T. J. et al., *Eur. J. Pharmacol.*, 497:41-47 (2004).

MCHR1 has also been reported to play a key role in the pathogenesis of acute experimental colitis and possibly human IBD (inflammatory bowel disease). It has been shown that immunoneutralization is an effective treatment for TNBS-induced colitis. Kokkotou, E. et al., "Melanin-concentrating hormone as a mediator of intestinal inflammation", *PNAS*, 105(30):10613-10618 (2008).

In addition, MCH and MCHR1 have also been reported to play a role in the endocrine and behavioral responses to stress. Treatment of rats and mice with MCHR antagonists produces a robust anti-depressant and anti-anxiolytic effect. (Gehlert, D. R. et al., *JPET*, 329(2):429-438 (2009))

Non-peptide MCHR1 antagonists have been disclosed, but none of the MCHR1 publications disclosed pyrrolone or pyrrolidinone containing compounds as described in the present invention. In accordance with the present invention, there is provided a series of novel pyrrolone or pyrrolidinone MCHR1 antagonists.

SUMMARY OF THE INVENTION

The present invention provides pyrrolone or pyrrolidinone compounds, and their analogues thereof, which are useful as MCHR1 antagonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with MCHR1 antagonists, such as obesity, diabetes, anxiety or depression.

The compounds of the invention may be used in therapy.

The compounds of the invention may be used for the manufacture of a medicament for the treatment and/or prophylaxis of multiple diseases or disorders associated with MCHR1.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

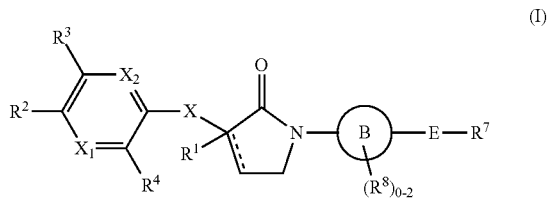

(I)

or a stereoisomer, a tautomer, a pharmaceutically acceptable salt, or a solvate thereof, wherein:

═══ is independently a single or double bond; provided that when ═══ is a single bond, $R^1$ is H or $C_{1-4}$ alkyl; and when ═══ is a double bond $R^1$ is absent;

X is independently O or S;

$X_1$ is independently N or $CR^5$;

$X_2$ is independently N or $CR^6$;

ring B is independently $C_{3-6}$ carbocycle or a 5- to 10-membered heterocycle containing carbon atoms and 1-4 heteroatoms selected from the group consisting of N, $NR^e$, O, and $S(O)_p$;

E is independently O or S;

$R^2$, at each occurrence, is independently at selected from: H, halogen, OH, CN, $NO_2$, $C_{1-6}$ alkyl, $C_{1-6}$ alkoxy, $C_{1-6}$ alkylthio, $C_{1-6}$ haloalkyl, $C_{1-6}$ haloalkoxy, $C_{1-6}$ haloalkylthio, $R^9$, and —O—$R^9$;

$R^3$, $R^4$, $R^5$ and $R^6$, at each occurrence, are independently selected from: H, halogen, OH, CN, $NO_2$, $C_{1-6}$ alkyl, $C_{1-6}$ alkoxy, $C_{1-6}$ alkylthio, $C_{1-6}$ haloalkyl, $C_{1-6}$ haloalkoxy, and $C_{1-6}$ haloalkylthio;

R[7] is independently selected from: H, $C_{1-8}$ alkyl substituted with 0-3 R[a], $C_{1-6}$ alkoxy substituted with 0-3 R[a], —(CH$_2$)$_m$—R[10], —(CH$_2$)$_m$—CHR[10]R[11], —(CH$_2$)$_n$—OCHR[10]R[11], and

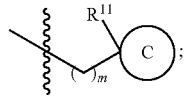

ring C is independently a $C_{3-7}$ carbocycle or 3- to 6-membered heterocycle containing carbon atoms and 1-2 heteroatoms selected from the group consisting of O, and $S(O)_p$; wherein said carbocycle and heterocycle are each substituted with 0-3 R[c];

R[8], at each occurrence, is independently selected from: H, $C_{1-6}$ alkyl, $C_{1-6}$ alkoxy, halogen, $C_{1-6}$ alkylthio, $C_{1-6}$ haloalkyl, $C_{1-6}$ haloalkoxy, $C_{1-6}$ haloalkylthio, CN, $C_{3-6}$ cycloalkyl, and —O—$C_{3-6}$ cycloalkyl;

R[9], at each occurrence, is independently a $C_{3-6}$ carbocycle or a 3- to 6-membered heterocycle containing carbon atoms and 1-4 heteroatoms selected from the group consisting of N, NR[e], O, and $S(O)_p$; wherein said carbocycle and heterocycle are each substituted with 0-3 R[b];

R[10], at each occurrence, is independently a $C_{3-7}$ carbocycle or a 3- to 6-membered heterocycle containing carbon atoms and 1-2 heteroatoms selected from the group consisting of O, and $S(O)_p$; wherein said carbocycle and heterocycle are each substituted with 0-3 R[c];

R[11], at each occurrence, is independently H or OR[d];

R[a], at each occurrence, is independently selected from: halogen, OR[d], CH$_2$OR[d], CN, $C_{1-4}$ alkyl, $C_{1-4}$ alkoxy, $C_{1-4}$ haloalkyl, $C_{3-6}$ cycloalkyl, —O—$C_{3-6}$ cycloalkyl, C(O)$C_{1-4}$ alkyl, CO$_2$H, CO$_2C_{1-4}$ alkyl, SO($C_{1-4}$ alkyl), and SO$_2$($C_{1-4}$ alkyl);

R[b], at each occurrence, is independently selected from: halogen, OH, CN, $C_{1-4}$ alkyl, $C_{1-4}$ alkoxy, $C_{1-4}$ haloalkyl, $C_{1-4}$ haloalkoxy, $C_{3-6}$ cycloalkyl, and —O—$C_{3-6}$ cycloalkyl;

R[c], at each occurrence, is independently selected from: halogen, OR[d], CH$_2$OR[d], CN, $C_{1-4}$ alkyl, $C_{1-4}$ alkoxy, and $C_{1-4}$ haloalkyl;

R[d], at each occurrence, is independently selected from: H, C(O)$C_{1-4}$ alkyl, C(O)(Ph), C(O)CH$_2$NH$_2$, —C(O)CH($C_{1-4}$ alkyl)NH$_2$, —C(O)CH$_2$CO$_2$H, —C(O)(CH$_2$)$_2$CO$_2$H, and P(O)(OH)$_2$;

R[e], at each occurrence, is independently H or $C_{1-4}$ alkyl;

m, at each occurrence, is independently 0, 1, 2, or 3;

n, at each occurrence, is independently 1, 2, or 3; and p, at each occurrence, is independently 0, 1 or 2.

In a second aspect, the present invention includes compounds of Formula (I), or a stereoisomer, a tautomer, a pharmaceutically acceptable salt, or a solvate thereof, within the scope of the first aspect wherein:

=== is independently a single or double bond; provided that when === is a single bond, R[1] is H or $C_{1-2}$ alkyl; and when === is a double bond R[1] is absent;

$X_1$ is independently N or CR[5];

$X_2$ is independently N or CR[6];

provided that $X_1$ and $X_2$ are not both N;

ring B is independently phenylene or pyridylene;

R[2], at each occurrence, is independently at selected from: $C_{1-6}$ alkyl, $C_{1-6}$ alkoxy, $C_{1-6}$ alkylthio, $C_{1-6}$ haloalkyl, $C_{1-6}$ haloalkoxy, $C_{1-6}$ haloalkylthio, R[9], and —O—R[9];

R[3], R[4], R[5] and R[6], at each occurrence, are independently selected from: H, halogen, OH, CN, $C_{1-4}$ alkyl, $C_{1-4}$ alkoxy, $C_{1-2}$ haloalkyl, and $C_{1-2}$ haloalkoxy;

R[7] is independently selected from H, $C_{1-6}$ alkyl substituted with 0-3 R[a], $C_{1-6}$ alkoxy substituted with 0-3 R[a], —(CH$_2$)$_m$—R[10], —(CH$_2$)$_m$—CHR[10]R[11], —(CH$_2$)$_n$—OCHR[10]R[11],

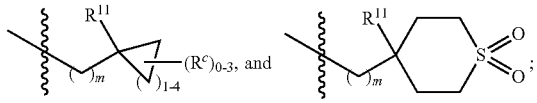

R[10], at each occurrence, is independently selected from a $C_{3-6}$ cycloalkyl, phenyl or a 3- to 6-membered heterocycle containing carbon atoms and 1-2 heteroatoms selected from the group consisting of O, and $S(O)_p$; wherein said $C_{3-6}$ cycloalkyl, phenyl and heterocycle are each substituted with 0-3 R[c];

R[11], at each occurrence, is independently H or OR[d];

m, at each occurrence, is independently 0, 1 or 2; and n, at each occurrence, is independently 1, or 2.

In another aspect, the present invention includes compounds of Formula (I), or a stereoisomer, a tautomer, a pharmaceutically acceptable salt, or a solvate thereof, within the scope of the first or second aspect wherein: X is O.

In another aspect, the present invention includes compounds of Formula (I), or a stereoisomer, a tautomer, a pharmaceutically acceptable salt, or a solvate thereof, within the scope of the first or second aspect wherein: E is O.

In a third aspect, the present invention includes compounds of Formula (II):

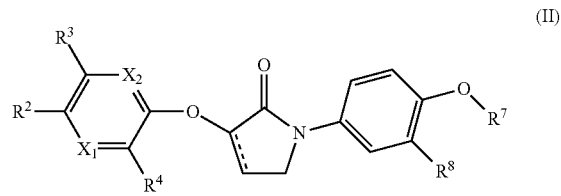

or a stereoisomer, a tautomer, a pharmaceutically acceptable salt, or a solvate thereof, wherein:

=== is a single or double bond;

$X_1$ is independently N or CR[5];

$X_2$ is independently N or CR[6];

provided that $X_1$ and $X_2$ are not both N;

R[2], at each occurrence, is independently at selected from: H, halogen, CF$_3$, CH$_2$CF$_3$, OCF$_3$, $C_{1-4}$ alkoxy, cyclopropyl, cyclopropyloxy, phenyl, 2-$C_{1-4}$ alkyl-phenyl, 2-$C_{1-4}$ alkoxy-phenyl, 2-halo-phenyl, 3-halo-phenyl, 4-halo-phenyl, 2-CF$_3$-phenyl, azetidin-1-yl, pyrrol-1-yl, imidazol-1-yl, morpholin-1-yl, pyrid-3-yl, pyrid-4-yl, and 3-halo-pyrid-4-yl.

R[3], R[4], R[5] and R[6], at each occurrence, are independently selected from: H, halogen, $C_{1-4}$ alkyl, $C_{1-4}$ alkoxy, $C_{1-2}$ haloalkyl, and $C_{1-2}$ haloalkoxy;

R[7] is independently selected from: H, $C_{1-4}$ alkyl, —CH$_2$C($C_{1-2}$ alkyl)$_2$OH, —CH$_2$C($C_{1-2}$ alkyl)(CH$_2$OH)OH, —CH$_2$CH$_2$SO($C_{1-2}$ alkyl), —CH$_2$CH$_2$SO$_2$($C_{1-2}$ alkyl), —CH$_2$CH(OH)CH$_2$SO$_2$($C_{1-2}$ alkyl), —CH$_2$CH$_2$SO$_2$(CH$_2$C($C_{1-2}$ alkyl)$_2$OH), —CH$_2$C($C_{1-2}$ alkyl)$_2$OC(O)CH$_2$NH$_2$, —CH$_2$C($C_{1-2}$ alkyl)$_2$OP(O)(OH)$_2$,

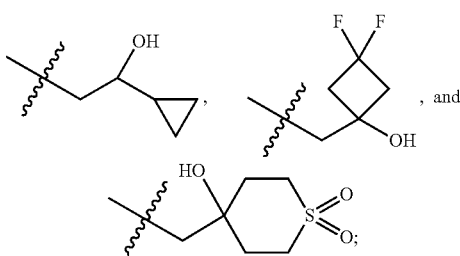

and

R[8] is independently $C_{1-4}$ alkyl substituted with 0-1 halogen or $C_{1-4}$ alkoxy with 0-1 halogen.

In a fourth aspect, the present invention includes a compound of Formula (IIa):

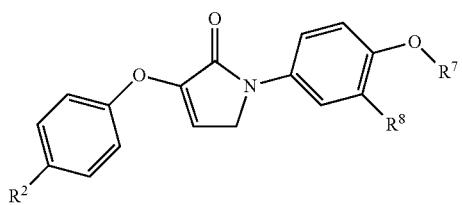

or a stereoisomer, a tautomer, a pharmaceutically acceptable salt, or a solvate thereof, wherein:

R[2] is independently selected from $OCF_3$, cyclopropyl, and phenyl;

R[7] is independently selected from H, —$CH_2C(C_{1-2}$ alkyl$)_2OH$, —$CH_2C(C_{1-2}$ alkyl$)(CH_2OH)OH$, —$CH_2C(C_{1-2}$ alkyl$)_2OC(O)CH_2NH_2$, —$CH_2C(C_{1-2}$ alkyl$)_2OP(O)(OH)_2$, and

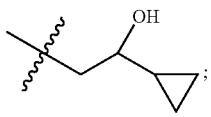 [SMILES: *CC(O)C1CC1]

R[8] is independently $C_{1-4}$ alkyl or $C_{1-4}$ alkoxy.

In a fifth aspect, the present invention includes a compound of Formula (IIa) or a stereoisomer, a tautomer, a pharmaceutically acceptable salt, or a solvate thereof, within the scope of the fourth aspect wherein:

R[2] is independently selected from: $OCF_3$, cyclopropyl, and phenyl;

R[7] is independently selected from: H, —$CH_2C(Me)_2OH$, —$CH_2C(Me)(CH_2OH)OH$, —$CH_2C(Me)_2OC(O)CH_2NH_2$, —$CH_2C(Me)_2OP(O)(OH)_2$, and

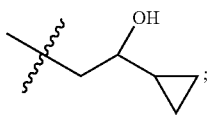 [SMILES: *CC(O)C1CC1]

and

R[8] is independently Me or OMe.

In a sixth aspect, the present invention includes a compound of Formula (IIa) or a stereoisomer, a tautomer, a pharmaceutically acceptable salt, or a solvate thereof, within the scope of the fourth or fifth aspects wherein:

R[2], R[7], and R[8] are selected in concert from:

| R[2] | R[7] | R[8] |
|---|---|---|
| $OCF_3$ | —$CH_2C(Me)_2OH$ | OMe |
| $OCF_3$ | —$CH_2C(Me)_2OC(O)CH_2NH_2$ | OMe |
| cyclopropyl | —$CH_2C(Me)_2OH$ | OMe |
| cyclopropyl | —$CH_2C(Me)_2OC(O)CH_2NH_2$ | OMe |
| cyclopropyl | —$CH_2C(Me)_2OP(O)(OH)_2$ | OMe |
| $OCF_3$ | —$CH_2C(Me)_2OH$ | Me |
| cyclopropyl | —$CH_2C(Me)_2OH$ | Me |
| cyclopropyl | —$CH_2C(Me)(CH_2OH)OH$ | OMe |
| cyclopropyl | H | OMe |
| cyclopropyl | 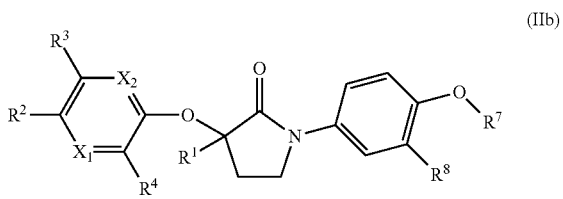 | OMe |
| cyclopropyl | (pyrrolidin-3-yl group) | OMe |
| phenyl | —$CH_2C(Me)_2OH$ | OMe |

In a seventh aspect, the present invention includes a compound of Formula (IIb), (IIb)

[structure shown]

or a stereoisomer, a tautomer, a pharmaceutically acceptable salt, or a solvate thereof, wherein:

$X_1$ is independently N or $CR^5$;

$X_2$ is independently N or $CR^6$;

provided that $X_1$ and $X_2$ are not both N;

R[1] is independently H or $C_{1-2}$ alkyl;

R[2], at each occurrence, is independently selected from: halogen, $CF_3$, $CH_2CF_3$, $OCF_3$, $C_{1-4}$ alkoxy, cyclopropyl, cyclopropyloxy, phenyl, 2-$C_{1-4}$ alkyl-phenyl, 2-$C_{1-4}$ alkoxy-phenyl, 2-halo-phenyl, 3-halo-phenyl, 4-halo-phenyl, 2-$CF_3$-phenyl, azetidin-1-yl, pyrrol-1-yl, imidazol-1-yl, morpholin-1-yl, pyrid-3-yl, pyrid-4-yl, and 3-halo-pyrid-4-yl.

R[3], R[4], R[5] and R[6], at each occurrence, are independently selected from H, halogen, $C_{1-4}$ alkyl, $C_{1-4}$ alkoxy, and $C_{1-2}$ haloalkyl;

R[7] is independently selected from —$CH_2C(C_{1-2}$ alkyl$)_2OH$, —$CH_2CH_2SO(C_{1-2}$ alkyl), —$CH_2CH_2SO_2(C_{1-2}$ alkyl), —$CH_2CH(OH)CH_2SO_2(C_{1-2}$ alkyl), —$CH_2CH_2SO_2(CH_2C(C_{1-2}$ alkyl$)_2OH)$, —$CH_2C(C_{1-2}$ alkyl$)_2OC(O)CH_2NH_2$,

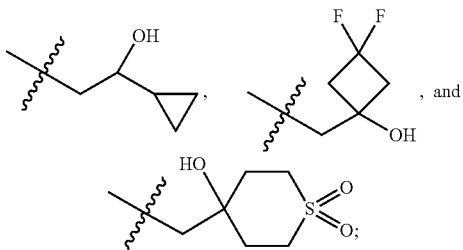

and $R^8$ is independently selected from: $C_{1-4}$ alkyl, $C_{1-4}$ alkoxy and —$OCH_2CH_2F$.

In an eighth aspect, the present invention includes a compound of Formula (IIIb) or a stereoisomer, a tautomer, a pharmaceutically acceptable salt, or a solvate thereof, within the scope of the seventh aspect wherein:

$R^1$ is independently at selected from the group consisting of H and Me;

$R^2$, at each occurrence, is independently selected from: OMe, Cl, I, $CF_3$, $CH_2CF_3$, $OCF_3$, cyclopropyl, cyclopropyloxy, phenyl, 2-Me-phenyl, 2-F-phenyl, 3-F-phenyl, 4-F-phenyl, 2-Cl-phenyl, azetidin-1-yl, pyrrol-1-yl, pyrid-3-yl, and pyrid-4-yl;

$R^3$, $R^4$, $R^5$ and $R^6$, at each occurrence, are independently selected from: H, F, Cl, Me, OMe, $CF_3$, and $OCF_3$;

$R^7$ is independently selected from: —$CH_2C(Me)_2OH$, —$CH_2CH_2SO_2Me$, —$CH_2CH_2SOMe$, —$CH_2CH(OH)CH_2SO_2Me$, —$CH_2CH(OH)CH_2SO_2Et$, —$CH_2CH_2SO_2(CH_2C(Me)_2OH)$, —$CH_2C(Me)_2OC(O)CH_2NH_2$,

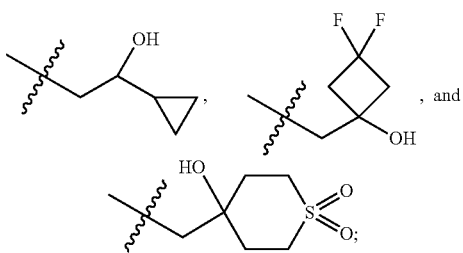

and $R^8$ is independently selected from: Me, OMe and —$OCH_2CH_2F$.

In another aspect, the present invention includes compounds of Formula (I), or a stereoisomer, a tautomer, a pharmaceutically acceptable salt, or a solvate thereof, within the scope of the seventh or eighth aspect wherein:

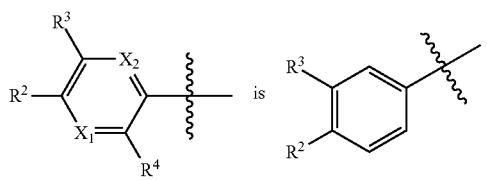

In another aspect, the present invention includes compounds of Formula (I), or a stereoisomer, a tautomer, a pharmaceutically acceptable salt, or a solvate thereof, within the scope of the seventh or eighth aspect wherein:

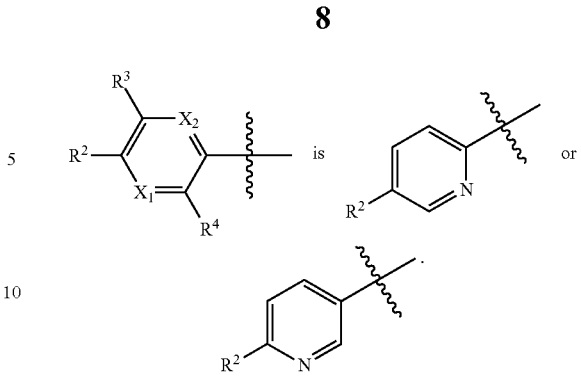

In another aspect, the present invention includes compounds of Formula (I), or a stereoisomer, a tautomer, a pharmaceutically acceptable salt, or a solvate thereof, within the scope of the seventh or eighth aspect wherein:

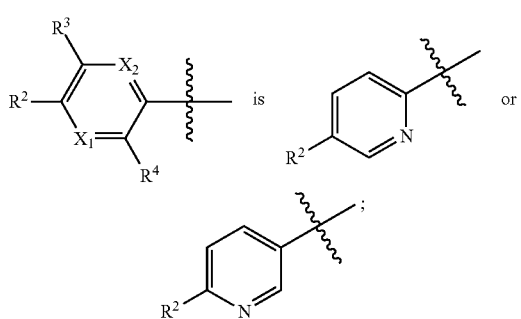

wherein $R^2$, at each occurrence, is independently phenyl.

In a ninth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the ninth aspect.

In another embodiment, the compounds of the present invention have hMCHR1 Ki values≤10 μM, preferably, Ki values≤5 μM, more preferably, Ki values≤1 μM, even more preferably, Ki values≤0.5 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example a member selected from saxagliptin, sitagliptin, vildagliptin and alogliptin).

In another embodiment, the present invention provides a method for the treatment and/or prophylaxis of multiple diseases or disorders associated with MCHR1, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the MCHR1 that can be prevented, modulated, or treated according to the present invention include, but are not limited to, metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; psychiatric disorders, such as depression, anxiety, schizophrenia, substance abuse, cognition-enhancement and Parkinson's disease; and inflammatory diseases such as inflammatory bowel disease, colitis and/or Crohn's disease.

In another embodiment, the present invention provides a method for the treatment and/or prophylaxis of obesity, diabetes, anxiety or depression, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of obesity or diabetes, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with MCHR1.

In another embodiment, the present invention also provides the use of a compound of the present invention for the manufacture of a medicament for the treatment and/or prophylaxis of multiple diseases or disorders associated with MCHR1.

In another embodiment, the present invention provides a method for the treatment and/or prophylaxis of multiple diseases or disorders associated with MCHR1, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with MCHR1.

Where desired, the compound of the present invention may be used in combination with one or more other types of therapeutic agents which may be administered orally in the same dosage form, in a separate oral dosage form or by injection. The other types of therapeutic agent that may be optionally employed in combination with the MCHR1 antagonist of the present invention may be one, two, three or more therapeutic agents which may be administered orally in the same dosage form, in a separate oral dosage form, or by injection to produce an additional pharmacological benefit.

Examples of other types of therapeutic agents include, e.g., anti-obesity agents; anti-diabetic agents, appetite suppressants; cholesterol/lipid-lowering agents, and high-density lipoprotein (HDL)-raising agents. Preferably, the anti-diabetic agent, for example, is dipeptidyl peptidase-IV (DPP4) inhibitor (for example a member selected from saxagliptin, sitagliptin, vildagliptin and alogliptin).

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, Inc. (1997). "$C_{6-10}$ aryl" refers to phenyl and naphthyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene et al., *Protective Groups in Organic Synthesis*, John Wiley & Sons, New York (1991) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrugs derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry*, Biochemistry and Enzymology, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "meq" for milliequivalent or milliequivalents, "g" for gram or grams, "mg" for milligram or milligrams, "L" for liter or liters, "mL" for milliliter or milliliters, "µL" for microliter or microliters, "N" for normal, "M" for molar, "mol" for mole or moles, "mmol" for millimole or millimoles, "min" for minute or min, "h" for hour or h, "rt" for room temperature, "$t_R$" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.
Me methyl
Et ethyl
Pr propyl
i-Pr isopropyl
Bu butyl
i-Bu isobutyl
t-Bu tert-butyl
Ph phenyl
Bn benzyl
Hex hexanes
Boc tert-butyloxycarbonyl
MeOH methanol
EtOH ethanol
i-PrOH or IPA isopropanol
KOH potassium hydroxide
NaOH sodium hydroxide
LiOH lithium hydroxide
n-BuLi n-butyllithium
CDCl$_3$ deutero-chloroform
CHCl$_3$ chloroform
CH$_2$Cl$_2$ dichloromethane
CH$_3$CN or ACN acetonitrile
cDNA complimentary DNA
CsF cesium fluoride
DCE dichloroethane
DEAD diethyl azodicarboxylate
DIAD diisopropyl azodicarboxylate
DIC 2-dimethylaminoisopropyl chloride HCl
DIPEA diisopropylethylamine
DMF dimethyl formamide
DMSO dimethyl sulfoxide
DMAP 4-dimethylaminopyridine
EDC 1-(3-dimethylaminopropyl)-3-ethylcarbodiimide HCl
EtOAc ethyl acetate
Et$_2$O diethyl ether
HCl hydrochloric acid
HOAc or AcOH acetic acid
H$_2$SO$_4$ sulfuric acid
H$_2$O$_2$ hydrogen peroxide
K$_2$CO$_3$ potassium carbonate
LHMDS lithium hexamethyldisilazide
mCPBA or m-CPBA meta-chloroperbenzoic acid
MgSO$_4$ magnesium sulfate
N$_2$ nitrogen
NaBH$_4$ sodium borohydride
NaH$_2$PO$_4$.H$_2$O sodium dihydrogen phosphate hydrate
NaCl sodium chloride
NaH sodium hydride
NaHCO$_3$ sodium bicarbonate
NaHSO$_3$ sodium bisulfite
Na$_2$SO$_3$ sodium sulfite
Na$_2$S$_2$O$_3$ sodium thiosulfate
Na$_2$SO$_4$ sodium sulfate
NEt$_3$ triethylamine
NH$_3$ ammonia
NH$_4$Cl ammonium chloride
NH$_4$OH ammonium hydroxide
NMO 4-methylmorpholine N-oxide
OsO$_4$ osmium tetroxide
Pd/C palladium on carbon
Pd(PPh$_3$)$_4$ palladium tetrakis(triphenylphosphine)
PPh$_3$ triphenylphosphine
SEM 2-(trimethylsilyl)ethoxymethyl
SEM-Cl 2-(trimethylsilyl)ethoxymethyl chloride
SiO$_2$ silica oxide
SOCl$_2$ thionyl chloride
TBAB tetrabutylammonium bromide
TBS tert-butyldimethylsilyl
TEA triethylamine
Tf triflate
TFA trifluoroacetic acid
THF tetrahydrofuran
LG leaving group
PG Protecting group The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula (I) falling into a given class may be compatible with some of the reaction conditions required in some of the methods described. Restrictions to the substituents that are compatible with the reaction conditions will be readily apparent to one skilled in the art and alternate methods must then be used.

Synthesis

The Compounds of Formula (I) may be prepared by the exemplary processes described in the following Schemes and working Examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Greene, T. W. et al., *Protecting Groups in Organic Synthesis*, 3rd Edition, Wiley (1999)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure*. 4th Edition, John Wiley & Sons, New York, N.Y. (1992); Katritzky, A. R. et al., eds., *Comprehensive Organic Functional Groups Transformations*, 1st Edition, Elsevier Science Inc., Tarrytown, N.Y. (1995); Larock, R. C., *Comprehensive Organic Transformations*, VCH Publishers, Inc., New York, N.Y. (1989), and references therein.

It will be understood that $R^7$ may be present in its final form throughout the synthesis or can be introduced at any point in the following synthetic sequences particularly if $R^7$ contains an hydroxyl. Specifically, $R^7$ may be carried along as a truncated moiety $R^{7'}$ such as E-H that may be protected as a SEM ether, SEM thioether, BOC amine or etc. and then elongated whenever appropriate. Likewise compounds of Formula I for which $R^7$ contains —CH$_2$CH$_2$SO(C$_{1-2}$ alkyl), —CH$_2$CH$_2$SO$_2$(C$_{1-2}$ alkyl), —CH$_2$CH(OH)CH$_2$SO$_2$(C$_{1-2}$ alkyl), or —CH$_2$CH$_2$SO$_2$(CH$_2$C(C$_{1-2}$ alkyl)$_2$OH) can be prepared by treatment of precursors containing —CH$_2$CH$_2$S(C$_{1-2}$ alkyl), —CH$_2$CH(OH)CH$_2$S(C$_{1-2}$ alkyl), or —CH$_2$CH$_2$S(CH$_2$C(C$_{1-2}$ alkyl)$_2$OH) with one or two equivalents respectively of an oxidant such as m-chloroperbenzoic acid in a solvent such as CH$_2$Cl$_2$.

Compounds of Formula (Ia) can be prepared as shown in Scheme 1. Substituted nitrobenzene intermediate A can be hydrogenated with Pd/C to give aniline B. The aniline B can be reacted with 2,4-dibromobutanoyl chloride and a base, e.g., NEt$_3$ followed by an additional base such as KOH with TBAB or AMBERLITE® IRA-400 and reacted with an alcohol C in a one pot reaction to give compounds of Formula (Ia).

Scheme 1

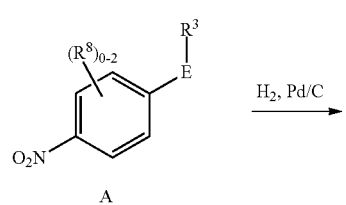

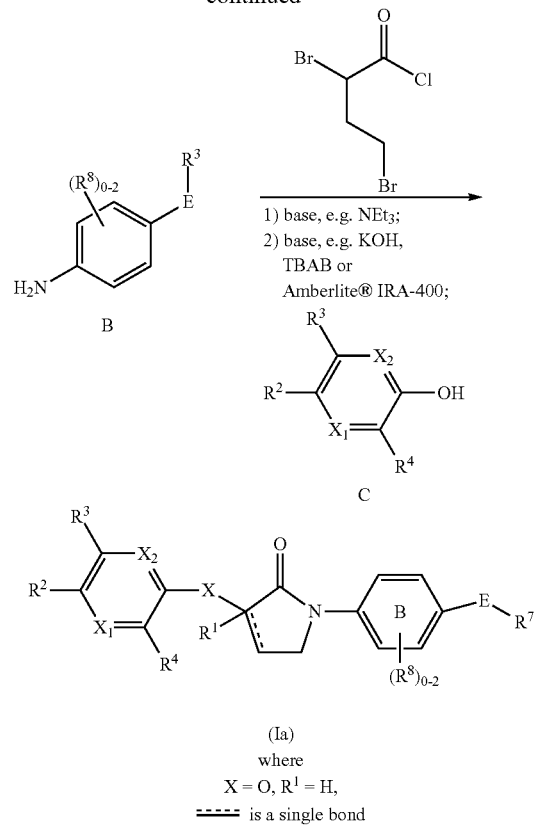

where
X = O, $R^1$ = H,
===== is a single bond

Alternatively, compounds of Formula (Ia) can be synthesized via reaction of aniline B with 2,4-dibromobutanoyl chloride and a base, e.g., NEt$_3$ followed by an additional base such as KOH with TBAB or AMBERLITE® IRA-400 to give bromopyrrolidinone D as demonstrated in Scheme 2. In a stepwise fashion, the bromide D can be displaced with an alcohol C using base, e.g., KOH and TBAB or AMBERLITE® IRA-400 to afford compounds of Formula (Ia).

Scheme 2

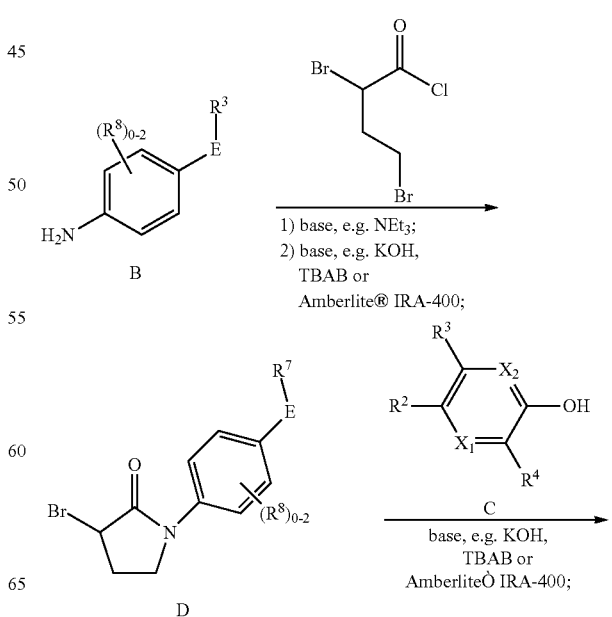

-continued

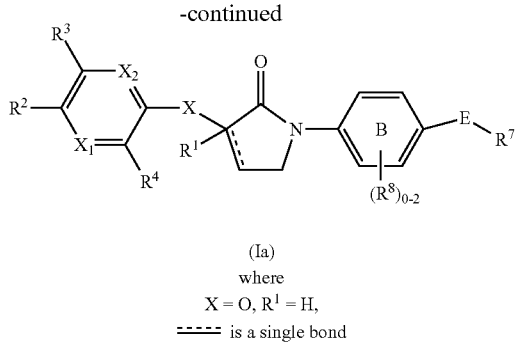

(Ia)
where
X = O, R¹ = H,
----- is a single bond

Compounds of Formula (Ia) can be synthesized from nitrobenzene E as demonstrated in Scheme 3. Hydrogenation with Pd/C provides aniline F. Aniline F can be reacted with an alcohol G containing a LG such as =F, Cl, Br, I, and the like following conditions described in Scheme 1 to give intermediate H. The coupling of boronic acid I with the LG in intermediate H gives compounds of Formula (Ia).

Scheme 3

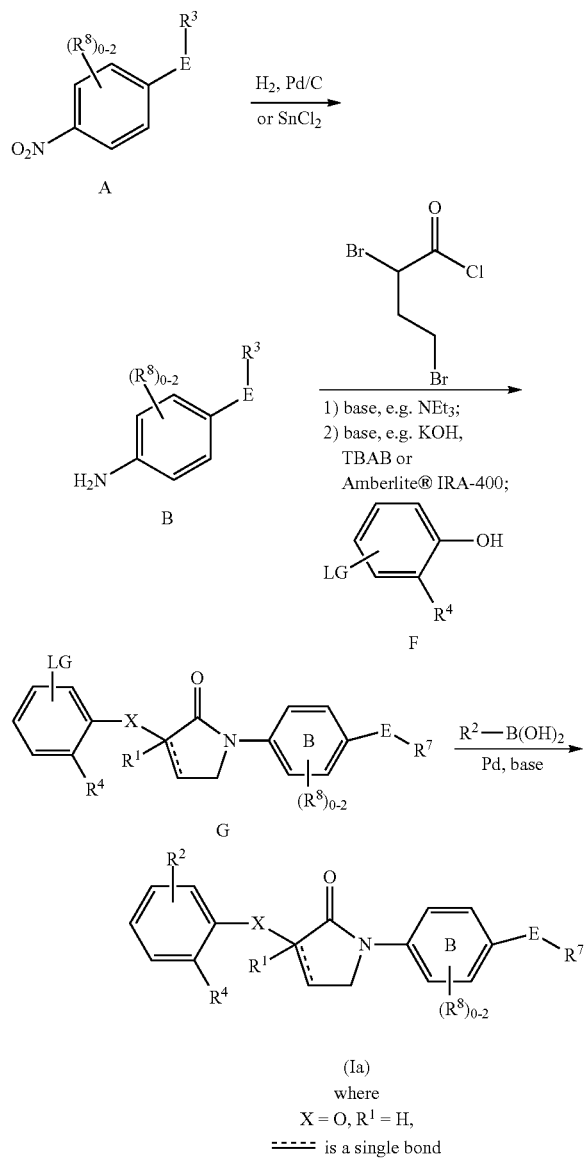

Compounds of Formula (Ia), prepared as described in Schemes 1 to 3, containing a saturated pyrrolidinone can be converted to the unsaturated pyrrolones as outlined in Scheme 4. Sequential treatment with a strong base such as lithium hexametyl disilazide followed by trapping with phenylselenyl generates selenides of formula J. Reaction of compounds of Formula J with $H_2O_2$ to form the corresponding thermally unstable selenoxides that eliminate in situ to generate the unsaturated pyrrolones of Formula (Ib).

Scheme 4

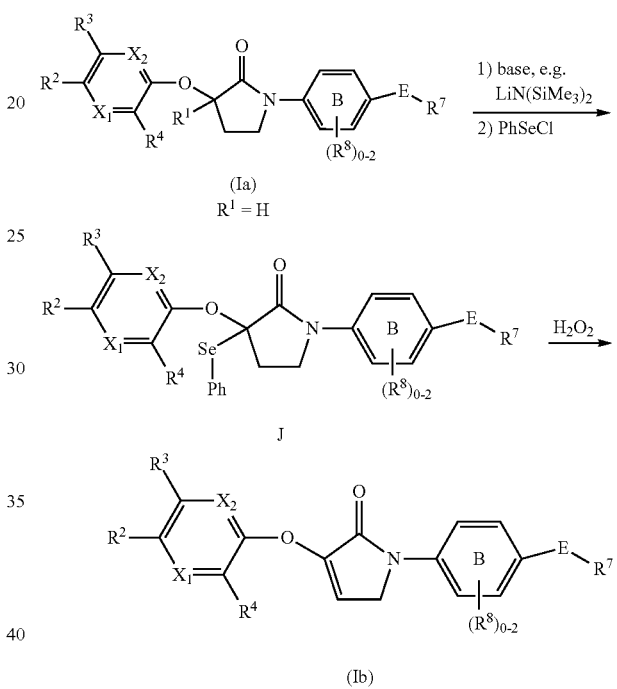

An alternative route for preparation of compounds of Formula (Ia) containing a pyrrolone core is outlined in Scheme 5. Compounds of Formula L can be prepared by a base promoted condensation of Compounds of Formula C with Compounds of Formula K. Compounds of Formula M can be prepared by reaction of Compounds of Formula K with Compounds of Formula B in the presence of a reagent such as EDC. Compounds of Formula N can be prepared following sequential treatment of Compounds of Formula M with a strong base such as NaH followed by allyl bromide. Conversion of Compounds of Formula N to Compounds of Formula Ia can be achieved by gentle heating in the presence of a Grubbs metathesis catalyst such as tricyclohexylphosphine[1,3-bis(2,4,6-trimethylphenyl)-4,5-dihydroimidazol-2-ylidene][benzylidine]ruthenium(IV)dichloride. Subsequently Compounds of Formula (Ia) can be prepared by hydrogenation of Compounds of Formula (Ib) in the presence of a catalyst such as Pd/C.

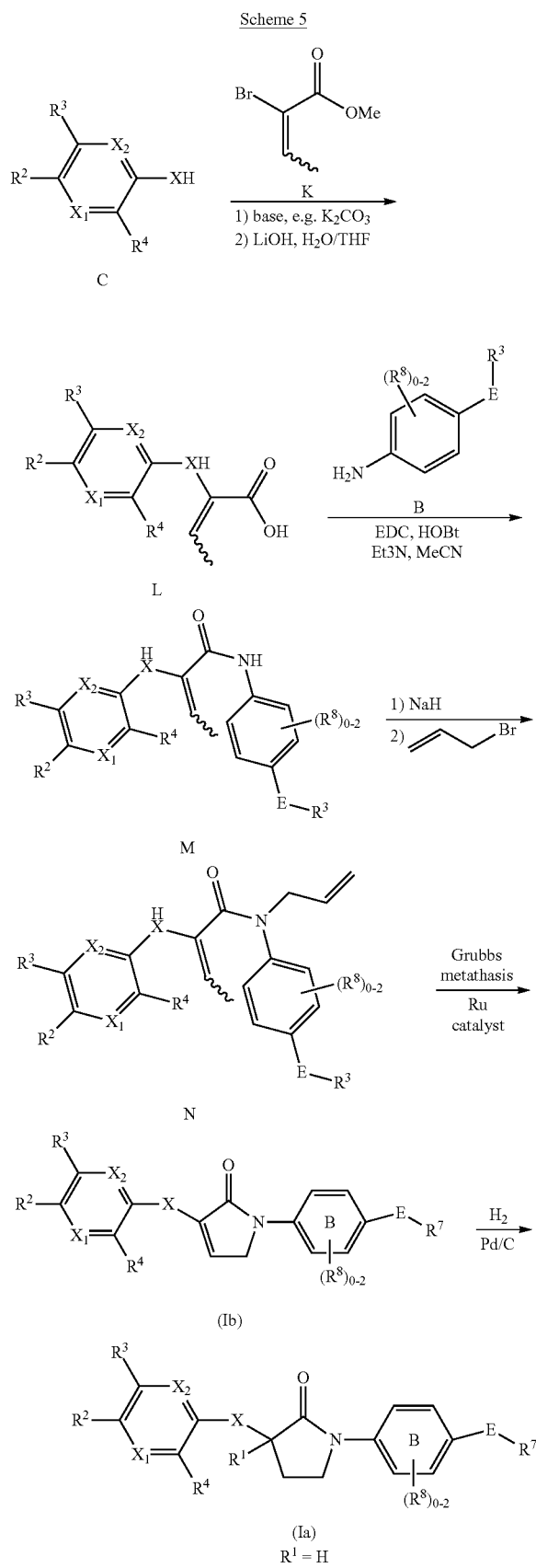

IV. Biological Assays and Evaluation

Radioligand Binding Assay for Assessment of MCHR1 Activity

An in vitro binding assay was used to determine the compound Ki value or ability to antagonize binding of a peptide agonist to the human melanin concentrating hormone receptor (MCHR1). Membranes from stably transfected HEK-293 cells expressing a mutated (E4Q, A5T) hMCHR1 receptor were prepared by dounce homogenization and differential centrifugation. Binding experiments were carried out with 0.5-1.0 μg of membrane protein incubated in a total of 0.2 mL in 25 mM HEPES (pH 7.4) with 10 mM $MgCl_2$, 2 mM EGTA, and 0.1% BSA (Binding Buffer) for 90 min. For competition binding assays, reactions were carried out in the presence of with 0.06-0.1 nM [$Phe^{13}$, [$^{125}I$]$Tyr^{19}$]-MCH and increasing concentrations of unlabeled test molecules. Reactions were terminated by rapid vacuum filtration over 96 well-GFC UNIFILTER® plates pre-coated with 0.075 mL binding buffer containing 1% BSA, and washed 3 times with 0.4 mL of Phosphobuffered Saline (pH 7.4) containing 0.01% TX-100. Filters were dried, 0.05 mL MicroScint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

The following representative in vitro biological data was measured in a binding assay for Compound Ia and the six Comparator Compounds above.

V. Utilities, Pharmaceutical Compositions and Combinations

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease; and inflammatory diseases such as inflammatory bowel disease, colitis and/or Crohn's disease.

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

According to one embodiment of the present invention, methods are provided for treating obesity in a patient in need of such treatment, comprising administering a therapeutically effective amount of at least Compound I (including a prodrug, a polymorph or a pharmaceutical acceptable salt) according to the present invention alone or in combination with one or more additional antiobesity agents, wherein the obesity agent is selected from those described herein.

According to one embodiment of the present invention, methods are provided for treating diabetes, especially Type II diabetes, in a patient in need of such treatment, comprising administering a therapeutically effective amount of at least Compound I (including a prodrug, a polymorph or a pharmaceutical acceptable salt), according to the present invention alone or in combination with one or more additional antidiabetic agents, wherein the diabetic agent is described herein.

According to one embodiment of the present invention, methods for treating depression and/or anxiety in a patient are provided, comprising administering a therapeutically effective amount of at least Compound I, or a prodrug, a polymorph or a pharmaceutical acceptable salt thereof, according to the present invention.

According to one embodiment of the present invention, methods are provided for treating inflammatory bowel disease, comprising administering a therapeutically effective amount of at least Compound I, or a prodrug, a polymorph or a pharmaceutical acceptable salt thereof.

According to some embodiments of the present invention, pharmaceutical compositions are provided, comprising at least Compound I, or a prodrug, a polymorph or a pharmaceutical acceptable salt thereof, as described herein, and at least one pharmaceutically acceptable diluent or carrier. The pharmaceutical compositions of the present invention may optionally include at least one additional therapeutic agent selected from the group consisting of anti-obesity agent, anti-diabetic agent, antidepressant agent, anti-anxiety agent, anti-inflammatory agent, appetite suppressant, cholesterol/lipid-lowering agent, and HDL-raising agent, and other therapeutic agents as defined herein.

The present invention is also directed to pharmaceutical combinations, comprising at least Compound I, or a prodrug, a polymorph or a pharmaceutical acceptable salt thereof, and at least one additional therapeutic agent, selected from the group consisting of anti-obesity agent, anti-diabetic agent, antidepressant agent, anti-anxiety agent, anti-inflammatory agent, appetite suppressant, cholesterol/lipid-lowering agent, and HDL-raising agent, and other therapeutic agents as defined herein.

According to one embodiment of the present invention, the anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, such as dapagliflozin, insulin, glucagon-like peptide-1 (GLP-1), GLP-1 agonists, and PTP-1B inhibitors.

According to one embodiment of the present invention, the additional therapeutic agent is an antiobesity agent.

Examples of suitable anti-obesity agents for use in combination with the compounds of the present invention include melanocortin receptor (MC4R) agonists, cannabinoid receptor modulators, endocannabinoid synthesis modulators, GPR119 agonists, inhibitors of fat absorption, growth hormone secretagogue receptor (GHSR) antagonists, galanin receptor modulators, orexin antagonists, SGLT2 inhibitors, DPP4 inhibitors, triple monoamine reuptake inhibitors, CCK agonists, GLP-1 agonists, and other Pre-proglucagon-derived peptides; NPY1 or NPY5 antagonist, NPY2 and NPY4 modulators, corticotropin releasing factor modulators, histamine receptor-3 (H3) modulators, aP2 inhibitors, PPAR gamma modulators, PPAR delta modulators, acetyl-CoA carboxylase (ACC) inhibitors, steroyl Co-A desaturase-1 (SCD-1) inhibitors, 11-β-HSD-1 inhibitors, adiponectin receptor modulators; beta 3 adrenergic agonists, thyroid receptor beta modulators, lipase inhibitors, serotonin receptor agonists, monoamine reuptake inhibitors or releasing agents, anorectic agents, CNTF (ciliary neurotrophic factor), BDNF (brain-derived neurotrophic factor), leptin and leptin receptor modulators, cannabinoid-1 receptor inverse agonists/neutral antagonists, DGAT inhibitors, opiate antagonists, and amylin receptor modulators.

Preferred antiobesity agents include SGLT2 inhibitors, such as those disclosed in U.S. Pat. No. 6,414,126. Most preferred anti-obesity agents include dapagliflozin and lipase inhibitors, such as orlistat, or monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The compounds of the present invention can be administered in oral dosage form. The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 30 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

The present invention includes within its scope pharmaceutical compositions including, as an active ingredient, a therapeutically effective amount of at least one of the compounds of the invention, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the invention.

Examples of suitable anti-obesity agents for use in combination with the compounds of the present invention include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adiponectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum) or lorcaserin (Arena)), 5HT6 antagonists, monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, tesofensine, dexamphetamine, phentermine, phenylpropanolamine or mazindol, anorectic agents such as topiramate (Johnson & Johnson), CNTF (ciliary neurotrophic factor)/AXOKINE® (Regeneron), BDNF (brain-derived neurotrophic factor), leptin and leptin receptor modulators, or cannabinoid-1 receptor inverse agonists/neutral antagonists, such as SR-141716 (Sanofi) or SLV-319 (Solvay), DGAT inhibitors such as those described in WO 2006/134317 (A1) (Astra Zeneca), WO 2006/044775 (A2) (Bayer), WO 2006/019020 (A1) (Sankyo), WO 2006/082010 (A1) (Roche), WO 2004/047755 (A2) (Japan Tobacco, Tularik), and WO 2005/0727401 (A2) (Amgen, Japan Tobacco) and combination agents such as Qnexa and Contrave.

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors including saxagliptin, vildagliptin and sitagliptin, SGLT2 inhibitors including dapagliflozin and canaglifozin, glycogen phosphorylase inhibitors, and/or meglitinides, as well as insulin, and/or glucagon-like peptide-1 (GLP-1), GLP-1 agonists and other incretins, SIRT activators (resveratrol) and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPAR α/γ dual agonist such as MK-767/KRP-297 (Merck/Kyorin; as described in Yajima, K. et al., *Am. J. Physiol. Endocrinol. Metab.*, 284:E966-E971 (2003)), AZ-242 (tesaglitazar; Astra-Zeneca; as described in Ljung, B. et al., *J. Lipid Res.*, 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of a hypolipidemic agent would be an HMG CoA reductase inhibitor which includes, but is not limited to lovastatin, pravastatin, simvastatin, fluvastatin, atorvastatin, pitavastatin, or rosuvastatin.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-SEPHADEX® (SECHOLEX®, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis*, 115:45-63 (1995) and *J. Med. Chem.*, 41:973 (1998).

The other lipid agent or lipid-modulating agent may be a cholesteryl transfer protein inhibitor (CETP) such as Pfizer's CP-529,414 as well as those disclosed in WO 00/38722 and in EP 818448 (Bayer) and EP 992496, and Pharmacia's SC-744 and SC-795, CETi-1, JTT-705 and anacetrapib.

The hypolipidemic agent may be an ileal Na+/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 00/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 00/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin, rosuvastatin, and ezetimibe as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in accordance with the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of MCHR1 receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in accordance with the present invention may be used alone or in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

VI. EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS, Preparatory/Analytical HPLC, and Chiral Separation Methods Employed in Characterization or Purification of Examples Method 1. PHENOMENEX® Synergi 4 μm ODS, 4.6×50 mm column; 4 min gradient at 4 mL/min, 10:90:0.2 to 90:10:0.2 MeOH—$H_2O$—$H_3PO_4$ with 1 min hold at the end of the gradient.

Method 2. YMC S5 ODS, 4.6×50 mm column; 4 min gradient at 4 mL/min, 10:90:0.2 to 90:10:0.2 MeOH—$H_2O$—$H_3PO_4$ with 1 min hold at the end of the gradient.

Method 3. PHENOMENEX® Luna 5 μm C18 4.6×50 mm column; 4 min gradient at 4 mL/min, 10:90:0.1 to 90:10:0.1 MeOH—$H_2O$—$H_3PO_4$ with 1 min hold at the end of the gradient.

Method 4. Column 1: SunFire C18 3.5 μm, 3.0×150 mm column; Column 2: Xbridge Phenyl 3.5 μm, 3.0×150 mm column; 12 min gradient at 1 mL/min, 5:95:0.05 to 95:5:0.05 MeOH—$H_2O$-TFA with 3 min hold at the end of the gradient. (Unless otherwise stated, retention times listed in Examples refer to the retention times of Column 1).

Method 5. SunFire C18 4.6×150 mm 3.5 μm; 15 min gradient at 1 mL/min, 10:90:0.2 to 90:10:0.2 MeOH—$H_2O$—$H_3PO_4$ with 5 min hold at the end of the gradient.

NMR Employed in Characterization of Examples $^1$H NMR spectra were obtained with Bruker or JEOL Fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Nitrobenzene Syntheses 1-(2-Methoxy-4-nitrophenoxy)-2-methylpropan-2-ol

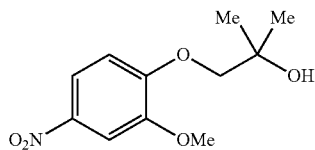 [SMILES: COc1cc([N+](=O)[O-])ccc1OCC(C)(C)O]

A solution of potassium 2-methoxy-4-nitrophenolate (29.0 g, 140 mmol), 1,2-epoxy-2-methylpropane (25.0 mL, 280 mmol), and $NaH_2PO_4 \cdot H_2O$ (17.4 g, 126 mmol) in a mixture of $CH_3CN$ (97 mL) and water (19 mL) was placed in a steel reaction vessel. The reaction mixture was heated to 160° C. (pressure~60 psi) for 7 h. The reaction mixture cooled to rt and stirred overnight. The reaction mixture was diluted with EtOAc and washed with sat. $NaHCO_3$ (3×), dried over anhydrous $Na_2SO_4$, and concentrated to yield 1-(2-methoxy-4-nitrophenoxy)-2-methylpropan-2-ol (30.6

(R)-1-Cyclopropyl-2-(2-methoxy-4-nitrophenoxy)ethanol

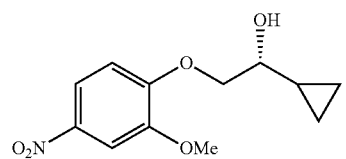

A. 1-Cyclopropyl-2-(2-methoxy-4-nitrophenoxy)ethanone

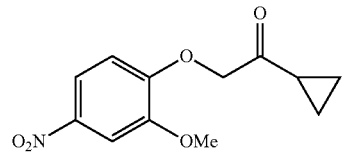

An orange suspension of 4-nitroguaiacol, potassium salt (0.867 g, 4.18 mmol) and 2-bromo-1-cyclopropylethanone (0.750 g, 4.60 mmol) in DMF (10 mL) was heated to 80° C. After 1 h, the suspension was cooled to rt and diluted with water (30 mL). A yellow solid precipitated, which was filtered, washed with water, and dried to afford 1-cyclopropyl-2-(2-methoxy-4-nitrophenoxy)ethanone (970 mg, 3.75 mmol, 90% yield). LC-MS, $[M+H]^+=252$.

B. (R)-1-Cyclopropyl-2-(2-methoxy-4-nitrophenoxy)ethanol

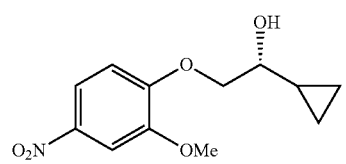 [SMILES: COc1cc([N+](=O)[O-])ccc1OC[C@H](O)C1CC1]

To a yellow solution of Part A (0.950 g, 3.78 mmol) in EtOH (10 mL) at rt was added NaBH$_4$ (0.150 g, 3.97 mmol). The yellow solution was stirred at rt for 45 min. The solution was diluted with water (10 mL), slowly quenched with AcOH (0.6 mL), and concentrated to remove the EtOH. The aqueous residue was diluted with water (10 mL) and extracted with EtOAc (2×25 mL). The combined organic layers were dried over MgSO$_4$, filtered, and the filtrate was concentrated to give 1-cyclopropyl-2-(2-methoxy-4-nitrophenoxy)ethanol (982 mg, 3.76 mmol, 99% yield) as an orange oil. The enantiomers were separated by chiral Prep-SFC (CHIRALPAK® IA, 250×4.6 mm ID, 10 µm; 35° C., 10% IPA: 90% CO$_2$; 10 µL injection volume; detector wavelength: 200 nm; RT$_1$: 7.0 min, RT$_2$: 7.9 min) to afford (R)-1-cyclopropyl-2-(2-methoxy-4-nitrophenoxy)ethanol (Enantiomer A). LC-MS, $[M+H]^+=254$.

3,3-Difluoro-1-((2-methoxy-4-nitrophenoxy)methyl)cyclobutanol

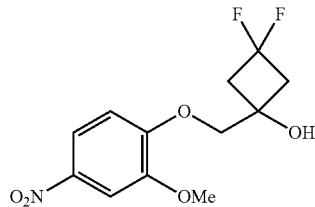 [SMILES: COc1cc([N+](=O)[O-])ccc1OCC1(O)CC(F)(F)C1]

A mixture of 5,5-difluoro-1-oxaspiro[2.3]hexane (7.24 g, 24.1 mmol), potassium 2-methoxy-4-nitrophenolate (5.00 g, 24.1 mmol) and NaH$_2$PO$_4$.H$_2$O (2.61 g, 21.7 mmol) in 50 mL CH$_3$CN-water (85:15) was heated at 130° C. in a steel bomb for 3.5 h. The reaction mixture was diluted with EtOAc, washed with 5% aq. Na$_2$CO$_3$, dried (MgSO$_4$), and concentrated to give 3,3-difluoro-1-((2-methoxy-4-nitrophenoxy)methyl)cyclobutanol (5.00 g, 17.3 mmol, 72% yield) as an off-white solid, which was used without further purification.

(S)-1-(Ethylsulfonyl)-3-(2-methoxy-4-nitrophenoxy)propan-2-ol

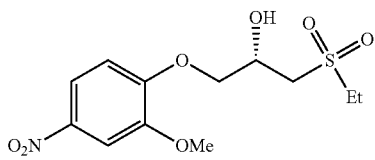 [SMILES: CCS(=O)(=O)C[C@@H](O)COc1ccc([N+](=O)[O-])cc1OC]

A. (R)-2-((2-Methoxy-4-nitrophenoxy)methyl)oxirane

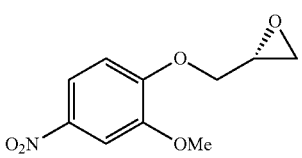 [SMILES: COc1cc([N+](=O)[O-])ccc1OC[C@H]1CO1]

DEAD (5.22 g, 30.0 mmol) (40% in toluene) was added dropwise to a stirred solution of 2-methoxy-4-nitrophenol (3.38 g, 20.0 mmol), (S)-oxiran-2-ylmethanol (1.78 g, 24.0 mmol), and PPh$_3$ (6.29 g, 24.0 mmol) in THF (25 mL) at 4° C. The mixture was stirred at rt for 14 h. The reaction mixture was diluted with EtOAc, washed with sat. NaHCO$_3$, dried (MgSO$_4$), and concentrated. The crude product was subjected to flash chromatography (silica gel, EtOAc/hexanes 0-100% gradient) to afford (R)-2-((2-methoxy-4-nitrophenoxy)methyl)oxirane (3.30 g, 14.7 mmol, 73% yield) as a pale oil, which solidified. LC-MS, $[M+H]^+=226$.

B. (S)-1-(Ethylthio)-3-(2-methoxy-4-nitrophenoxy) propan-2-ol

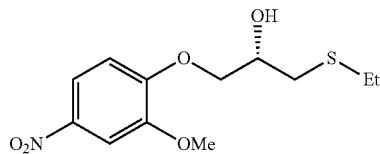 [SMILES: CCSC[C@@H](O)COc1ccc([N+](=O)[O-])cc1OC]

A solution of KOH (42.0 mg, 0.749 mmol) in water (0.14 mL) was added to a stirred solution of Part A (3.30 g, 14.7 mmol) and ethanethiol (1.64 g, 26.4 mmol) in THF (10 mL) at rt. The reaction mixture was stirred at rt for 14 h, diluted with DCM, and washed with sat. aq. NaHCO₃ solution. The organic phase was dried (MgSO₄) and concentrated to afford (S)-1-(ethylthio)-3-(2-methoxy-4-nitrophenoxy)propan-2-ol (4.00 g, 13.9 mmol, 95% yield) as a pale gum.

C. (S)-1-(Ethylsulfonyl)-3-(2-methoxy-4-nitrophenoxy)propan-2-ol

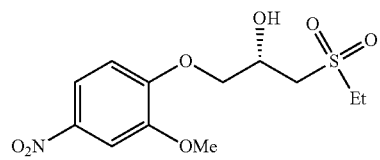

A mixture of Part B (3.30 g, 11.5 mmol) and mCPBA (7.72 g, 34.5 mmol) in DCM (115 ml) was stirred at rt for 45 min. The reaction mixture was diluted with DCM, washed with aq. 1 N NaOH and sat. NaHCO₃, dried (MgSO₄), and concentrated. The crude product was purified by flash chromatography (silica gel, hexanes/EtOAc 0-100% gradient) to afford (S)-1-(ethylsulfonyl)-3-(2-methoxy-4-nitrophenoxy)propan-2-ol (3.40 g, 10.7 mmol, 93% yield) as a yellow gum. LC-MS, [M+H]⁺=320.

4-((2-Methoxy-4-nitrophenoxy)methyl)tetrahydro-1,1-dioxido-2H-thiopyran-4-ol

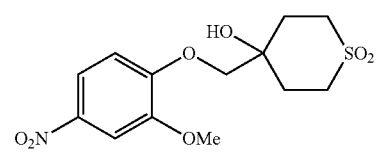 [SMILES: COc1cc([N+](=O)[O-])ccc1OCC1(O)CCS(=O)(=O)CC1]

A. 4-((2-Methoxy-4-nitrophenoxy)methyl)tetrahydro-2H-thiopyran-4-ol

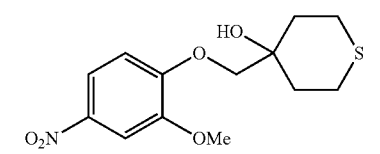 [SMILES: COc1cc([N+](=O)[O-])ccc1OCC1(O)CCSCC1]

A mixture of potassium 2-methoxy-4-nitrophenolate (3.02 g, 14.6 mmol), NaH₂PO₄·H₂O (2.01 g, 14.6 mmol), CH₃CN (12 mL), water (3 mL) and 1-oxa-6-thiaspiro[2.5]octane (1.90 g, 14.6 mmol) was heated at 150° C. for 3.5 h in a microwave reactor. After cooling to rt, the CH₃CN was mostly removed under vacuum and the remaining material was partitioned between EtOAc (100 mL) and H₂O (15 mL). The aqueous layer was extracted with EtOAc (2×15 mL) and the combined organic layers were dried (Na₂SO₄) and evaporated. The crude product purified by flash chromatography (silica gel, hexanes/EtOAc 0-40% gradient) to give a yellow solid. The solid was washed with EtOAc (~20 mL) to give 4-((2-methoxy-4-nitrophenoxy)methyl)tetrahydro-2H-thiopyran-4-ol (1.83 g, 6.11 mmol, 42% yield) as a yellow solid. LC-MS, [M−H₂O]⁺=282.

B. 4-((2-Methoxy-4-nitrophenoxy)methyl)tetrahydro-1,1-dioxido-2H-thiopyran-4-ol

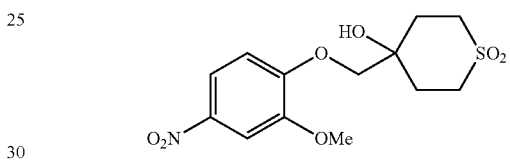

To a 0° C. solution of Part A (1.10 g, 3.67 mmol) in CH₂Cl₂ (30 mL) was added mCPBA (2.06 g, 9.19 mmol) portionwise. The reaction mixture was allowed to warm to rt and stirred for 30 min. The reaction mixture was concentrated. The crude material was redissolved in DMF (10 mL) and aq. sat. NaHCO₃ (20.0 mL, 3.67 mmol) was added. The reaction mixture was allowed to stir for 30 min. The solids were filtered off and dried under vacuum to yield 4-((2-methoxy-4-nitrophenoxy)methyl)tetrahydro-2H-thiopyran-4-ol 1,1-dioxide (1.10 g, 3.32 mmol, 91% yield) as a yellow oil. LC-MS, [M+H]⁺=332.

(2-(2-Methoxy-4-nitrophenoxy)ethyl)(methyl)sulfane

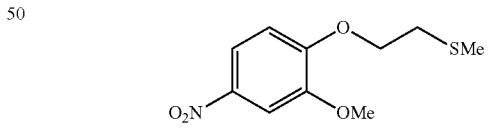

A mixture of potassium 2-methoxy-4-nitrophenolate hydrate (5.00 g, 22.2 mmol) and (2-chloroethyl)(methyl)sulfane (2.76 ml, 26.6 mmol) in DMF (44.4 ml) was stirred at 110° C. for 1 h. The reaction mixture was cooled to rt, diluted with DCM, washed with water and sat. NaHCO₃, dried (MgSO₄), and concentrated. The crude material was purified by flash chromatography (silica gel, hexanes/EtOAc 0-100% gradient) to afford (2-(2-methoxy-4-nitrophenoxy)ethyl)(methyl)sulfane (4.87 g, 20.0 mmol, 90% yield) as a yellow solid.

35

1-(2-(2-Methoxy-4-nitrophenoxy)ethylthio)-2-methylpropan-2-ol

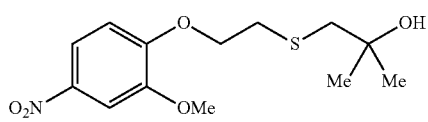 [SMILES: COc1cc([N+](=O)[O-])ccc1OCCSCC(C)(C)O]

A.
(2-(2-Methoxy-4-nitrophenoxy)ethyl)(trityl)sulfane

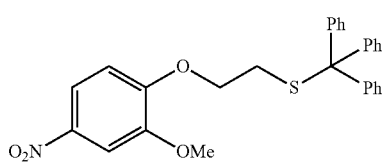 [SMILES: COc1cc([N+](=O)[O-])ccc1OCCSC(c1ccccc1)(c1ccccc1)c1ccccc1]

DIAD (1.35 ml, 6.92 mmol) was added slowly at 0° C. to a mixture of 2-methoxy-4-nitrophenol (0.900 g, 5.32 mmol), 2-(tritylthio)ethanol (1.88 g, 5.85 mmol), and PPh₃ (1.68 g, 6.39 mmol) in THF (26.6 ml) and the reaction mixture was stirred at rt overnight. The reaction mixture was diluted with EtOAc, washed with sat. NaHCO₃, dried (MgSO₄), and concentrated. The crude material was diluted with MeOH and the precipitate was filtered off. The mother liquor was concentrated and purified by flash chromatography (silica gel, hexanes/EtOAc 0-50% gradient) to afford (2-(2-methoxy-4-nitrophenoxy)ethyl)(trityl)sulfane (1.99 g, 3.80 mmol, 71% yield) as a light yellow solid.

B. 1-(2-(2-Methoxy-4-nitrophenoxy)ethylthio)-2-methylpropan-2-ol

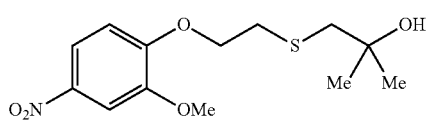 [SMILES: COc1cc([N+](=O)[O-])ccc1OCCSCC(C)(C)O]

A mixture of Part A (2.00 g, 4.24 mmol), triethylsilane (0.677 ml, 4.24 mmol), and TFA (0.980 ml, 12.7 mmol) in DCM (21.2 ml) was stirred at rt for 1 h. The reaction mixture was concentrated and the product was used without further purification. In a steel bomb, a mixture of the crude product (1.00 g, 4.36 mmol), 2,2-dimethyloxirane (0.944 g, 13.1 mmol), and K₂CO₃ (0.663 g, 4.80 mmol) in CH₃CN (17.45 ml) and water (4.36 ml) was stirred at 130° C. for 2 h and then at 100° C. overnight. The reaction mixture was diluted with DCM, washed with water and 1 N aq. HCl, dried (Na₂SO₄), and concentrated. The crude material was purified by flash chromatography (silica gel, hexanes/EtOAc 0-100% gradient) to afford 2-methoxy-4-nitrophenol (410 mg, 2.424 mmol, 56% yield) as a yellow solid and 1-(2-(2-methoxy-4-nitrophenoxy)ethylthio)-2-methylpropan-2-ol (239 mg, 0.634 mmol, 15% yield) as a brown gum.

36

(2-(2-(2-Fluoroethoxy)-4-nitrophenoxy)ethyl)(methyl)sulfane

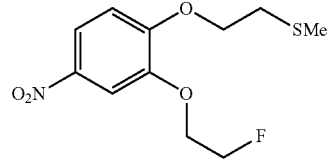 [SMILES: CSCCOc1ccc([N+](=O)[O-])cc1OCCF]

A. 2-(2-(Methylthio)ethoxy)-5-nitrophenol

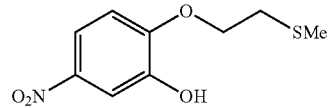 [SMILES: CSCCOc1ccc([N+](=O)[O-])cc1O]

A mixture of 4-nitrobenzene-1,2-diol (2.00 g, 12.9 mmol), (2-chloroethyl)(methyl)sulfane (1.43 g, 12.9 mmol) and K₂CO₃ (1.78 g, 12.9 mmol) in DMF (25 mL) was heated to 70° C. for 14 h. The reaction mixture was diluted with DCM, washed with sat. NH₄Cl, dried (MgSO₄), and concentrated. The crude product was subjected to flash chromatography (silica gel, hexane/EtOAc 0-100% gradient) to afford in the order of elution: (2,2'-(4-nitro-1,2-phenylene)bis(oxy)bis(ethane-2,1-diyl))bis(methylsulfane) (0.590 g, 1.95 mmol, 15% yield), 2-(2-(methylthio)ethoxy)-5-nitrophenol (1.20 g, 5.23 mmol, 41% yield), and nitro starting material (not isolated).

B. (2-(2-(2-Fluoroethoxy)-4-nitrophenoxy)ethyl)(methyl)sulfane

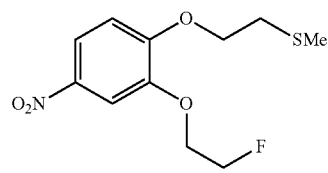 [SMILES: CSCCOc1ccc([N+](=O)[O-])cc1OCCF]

A mixture of Part A (100 mg, 0.436 mmol), 1-bromo-2-fluoroethane (554 mg, 4.36 mmol) and K₂CO₃ (60.3 mg, 0.436 mmol) in DMF (1 mL) was heated to 120° C. for 1 h. The reaction mixture was diluted with DCM, washed with water, dried (MgSO₄), and concentrated to afford (2-(2-(2-fluoroethoxy)-4-nitrophenoxy)ethyl)(methyl)sulfane, which was used without further purification.

(2-((2-Methoxy-4-nitrophenoxy)methoxy)ethyl)trimethylsilane

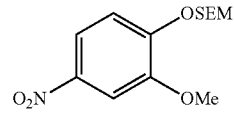

To a 0° C. solution of 2-methoxy-4-nitrophenol (1.00 g, 5.91 mmol) and SEM-Cl (2.10 mL, 11.8 mmol) in DCM (2.96 mL) was added DIPEA (4.13 mL, 23.7 mmol) dropwise and the solution warmed to rt and stirred for 22 h. The reaction mixture was poured into cold water (10 mL), extracted with DCM (3×15 mL), washed with water and brine, dried over anhydrous Na₂SO₄, and concentrated. The crude product was subjected to flash chromatography (silica gel, hexane/EtOAc 0-50% gradient) to provide (2-((2-methoxy-4-nitrophenoxy)methoxy)ethyl)trimethylsilane (1.70 g, 5.68 mmol, 96% yield) as a light yellow oil.

(2-((1-(2-Methoxy-4-nitrophenoxy)-2-methylpropan-2-yloxy)methoxy)ethyl)trimethylsilane

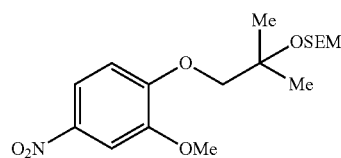

To a 0° C. solution of 1-(2-methoxy-4-nitrophenoxy)-2-methylpropan-2-ol (1.00 g, 4.15 mmol) and SEM-Cl (1.47 mL, 8.29 mmol) in DCM (2.07 mL) was added DIPEA (2.90 mL, 16.6 mmol) dropwise and the solution warmed to rt and stirred for 22 h. The reaction mixture was poured into cold water (10 mL), extracted with DCM (3×15 mL), washed with water and brine, dried over anhydrous Na₂SO₄, and concentrated. The crude product was subjected to flash chromatography (silica gel, hexane/EtOAc 0-50% gradient to give (2-((1-(2-methoxy-4-nitrophenoxy)-2-methylpropan-2-yloxy)methoxy)ethyl)trimethylsilane (1.44 g, 3.88 mmol, 94% yield) as a yellow oil. LC-MS, [M+H–HOSEM]⁺=242.

Procedure 1

Example 1

3-(2-Chlorophenoxy)-1-(4-(2-hydroxy-2-methylpropoxy)-3-methoxyphenyl)pyrrolidin-2-one

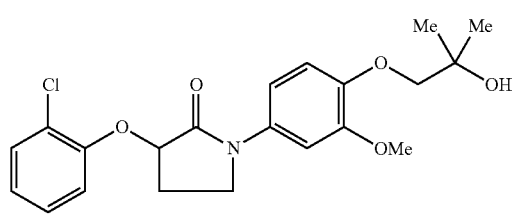 [SMILES: COc1cc(N2CCC(Oc3ccccc3Cl)C2=O)ccc1OCC(C)(C)O]

1A.
1-(4-Amino-2-methoxyphenoxy)-2-methylpropan-2-ol

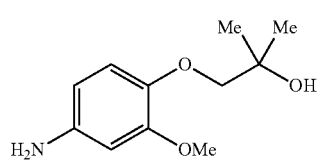

To a solution of 1-(2-methoxy-4-nitrophenoxy)-2-methylpropan-2-ol (295 mg, 1.23 mmol) in THF (7.0 mL) and EtOH (7.0 mL) was added Pd/C (5% dry basis, Degussa type: 50% water content) (100 mg, 0.0230 mmol) and the suspension was hydrogenated (1 atm, balloon) for 1.3 h. The suspension was filtered through Celite® and the filter cake was rinsed with MeOH (5×25 mL). Evaporation of the combined filtrates gave 1A (258 mg, 1.22 mmol, 100% yield) as a brown oil. LC-MS, [M+H]⁺=212.

Example 1

3-(2-Chlorophenoxy)-1-(4-(2-hydroxy-2-methylpropoxy)-3-methoxyphenyl)pyrrolidin-2-one To a stirred solution of 1A (0.211 g, 1.00 mmol) and NEt₃ (0.418 mL, 3.00 mmol) in THF (5 mL) was added 2,4-dibromobutanoyl chloride (0.264 g, 1.00 mmol) dropwise at rt. The mixture was stirred at rt for 5 min followed by the addition of 2-chlorophenol (129 mg, 1.00 mmol), a solution of KOH (0.281 g, 5.00 mmol) in water (0.5 mL) and TBAB (0.016 g, 0.050 mmol) in succession. The reaction mixture was stirred at rt for 14 h. The reaction mixture was diluted with EtOAc, washed with aq. sat. NaHCO₃, dried (MgSO₄), and concentrated. The crude product was subjected to flash chromatography (silica gel, EtOAc/hexanes 0-100% gradient) to afford the title compound as a white solid.

Procedure 2

Example 9

(R)-1-(4-(2-Hydroxy-2-methylpropoxy)-3-methoxyphenyl)-3-(4-(trifluoromethyl)phenoxy)pyrrolidin-2-one

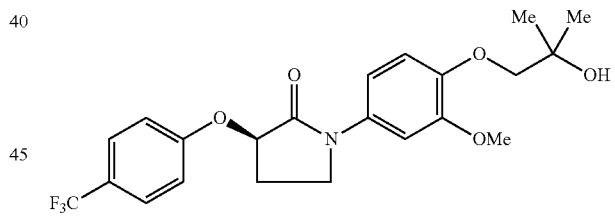

And Example 10

(S)-1-(4-(2-Hydroxy-2-methylpropoxy)-3-methoxyphenyl)-3-(4-(trifluoromethyl)phenoxy)pyrrolidin-2-one

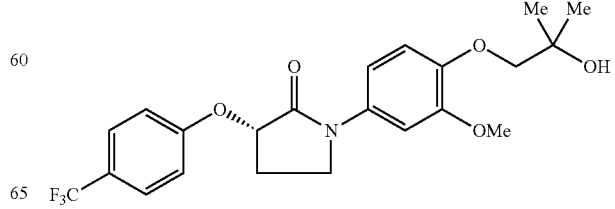

The enantiomers of Example 9 and Example 10 (161 mg, 0.366 mmol) were separated by chiral Prep-SFC (CHIRALPAK® OD-H, 30% MeOH: 70% CO₂; 10 μL injection volume; $t_{R1}$: 3.0 min, $t_{R2}$: 4.4 min) to afford Example 9 (Enantiomer A) (71 mg, 43% yield) and Example 10 (Enantiomer B) (69 mg, 42% yield).

Procedure 3

Example 12

1-(4-(2-Hydroxy-2-methylpropoxy)-3-methoxyphenyl)-3-(4-iodophenoxy)pyrrolidin-2-one

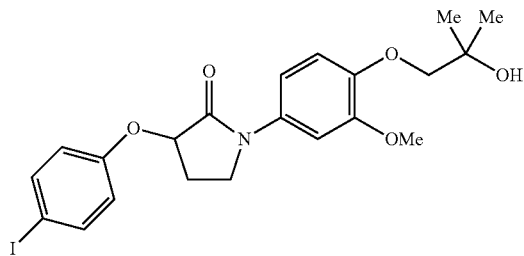 [SMILES: COc1cc(N2CCC(Oc3ccc(I)cc3)C2=O)ccc1OCC(C)(C)O]

To a stirred solution of 1-(4-amino-2-methoxyphenoxy)-2-methylpropan-2-ol (0.400 g, 1.89 mmol) and NEt₃ (0.290 ml, 2.08 mmol) in DCE (18.9 mL) was added 2,4-dibromobutanoyl chloride (0.250 ml, 1.89 mmol) dropwise at rt and the reaction mixture was stirred at rt for 10 min. A 30% aq. solution of KOH (1.77 ml, 9.46 mmol) and AMBERLITE® IRA-400 (0.189 g, 0.0950 mmol) were added and the reaction was allowed to stir at rt for 1 h. 4-Iodophenol (0.499 g, 2.27 mmol) was added and the reaction mixture was allowed to stir at 60° C. for 18 h. The reaction mixture was cooled to rt and filtered. The filtrate was washed with water (3×25 mL) and brine, dried over anhydrous Na₂SO₄, concentrated, and air dried under vacuum. The crude product was purified by flash chromatography (silica gel, EtOAc/hexanes 0-100% gradient) to afford the title compound (0.665 g, 1.32 mmol, 70% yield) as a light yellow foam.

Procedure 4

Example 13

1-(4-(2-Hydroxy-2-methylpropoxy)-3-methoxyphenyl)-3-methyl-3-(4-(trifluoromethoxy)phenoxy)pyrrolidin-2-one

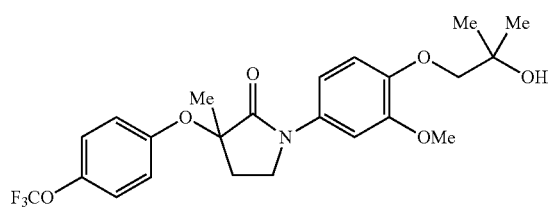 [SMILES: COc1cc(N2CCC(C)(Oc3ccc(OC(F)(F)F)cc3)C2=O)ccc1OCC(C)(C)O]

4A. 3-Methoxy-4-(2-methyl-2-((2-(trimethylsilyl)ethoxy)methoxy)propoxy)aniline

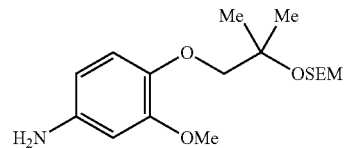

4A (1.19 g, 3.48 mmol, 90% yield) was prepared as a brown oil from (2-((1-(2-methoxy-4-nitrophenoxy)-2-methylpropan-2-yloxy)methoxy)ethyl)trimethylsilane (1.44 g, 3.88 mmol) and Pd/C (835 mg) following Procedure 1A. LC-MS, [M+H−HOSEM]⁺=194.

4B. 1-(3-methoxy-4-(2-methyl-2-((2-(trimethylsilyl)ethoxy)methoxy)propoxy)phenyl)-3-(4-(trifluoromethoxy)phenoxy)pyrrolidin-2-one

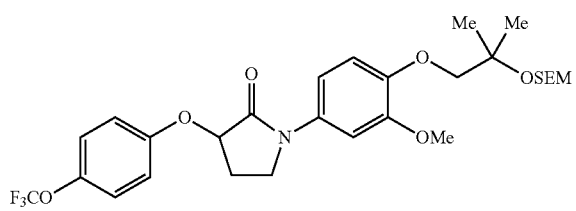

4B (45 mg, 0.077 mmol, 75% yield) was prepared as an off-white solid from 3-bromo-1-(3-methoxy-4-(2-methyl-2-((2-(trimethylsilyl)ethoxy)methoxy)propoxy)phenyl)pyrrolidin-2-one (50 mg, 0.10 mmol) and 4-(trifluoromethoxy)phenol (0.020 mL, 0.15 mmol) following Procedure 3. LC-MS, [M−HOSEM]⁺=438.

4C. 1-(3-Methoxy-4-(2-methyl-2-((2-(trimethylsilyl)ethoxy)methoxy)propoxy)phenyl)-3-methyl-3-(4-(trifluoromethoxy)phenoxy)pyrrolidin-2-one

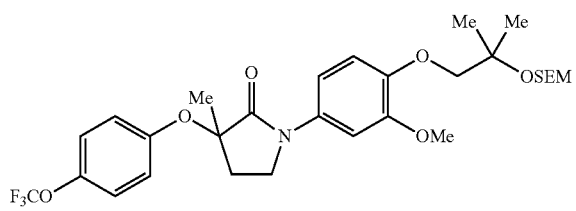

To a stirred solution of 4B (100 mg, 0.171 mmol) in THF (1.2 mL) was added a 1.0 M solution of LHMDS in THF (0.188 mL, 0.188 mmol) dropwise at −78° C. The mixture was stirred at −78° C. for 30 min followed by the addition of a solution of iodomethane (0.012 mL, 0.19 mmol) in THF (0.507 mL). The reaction mixture was then allowed to stir at −78° C. for 15 min. The reaction mixture was quenched with aq. sat. NH₄Cl at −78° C. and allowed to warm to rt. The reaction mixture extracted with EtOAc (3×15 mL) and the combined organic layers were washed with brine, dried over anhydrous Na₂SO₄, concentrated, and air dried under vacuum. The crude product was purified by flash chromatography (silica gel, EtOAc/hexanes 0-25% gradient) to afford 4C (77.7 mg, 0.130 mmol, 76% yield) as a light yellow oil. LC-MS, [M+H−HOSEM]+=452.

Example 13

1-(4-(2-Hydroxy-2-methylpropoxy)-3-methoxyphenyl)-3-methyl-3-(4-(trifluoromethoxy)phenoxy)pyrrolidin-2-one To a solution of 4C (75 mg, 0.13 mmol) in DCM (2.5 mL) at 0° C. was added TFA (0.096 mL, 1.3 mmol) and the reaction mixture was allowed to stir at rt for 30 min. The solvent was removed under vacuum and the crude material was redissolved in EtOAc and reconcentrated. The crude oil dissolved in DCM (10 mL), washed with sat. NaHCO₃ (3×), water, and brine, dried over anhydrous Na₂SO₄, concentrated, and air dried under vacuum. This material was purified by Prep-HPLC (MeOH/H₂O/TFA) to provide the title compound (26 mg, 0.056 mmol, 45% yield) as a clear oil.

Procedure 5

Example 22

3-(4-Cyclopropylphenoxy)-1-(4-(2-hydroxy-2-methylpropoxy)-3-methoxyphenyl)pyrrolidin-2-one

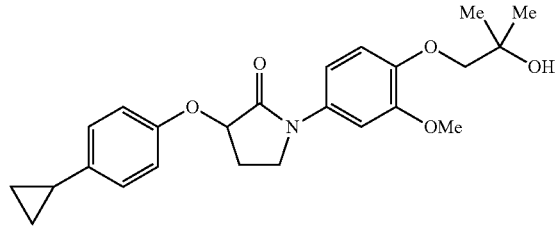 [SMILES: COc1cc(N2CCC(Oc3ccc(C4CC4)cc3)C2=O)ccc1OCC(C)(C)O]

5A. 3-(4-Cyclopropylphenoxy)-1-(3-methoxy-4-(2-methyl-2-((2-(trimethylsilyl)ethoxy)methoxy)propoxy)phenyl)pyrrolidin-2-one

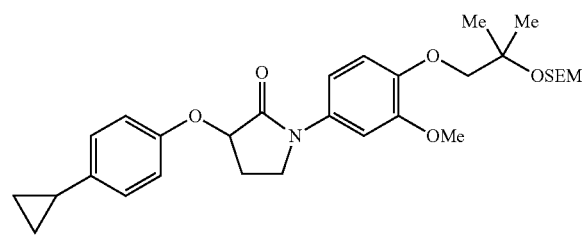

4-cyclopropylphenol (82 mg, 0.61 mmol) was added to a mixture of 3-bromo-1-(3-methoxy-4-(2-methyl-2-((2-(trimethylsilyl)ethoxy)methoxy)propoxy)phenyl) pyrrolidin-2-one (250 mg, 0.512 mmol), AMBERLITE® IRA-400 (51 mg, 0.026 mmol) in aq. 30% KOH (0.479 mL, 2.56 mmol) and DCE (4.1 mL) prepared from 3-methoxy-4-(2-methyl-2-((2-(trimethylsilyl)ethoxy)methoxy)propoxy)aniline (340 mg, 0.512 mmol), NEt₃ (0.078 ml, 0.563 mmol), and 2,4-dibromobutanoyl chloride (0.067 ml, 0.512 mmol), following Procedure 3. The reaction mixture was stirred at 50° C. for 20 h, cooled to rt, diluted with water (10 mL), and extracted with DCM (3×10 mL). The combined organic layers were washed with brine, dried over anhydrous Na₂SO₄, and concentrated. The crude product was purified by flash chromatography (silica gel, EtOAc/hexanes 0-30% gradient) to afford 5A (139 mg, 0.257 mmol, 50% yield) as an off-white solid.

Example 22

3-(4-Cyclopropylphenoxy)-1-(4-(2-hydroxy-2-methylpropoxy)-3-methoxyphenyl)pyrrolidin-2-one To a solution of 5A (37 mg, 0.068 mmol) in DCM (1.35 mL) at 0° C. was added TFA (0.053 mL, 0.68 mmol) and the reaction was allowed to warm to rt and stirred for 16 h. The solvent was removed in vacuo. The solid was triturated with ether (3×5 mL) and air dried under vacuum to yield the title compound (14 mg, 0.032 mmol, 47% yield) as a white solid.

Procedure 6

Example 24

3-(2'-Fluorobiphenyl-4-yloxy)-1-(4-(2-hydroxy-2-methylpropoxy)-3-methoxyphenyl)pyrrolidin-2-one

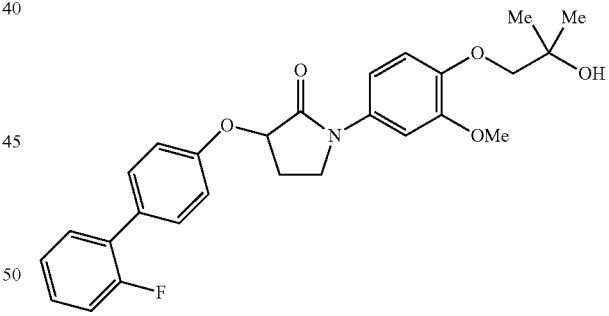

To a solution of 1-(4-(2-hydroxy-2-methylpropoxy)-3-methoxyphenyl)-3-(4-iodophenoxy)pyrrolidin-2-one (Example 12) (50.0 mg, 0.101 mmol) in degassed DMF (1.0 mL) was added Pd(PPh₃)₄ (3.49 mg, 3.02 µmol), Na₂CO₃ (0.126 mL, 0.251 mmol) and 2-fluorophenylboronic acid (14.1 mg, 0.101 mmol). The reaction mixture was purged, backfilled with nitrogen, and stirred at 110° C. for 1.0 h. The reaction mixture was cooled to rt, diluted with water (10 mL), and extracted with EtOAc (2×). The combined organic layers were washed with brine, dried over anhydrous Na₂SO₄, concentrated, and dried under vacuum overnight. The crude product was purified by flash chromatography (silica gel, EtOAc/hexanes 0-75% gradient) to afford the title compound (29 mg, 0.061 mmol, 61% yield) as a white solid.

Procedure 7

Example 34

1-(4-(2-Hydroxy-2-methylpropoxy)-3-methoxyphenyl)-3-(5-phenylpyridin-2-yloxy)pyrrolidin-2-one

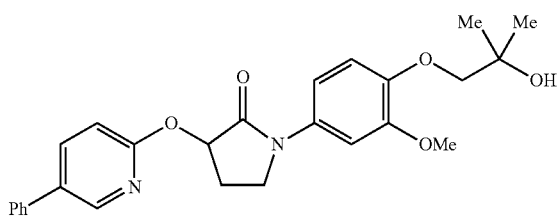

7A. 1-(3-Methoxy-4-(2-methyl-2-((2-(trimethylsilyl)ethoxy)methoxy)propoxy)phenyl)-3-(5-phenylpyridin-2-yloxy)pyrrolidin-2-one

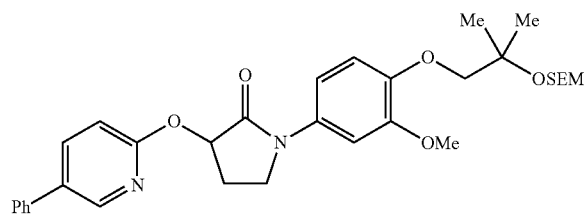

7A was prepared following Procedure 6. LC-MS, [M+H]$^+$=579.

Example 34

1-(4-(2-Hydroxy-2-methylpropoxy)-3-methoxyphenyl)-3-(5-phenylpyridin-2-yloxy)pyrrolidin-2-one Example 34 (6.1 mg, 0.013 mmol, 71.2% yield) was prepared as an off-white solid from 7A following Procedure 5B.

Procedure 8

Example 49

3-(Biphenyl-4-yloxy)-1-(4-((S)-3-(ethylsulfonyl)-2-hydroxypropoxy)-3-methoxyphenyl)pyrrolidin-2-one

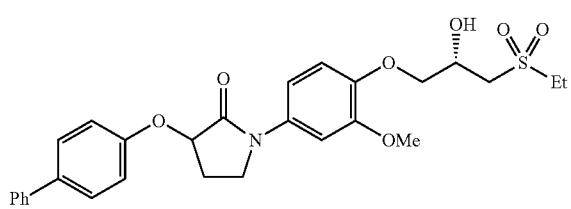 [SMILES: CCS(=O)(=O)C[C@@H](O)COc1ccc(N2CCC(Oc3ccc(-c4ccccc4)cc3)C2=O)cc1OC]

8A. 3-(Biphenyl-4-yloxy)-1-(3-methoxy-4-((2-(trimethylsilyl)ethoxy)methoxy)phenyl)pyrrolidin-2-one

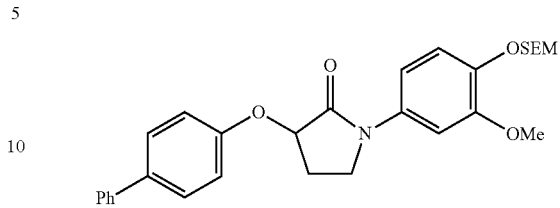

8A (1.16 g, 2.06 mmol, 54% yield) was prepared as a brown solid from 3-methoxy-4-((2-(trimethylsilyl)ethoxy)methoxy)aniline and biphenyl-4-ol following Procedure 1B. LC-MS, [M+H]$^+$=506.

8B. 3-(Biphenyl-4-yloxy)-1-(4-hydroxy-3-methoxyphenyl)pyrrolidin-2-one

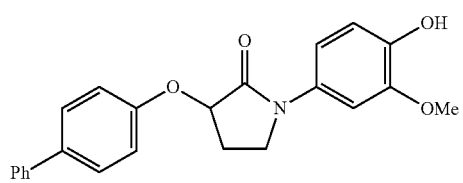 [SMILES: COc1cc(N2CCC(Oc3ccc(-c4ccccc4)cc3)C2=O)ccc1O]

A mixture of 8A (1.10 g, 2.18 mmol) and 4 N HCl in dioxane (5.44 ml, 21.8 mmol) in DCM (21.8 ml) was stirred at rt for 30 min. The reaction mixture was concentrated and triturated using ether to afford 8B (0.758 g, 2.02 mmol, 93% yield) as a light brown solid. LC-MS, [M+H]$^+$=376.

8C. 3-(Biphenyl-4-yloxy)-1-(3-methoxy-4-((R)-oxiran-2-ylmethoxy)phenyl)pyrrolidin-2-one

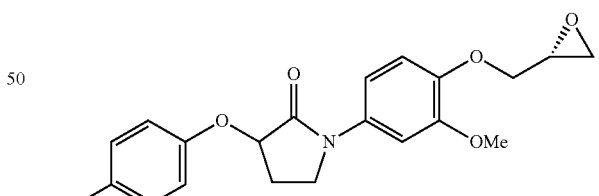

A mixture of 8B (100 mg, 0.266 mmol) and CsF (121 mg, 0.799 mmol) in DMF (2.66 mL) was stirred at rt for 20 min and then (R)-oxiran-2-ylmethyl 3-nitrobenzenesulfonate (90 mg, 0.35 mmol) was added. The mixture was stirred at rt overnight. The reaction mixture was diluted with DCM, washed with water and aq. sat. NaHCO$_3$, dried (MgSO$_4$), and concentrated. The crude product was purified by flash chromatography (silica gel, EtOAc/hexanes 0-100% gradient) to afford 8C (95.0 mg, 0.198 mmol, 74% yield) as a yellow solid. LC-MS, [M+H]$^+$=432.

8D. 3-(Biphenyl-4-yloxy)-1-(4-((S)-3-(ethylthio)-2-hydroxypropoxy)-3-methoxyphenyl)pyrrolidin-2-one

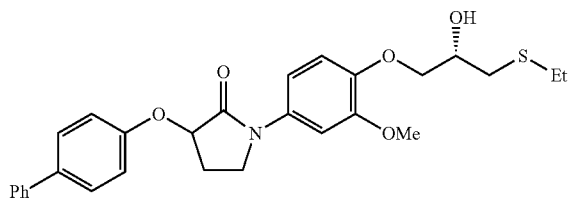 [SMILES: CCSC[C@@H](O)COc1ccc(N2CCC(Oc3ccc(-c4ccccc4)cc3)C2=O)cc1OC]

Ethanethiol (49 μL, 0.66 mmol) was added to a mixture of 8C (95 mg, 0.22 mmol) and aq. 30% KOH (41.2 μl, 0.220 mmol) in THF (2.2 mL) and stirred at 50° C. for 1.5 h. The reaction mixture was diluted with DCM, washed with sat. NaHCO₃, dried (MgSO₄), and concentrated. The crude product was purified by flash chromatography (silica gel, EtOAc/hexanes 0-90% gradient) to afford 8D (87 mg, 0.16 mmol, 72% yield) as a light yellow solid. LC-MS, [M+H]⁺=494.

Example 49

3-(Biphenyl-4-yloxy)-1-(4-((S)-3-(ethylsulfonyl)-2-hydroxypropoxy)-3-methoxyphenyl)pyrrolidin-2-one A mixture of 8D (87 mg, 0.18 mmol) and mCPBA (118 mg, 0.529 mmol) in DCM was stirred at rt for 45 min. The reaction mixture was diluted with DCM, washed with sat. NaHCO₃, dried (MgSO₄), and concentrated. The crude product was purified by flash chromatography (silica gel, hexanes/DCM/EtOAc 70:30:0 to 0:0:100 gradient) to afford the title compound (76 mg, 0.14 mmol, 79% yield) as an off-yellow solid.

Procedure 9

Example 59

3-(Biphenyl-4-yloxy)-1-(4-((S)-2-hydroxy-3-(methylsulfonyl)propoxy)-3-methoxyphenyl)pyrrolidin-2-one

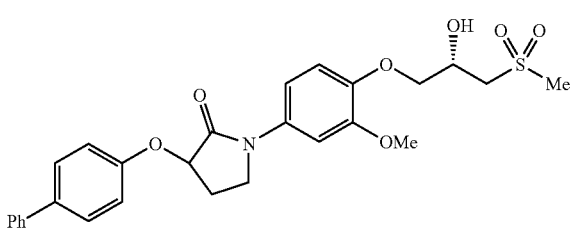 [SMILES: COc1cc(N2CCC(Oc3ccc(-c4ccccc4)cc3)C2=O)ccc1OC[C@H](O)CS(C)(=O)=O]

9A. 3-Bromo-1-(4-((S)-2-hydroxy-3-(methylthio)propoxy)-3-methoxyphenyl)pyrrolidin-2-one

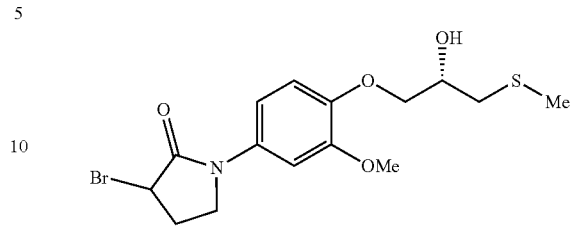

2,4-Dibromobutanoyl chloride (0.150 ml, 1.14 mmol) was added dropwise to a mixture of (S)-1-(4-amino-2-methoxyphenoxy)-3-(methylthio)propan-2-ol (0.276 g, 1.14 mmol) and NEt₃ (0.475 ml, 3.40 mmol) in DCM (11.4 ml) and stirred at rt for 15 min. Then, 30% aq. KOH (0.849 ml, 4.54 mmol) was added and the reaction mixture was stirred for an additional 15 min. The reaction mixture was diluted with DCM, washed with sat. NaHCO₃, dried (MgSO₄), and concentrated to afford 9A (450 mg, 1.04 mmol, 91% yield), which was used without further purification. LC-MS, [M+H]⁺=390, 392.

9B. 3-(Biphenyl-4-yloxy)-1-(4-((S)-2-hydroxy-3-(methylthio)propoxy)-3-methoxyphenyl)pyrrolidin-2-one

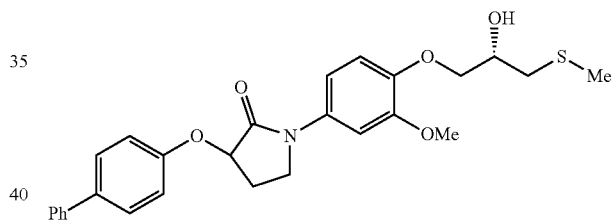

A mixture of 9A (100 mg, 0.256 mmol), biphenyl-4-ol (43.6 mg, 0.256 mmol), and K₂CO₃ (42.5 mg, 0.307 mmol) in DMF (2.56 mL) was stirred at 40° C. overnight. The reaction mixture was diluted with DCM, washed with sat. NaHCO₃, dried (Na₂SO₄), and concentrated. The crude product was purified by flash chromatography (silica gel, EtOAc/hexanes 0-100% gradient) to afford 9B (26 mg, 0.054 mmol, 21% yield) as a yellow solid. LC-MS, [M+H]⁺=480.

Example 59

3-(Biphenyl-4-yloxy)-1-(4-((S)-2-hydroxy-3-(methylsulfonyl)propoxy)-3-methoxyphenyl)pyrrolidin-2-one A mixture of 9B (20 mg, 0.042 mmol) and mCPBA (28.0 mg, 0.125 mmol) in DCM (417 μl) was stirred at rt. The reaction mixture was diluted with DCM, washed with sat. NaHCO₃, dried (Na₂SO₄), and concentrated. The crude product was purified using Prep-HPLC (MeOH/H₂O/TFA). The product was triturated with MeOH to afford the title compound (10 mg, 0.019 mmol, 46% yield) as a white solid. LC-MS, [M+H]⁺=512. HPLC-(Sunfire): $t_R$=9.49 min, purity=97%.

Procedure 10

Example 66

1-(3-Methoxy-4-(2-(methylsulfonyl)ethoxy)phenyl)-3-(4-(trifluoromethoxy)phenoxy)pyrrolidin-2-one

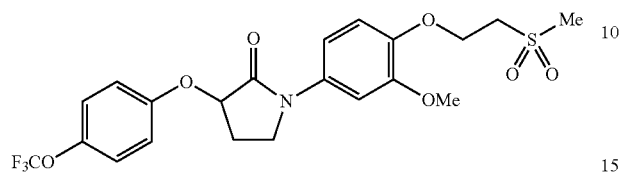

10A. 1-(3-Methoxy-4-((2-(trimethylsilyl)ethoxy)methoxy)phenyl)-3-(4-(trifluoromethoxy)phenoxy)pyrrolidin-2-one

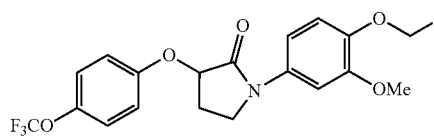

10A (109 mg, 0.191 mmol, 25% yield) was prepared from 3-methoxy-4-((2-(trimethylsilyl)ethoxy)methoxy)aniline and 4-(trifluoromethoxy)phenol following Procedure 1. LC-MS, [M+H]$^+$=514.

10B. 1-(3-Methoxy-4-(2-(methylthio)ethoxy)phenyl)-3-(4-(trifluoromethoxy)phenoxy)pyrrolidin-2-one

A mixture of 10A (108 mg, 0.210 mmol) and 4 N HCl in dioxane (526 µl, 2.10 mmol) in DCM (2 mL) was stirred at rt for 15 min. The reaction mixture was concentrated. The phenol was dissolved in DMF (3 mL) and (2-chloroethyl)(methyl)sulfane (21.8 µl, 0.210 mmol) and K$_2$CO$_3$ (29.1 mg, 0.210 mmol) were added and the reaction mixture was stirred at 90° C. overnight. The reaction mixture was diluted with DCM, washed with water and aq. sat. NaHCO$_3$, dried (Na$_2$SO$_4$), and concentrated. The crude product was purified by flash chromatography (silica gel, EtOAc/hexanes 0-100% gradient) to afford 10B (68 mg, 0.15 mmol, 71% yield) as a yellow solid. LC-MS, [M+H]$^+$=458.

Example 66

1-(3-Methoxy-4-(2-(methylsulfonyl)ethoxy)phenyl)-3-(4-(trifluoromethoxy)phenoxy)pyrrolidin-2-one A mixture of 10B (50 mg, 0.11 mmol) and mCPBA (73.5 mg, 0.328 mmol) in DCM (546 µL) was stirred at rt for 30 min. The reaction mixture was diluted with DCM, washed with 5% aq. NaHSO$_3$ and brine, dried (Na$_2$SO$_4$), and concentrated. The crude product was purified by Prep-HPLC (MeOH/H$_2$O/TFA) to provide the title compound (10 mg, 0.020 mmol, 18% yield) as a white solid.

Procedure 11

Example 68

3-(2'-Fluorobiphenyl-4-yloxy)-1-(3-methoxy-4-(2-(methylsulfonyl)ethoxy)phenyl)pyrrolidin-2-one

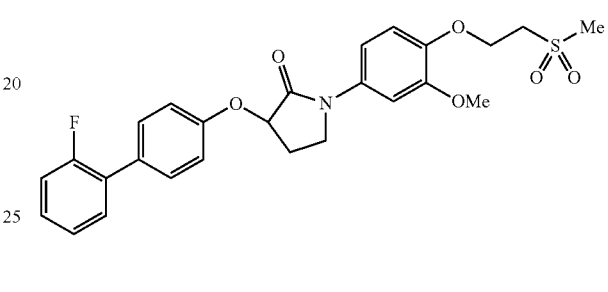

11A. 3-(2'-Fluorobiphenyl-4-yloxy)-1-(3-methoxy-4-(2-(methylthio)ethoxy)phenyl)pyrrolidin-2-one

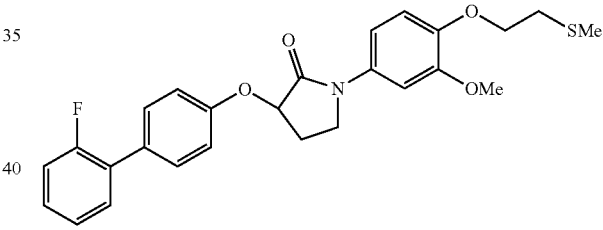

11A (120 mg, 0.231 mmol, 82% yield) was prepared from 3-(4-iodophenoxy)-1-(3-methoxy-4-(2-(methylthio)ethoxy)phenyl)pyrrolidin-2-one and 2-fluorophenylboronic acid following Procedure 6. LC-MS, [M+H]$^+$=468.

Example 68

3-(2'-Fluorobiphenyl-4-yloxy)-1-(3-methoxy-4-(2-(methylsulfonyl)ethoxy)phenyl)pyrrolidin-2-one A mixture of 11A (115 mg, 0.246 mmol) and mCPBA (138 mg, 0.615 mmol) in DCM (1230 µL) was stirred for 45 min. The reaction mixture was diluted with DCM, washed with aq. sat. NaHCO$_3$, dried (MgSO$_4$), and concentrated. The crude product was purified by flash chromatography (silica gel, hexanes/DCM/EtOAc 60:40:0 to 0:0:100 gradient). The product was triturated with MeOH to afford the title compound (77 mg, 0.15 mmol, 61% yield) as a white solid.

Procedure 12

Example 72

(R)-3-(4-Cyclopropylphenoxy)-1-(3-methoxy-4-(2-(methylsulfonyl)ethoxy)phenyl)pyrrolidin-2-one

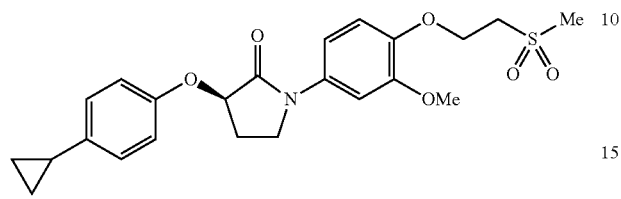

12A. 3-(4-Cyclopropylphenoxy)-1-(3-methoxy-4-(2-(methylthio)ethoxy)phenyl)pyrrolidin-2-one

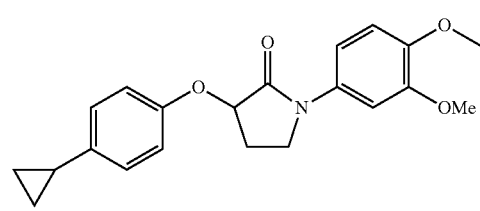

12A (0.940 g, 2.27 mmol, 46% yield) was prepared from 3-methoxy-4-(2-(methylthio)ethoxy)aniline and 4-cyclopropylphenol following Procedure 1. LC-MS, [M+H]$^+$=414.

B. (R)-3-(4-Cyclopropylphenoxy)-1-(3-methoxy-4-(2-(methylthio)ethoxy)phenyl)pyrrolidin-2-one

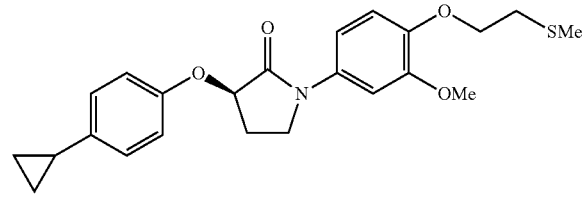 [SMILES: COc1cc(N2CC[C@@H](Oc3ccc(C4CC4)cc3)C2=O)ccc1OCCSC]

12A was separated by chiral Prep-SFC (CHIRALPAK® AS-H; (0.46×25 cm); mobile phase: 10% to 50% IPA/CH$_3$CN, 1:1 in CO$_2$ over 8 min, 50% for additional 4 min; Flow rate: 3 mL/min; 258 nm; 35° C.; 10 µL injection volume; t$_{R1}$: 5.4 min, t$_{R2}$: 6.3 min) to provide 12B (1.30 g, 3.14 mmol, 41% yield) (Enantiomer A) and (S)-3-(4-cyclopropylphenoxy)-1-(3-methoxy-4-(2-(methylthio)ethoxy)phenyl)pyrrolidin-2-one (1.42 g, 3.4 mmol, 44% yield) (Enantiomer B). LC-MS, [M+H]$^+$=414.

Example 72

(R)-3-(4-Cyclopropylphenoxy)-1-(3-methoxy-4-(2-(methylsulfonyl)ethoxy)phenyl)pyrrolidin-2-one A mixture of 12B (1.30 g, 3.14 mmol) and mCPBA (1.76 g, 7.86 mmol) in DCM (31.4 ml) was stirred at rt for 30 min. The reaction mixture was diluted with DCM, washed with aq. sat. Na$_2$CO$_3$ and aq. sat. NaHCO$_3$, dried (MgSO$_4$), and concentrated. The crude product was passed through a plug of silica gel (EtOAc:DCM, 1:1) and then triturated with MeOH to afford the title compound (1.04 g, 2.28 mmol, 72% yield) as a light yellow solid.

Procedure 13

Example 102

1-(3-Methyl-4-(2-(methylsulfinyl)ethoxy)phenyl)-3-(4-(trifluoromethoxy)phenoxy)pyrrolidin-2-one

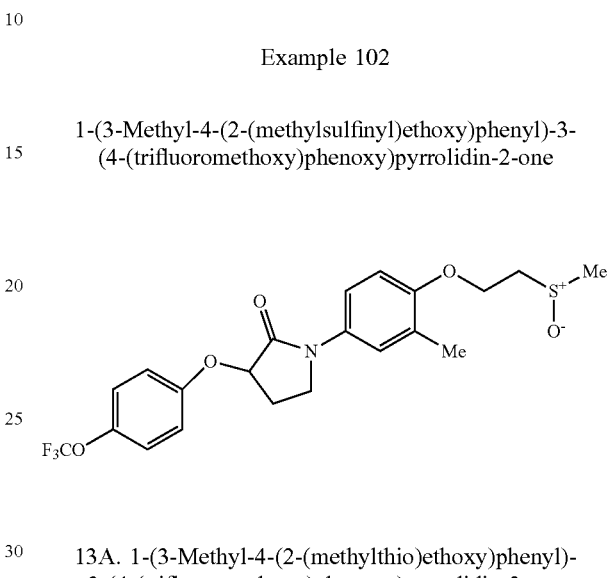

13A. 1-(3-Methyl-4-(2-(methylthio)ethoxy)phenyl)-3-(4-(trifluoromethoxy)phenoxy)pyrrolidin-2-one

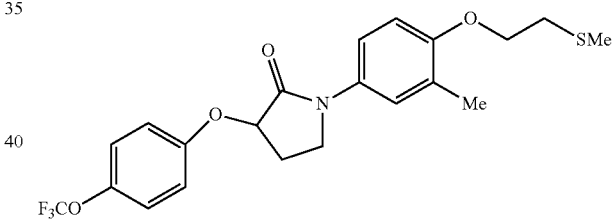

13A (169 mg, 0.382 mmol, 40% yield) was prepared as a brown solid from 3-methyl-4-(2-(methylthio)ethoxy)aniline and 4-(trifluoromethoxy)phenol following Procedure 1. LC-MS, [M+H]$^+$=442.

Example 102

1-(3-Methyl-4-(2-(methylsulfinyl)ethoxy)phenyl)-3-(4-(trifluoromethoxy)phenoxy)pyrrolidin-2-one A mixture of 13A (65 mg, 0.15 mmol) and mCPBA (33.0 mg, 0.147 mmol) in DCM (1472 µl) was stirred at rt for 10 min. The reaction mixture was diluted with DCM, washed with 5% aq. NaHSO$_3$, sat. NaHCO$_3$, and brine, dried (MgSO$_4$), and concentrated. The crude product was purified by flash chromatography (silica gel, DCM/EtOAc 100:0 to 50:50 gradient) to afford the title compound (39 mg, 0.084 mmol, 57% yield) as a light brown solid.

Procedure 14

Example 106

(R)-3-(Biphenyl-4-yloxy)-1-(3-methyl-4-(2-(methyl-sulfonyl)ethoxy)phenyl)pyrrolidin-2-one

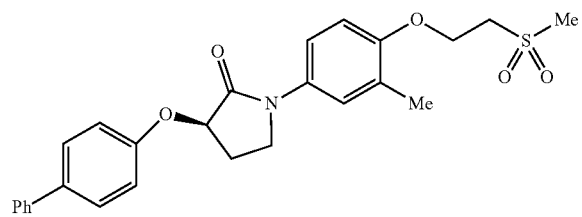 [SMILES: Cc1cc(N2CC[C@@H](Oc3ccc(-c4ccccc4)cc3)C2=O)ccc1OCCS(C)(=O)=O]

And Example 107

(S)-3-(Biphenyl-4-yloxy)-1-(3-methyl-4-(2-(methyl-sulfonyl)ethoxy)phenyl)pyrrolidin-2-one

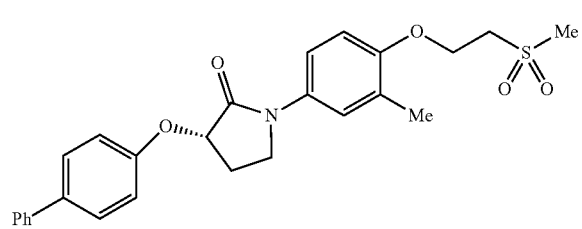 [SMILES: Cc1cc(N2CC[C@H](Oc3ccc(-c4ccccc4)cc3)C2=O)ccc1OCCS(C)(=O)=O]

14A. 3-(Biphenyl-4-yloxy)-1-(3-methyl-4-(2-(methylsulfonyl)ethoxy)phenyl)pyrrolidin-2-one

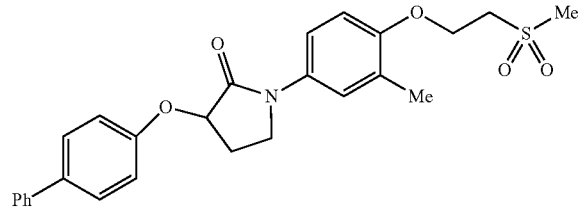 [SMILES: Cc1cc(N2CCC(Oc3ccc(-c4ccccc4)cc3)C2=O)ccc1OCCS(C)(=O)=O]

14A (218 mg, 0.448 mmol, 67% yield) was prepared as a white solid from 3-methyl-4-(2-(methylthio)ethoxy)aniline (0.224 g, 1.14 mmol) and biphenyl-4-ol (0.193 g, 1.14 mmol) following Procedure 9. LC-MS, [M+H]⁺=466.

Example 106

(R)-3-(Biphenyl-4-yloxy)-1-(3-methyl-4-(2-(methylsulfonyl)ethoxy)phenyl)pyrrolidin-2-one and Example 107

(S)-3-(Biphenyl-4-yloxy)-1-(3-methyl-4-(2-(methylsulfonyl)ethoxy)phenyl)pyrrolidin-2-one 14A was separated by chiral Prep-SFC. (CHIRALPAK® OD-H, 50% MeOH: 50% ACN; 25 µL injection volume; $t_{R1}$: 5.1 min, $t_{R2}$: 4.4 min) to provide Example 106 (Enantiomer A) (5.1 mg, 11 µmol, 42% yield) as a white solid with >99% ee. Example 107 (Enantiomer B) (5.1 mg, 11 µmol, 42% yield) as a white solid with >90% ee.

Procedure 15

Example 114

1-(3-Methyl-4-(2-(methylsulfonyl)ethoxy)phenyl)-3-(4-(pyridin-4-yl)phenoxy)pyrrolidin-2-one

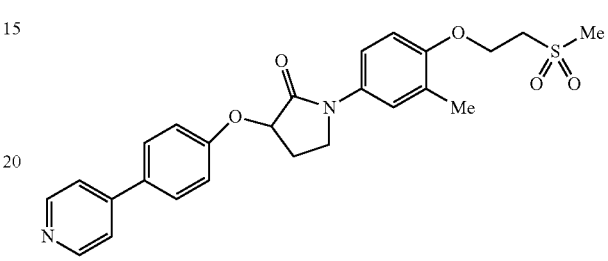

15A. 3-(4-Iodophenoxy)-1-(3-methyl-4-(2-(methyl-thio)ethoxy)phenyl)pyrrolidin-2-one

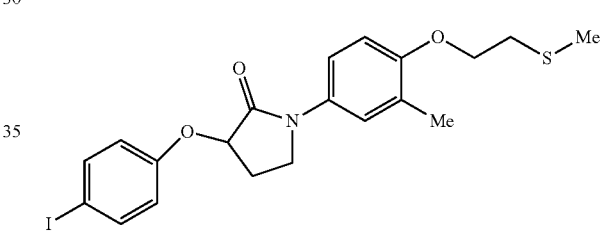

15A (0.460 g, 0.952 mmol, 50% yield) was prepared as a brown solid from 4-iodophenol (0.416 g, 1.89 mmol) and 3-methyl-4-(2-(methylthio)ethoxy)aniline (0.373 g, 1.89 mmol) following Procedure 9. LC-MS, [M+H]⁺=484.

15B. 1-(3-Methyl-4-(2-(methylthio)ethoxy)phenyl)-3-(4-(pyridin-4-yl)phenoxy)pyrrolidin-2-one, TFA

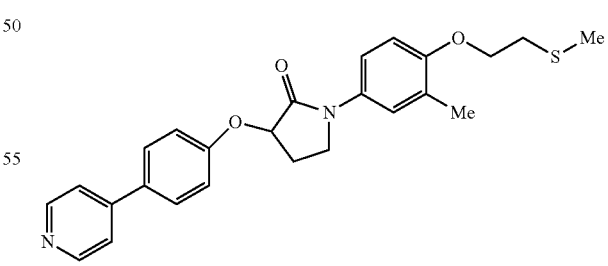

A mixture of 15A (70 mg, 0.15 mmol), pyridin-4-ylboronic acid (17.8 mg, 0.145 mmol), Na₂CO₃ (38.4 mg, 0.362 mmol), and Pd(PPh₃)₄ (8.4 mg, 7.2 µmol) in DMF (1.3 mL) and water (0.13 mL) was stirred under nitrogen at 100° C. for 1.5 h. The reaction mixture was diluted with DCM, washed with sat. NaHCO₃, dried (MgSO₄), and concentrated. The crude product was purified by Prep-HPLC (MeOH/H₂O/TFA) to afford 1-(3-methyl-4-(2-(methylthio)ethoxy)phenyl)-3-(4-(pyridin-4-yl)phenoxy)pyrrolidin-2-one, TFA 15B (52 mg, 0.095 mmol, 66% yield) as a yellow gummy solid. LC-MS, [M+H]⁺=435.

Example 114

1-(3-Methyl-4-(2-(methylsulfonyl)ethoxy)phenyl)-3-(4-(pyridin-4-yl)phenoxy)pyrrolidin-2-one A mixture of 15B (45 mg, 0.10 mmol) and mCPBA (69.6 mg, 0.311 mmol) in DCM (1.0 mL) was stirred at rt for 30 min. The reaction mixture was diluted with DCM, washed with sat. NaHCO₃ (3×), dried (Na₂SO₄), and concentrated. The crude product was purified by flash chromatography (silica gel, DCM/MeOH 100:0 to 90:10 gradient) to afford the title compound as a white solid.

Procedure 16

Example 116

1-(4-(2-Hydroxy-2-methylpropoxy)-3-methoxyphenyl)-3-(4-(trifluoromethoxy)phenoxy)-1H-pyrrol-2(5H)-one, H₂O

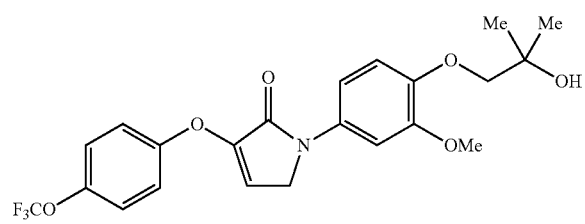 [SMILES: COc1cc(N2CC=C(Oc3ccc(OC(F)(F)F)cc3)C2=O)ccc1OCC(C)(C)O]

16A. 1-(3-Methoxy-4-(2-methyl-2-((2-(trimethylsilyl)ethoxy)methoxy)propoxy)phenyl)-3-(phenylselanyl)-3-(4-(trifluoromethoxy)phenoxy)pyrrolidin-2-one

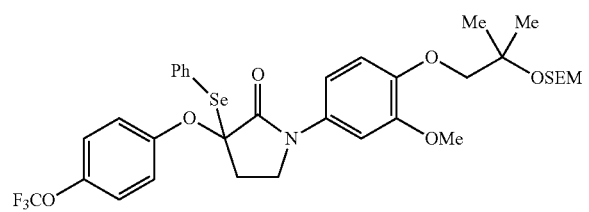

To a stirred solution of 4B (42 mg, 0.072 mmol) in THF (0.50 mL) was added a 1.0 M solution of LHMDS in THF (0.73 mL, 0.73 mmol) dropwise at −78° C. The mixture was stirred at −78° C. for 30 min followed by the addition of a solution of phenylselenenyl bromide (19 mg, 0.080 mmol) in THF (0.23 mL). The reaction mixture was stirred at −78° C. for 15 min. Sat. aq. NH₄Cl (1 mL) solution was added to the −78° C. reaction mixture, which was then allowed to warm to rt. The reaction mixture was extracted with EtOAc (3×15 mL), washed with sat. NaHCO₃, dried over anhydrous Na₂SO₄, and concentrated. The crude product was purified by flash chromatography (silica gel, hexanes/EtOAc 100:0 to 0:100 gradient) to provide 16A (38 mg, 0.052 mmol, 71% yield) isolated as an off-white solid. LC-MS, [M+H−HOSEM]⁺=594.

16B. 1-(3-Methoxy-4-(2-methyl-2-((2-(trimethylsilyl)ethoxy)methoxy)propoxy)phenyl)-3-(4-(trifluoromethoxy)phenoxy)-1H-pyrrol-2(5H)-one

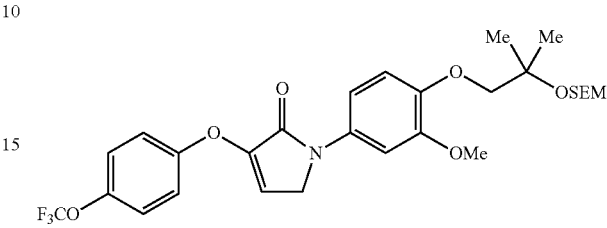

To a stirred solution of 16A (37 mg, 0.050 mmol) in DCM (0.50 mL) was added a 30% aq. solution of H₂O₂ (10 μL, 0.10 mmol) dropwise at 0° C. The mixture was allowed to warm to rt and stirred for 1 h. The reaction mixture was diluted with water (~10 mL), extracted with EtOAc (3×10 mL), washed with sat. NaHCO₃, dried over anhydrous Na₂SO₄, and concentrated to provide 16B (29 mg, 0.050 mmol, 99% yield) as a crude brown oil, which was used in the next step without further purification. LC-MS, [M+H−HOSEM]⁺=436.

Example 116

1-(4-(2-Hydroxy-2-methylpropoxy)-3-methoxyphenyl)-3-(4-(trifluoromethoxy)phenoxy)-1H-pyrrol-2(5H)-one To a solution of 16C (27 mg, 0.046 mmol) in DCM (1.0 mL) at 0° C. was added TFA (19 μL, 0.25 mmol) and the reaction mixture was allowed to stir at 0° C. for 1.0 h. The solvent was removed in vacuo and the orange oil was dissolved in MeOH and reconcentrated. The crude material was purified by Prep-HPLC (MeOH/H₂O/TFA) to afford the title compound (13 mg, 0.027 mmol, 58% yield) as a brown solid.

Procedure 17

Example 120

3-(4-Cyclopropylphenoxy)-1-(4-(2,3-dihydroxy-2-methylpropoxy)-3-methoxyphenyl)-1H-pyrrol-2(5H)-one, H₂O

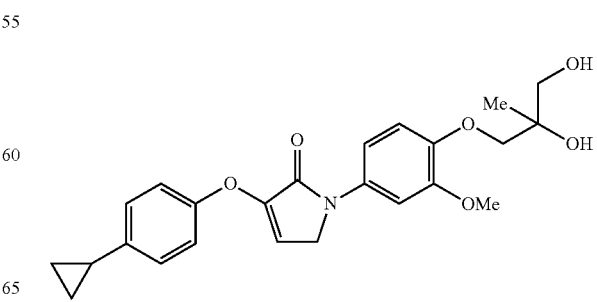

17A. 3-(4-Cyclopropylphenoxy)-1-(4-(2-hydroxy-2-methylpropoxy)-3-methoxyphenyl)-1H-pyrrol-2(5H)-one

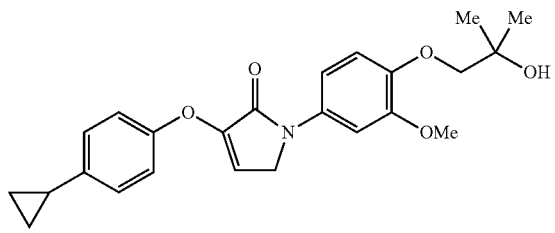 [SMILES: COc1cc(N2CC=C(Oc3ccc(C4CC4)cc3)C2=O)ccc1OCC(C)(C)O]

17A (1.03 g, 2.52 mmol) was prepared as a light tan solid following Procedure 16. LC-MS, [M+H]$^+$=410.

17B. 3-(4-Cyclopropylphenoxy)-1-(3-methoxy-4-(2-methylallyloxyl)phenyl)-1H-pyrrol-2(5H)-one

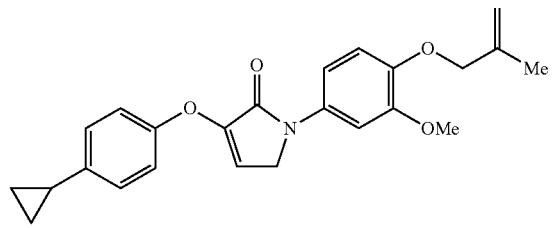 [SMILES: C=C(C)COc1ccc(N2CC=C(Oc3ccc(C4CC4)cc3)C2=O)cc1OC]

To a solution of 17A (100 mg, 0.244 mmol) and NEt$_3$ (0.068 mL, 0.49 mmol) in DCM (2.4 mL) at rt was added SOCl$_2$ (0.020 mL, 0.27 mmol) and the reaction mixture was allowed to stir at rt for 19 h. An additional amount of NEt$_3$ (0.068 mL, 0.49 mmol) and SOCl$_2$ (0.020 mL, 0.27 mmol) was added and reaction mixture was stirred at rt for 3 h. The reaction mixture was diluted with DCM (10 mL), washed with sat. NaHCO$_3$, water, and brine, dried over anhydrous Na$_2$SO$_4$, and concentrated. The crude product was purified by flash chromatography (silica gel, hexanes/EtOAc 100:0 to 0:100 gradient) to yield 17B (74 mg, 0.020 mmol, 77% yield) as a mixture of internal and terminal olefins. LC-MS, [M+H]$^+$=392.

Example 120

3-(4-Cyclopropylphenoxy)-1-(4-(2,3-dihydroxy-2-methylpropoxy)-3-methoxyphenyl)-1H-pyrrol-2(5H)-one To a solution of Part B as a mixture of internal and terminal olefins (74 mg, 0.19 mmol) in a mixture of acetone (2.24 mL) and water (0.560 mL) was added NMO (27 mg, 0.23 mmol) and OsO$_4$ (0.02 M in t-BuOH) (0.66 mL, 0.013 mmol) and the reaction mixture was stirred at rt for 24 h. The reaction mixture was diluted with EtOAc, washed with water and 5% Na$_2$S$_2$O$_3$, dried over anhydrous Na$_2$SO$_4$, and concentrated. The crude product was purified by Prep-HPLC (MeOH/H$_2$O/TFA) to afford the title compound (10 mg, 0.022 mmol, 12% yield) as a white solid.

The present invention is illustrated by but not restricted to the examples contained in Tables A to D. The tables also indicate for each Example which of seventeen synthetic methods was employed as well as which of five analytical methods was utilized. Detailed synthetic procedures as well as analytical HPLC conditions, solvent and column are described in the section after the Tables.

TABLE A

| Ex # | Ki (nM) | Structure | Synthetic Procedure Used | HPLC Method | t_R (min) | MS (M + H) | NMR Data |
|---|---|---|---|---|---|---|---|
| 1 | 5000 | (2-Cl phenyl ether, OMe, CH2-C(Me)2-OH on phenyl-pyrrolidinone) | 1 | 1 | 4.08 | 406 | $^1$H NMR (CDCl$_3$, 400 MHz) δ 7.61 (1 H, d, J = 2.5 Hz), 7.21-7.33 (2 H, m), 7.07-7.18 (1 H, m), 6.86-6.97 (1 H, m), 6.81-6.86 (1 H, m), 6.77-6.81 (1 H, m), 4.95 (1 H, t, J = 7.6 Hz), 3.85-3.92 (1 H, m), 3.80 (3 H, s), 3.73-3.79 (3 H, m), 2.56-2.66 (1 H, m), 2.29-2.42 (1 H, m), 1.27 (6 H, s). |
| 2 | 10000 | (3-Cl phenyl ether analog) | 1 | 1 | 4.11 | 406 | $^1$H NMR (CDCl$_3$, 500 MHz) δ 7.68 (1 H, d, J = 2.5 Hz), 7.22 (1 H, t, J = 8.1 Hz), 7.10 (1 H, t, J = 2.1 Hz), 6.97-7.02 (2 H, m), 6.89-6.93 (1 H, m), 6.83-6.87 (1 H, m), 5.02 (1 H, t, J = 7.7 Hz), 3.83-3.94 (5 H, m), 3.82 (2 H, s), 2.65-2.74 (1 H, m), 2.22-2.35 (1 H, m), 1.34 (6 H, s). |
| 3 | 2058 | (4-Cl phenyl ether analog) | 1 | 2 | 3.82 | 406 | $^1$H NMR (CDCl$_3$, 400 MHz) δ 7.69 (1 H, d), 7.26 (2 H, d, J = 8.65 Hz), 7.05 (2 H, d, J = 9.16 Hz), 6.92 (1 H, d, J = 8.65 Hz), 6.85 (1 H, dd, J = 8.65, 2.03 Hz), 5.00 (1 H, t, J = 7.63 Hz), 3.79-3.98 (7 H, 2 singlets overlapping a multiplet), 2.59-2.76 (1 H, m), 2.22-2.41 (1 H, m), 1.35 (6 H, s). |

TABLE A-continued
| Ex # | Ki (nM) | Structure | Synthetic Procedure Used | HPLC Method | $t_R$ (min) | MS (M + H) | NMR Data |
|---|---|---|---|---|---|---|---|
| 4 | 218 | 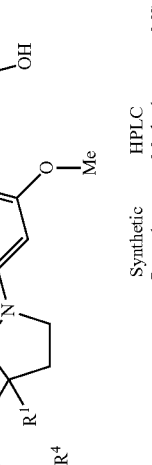 | 1 | 1 | 3.59 | 402 | $^1$H NMR (CDCl$_3$, 400 MHz) δ 7.70 (1 H, d, J = 2.4 Hz), 7.20 (1 H, t, J = 8.3 Hz), 6.88-6.93 (1 H, m), 6.82-6.88 (1 H, m), 6.63-6.70 (2 H, m), 6.55-6.60 (1 H, m), 5.02 (1 H, t, J = 7.7 Hz), 3.83-3.93 (5 H, m), 3.82 (2 H, s), 3.79 (3 H, s), 2.64-2.77 (1 H, m), 2.22-2.36 (1 H, m), 1.34 (6 H, s). |
| 5 | 662 | 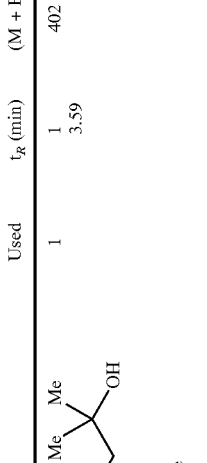 | 1 | 1 | 3.94 | 402 | $^1$H NMR (CDCl$_3$, 400 MHz) δ (1 H, d, J = 1.9 Hz), 6.98-7.23 (2 H, m), 6.83-6.91 (4 H, m), 4.94 (1 H, t, J = 7.7 Hz), 3.91 (3 H, s), 3.79-3.90 (4 H, m), 3.78 (3 H, s), 2.53-2.74 (1 H, m), 2.22-2.35 (1 H, m), 1.33 (6 H, s). |
| 6 | 7000 | 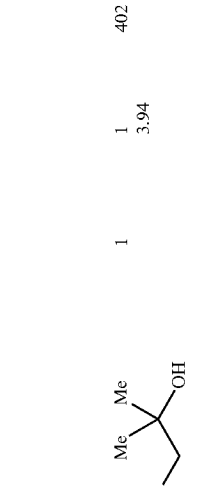 | 1 | 2 | 3.85 | 440 | $^1$H NMR (CDCl$_3$, 400 MHz) δ 7.66 (1 H, d, J = 2.4 Hz), 7.57 (1 H, d, J = 8.1 Hz), 7.48-7.55 (2 H, m), 7.08 (1 H, t, J = 7.1 Hz), 6.91 (1 H, d, J = 8.8 Hz), 6.84-6.88 (1 H, m), 5.07 (1 H, t, J = 7.3 Hz), 3.97 (10 H, ddd, J = 9.6, 8.5, 4.0 Hz), 3.87 (3 H, s), 3.82 (2 H, s), 3.79-3.87 (1 H, m), 2.60-2.70 (1 H, m), 2.40-2.50 (11 H, m, J = 13.5, 8.3, 6.8, 6.8 Hz), 1.34 (6 H, s). |

TABLE A-continued

| Ex # | Ki (nM) | Structure | Synthetic Procedure Used | HPLC Method $t_R$ (min) | MS (M + H) | NMR Data |
|---|---|---|---|---|---|---|
| 7 | 6000 | 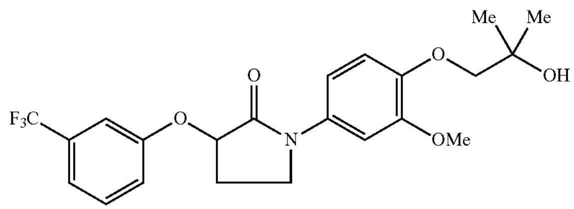 [SMILES: COc1cc(N2CCC(Oc3cccc(C(F)(F)F)c3)C2=O)ccc1OCC(C)(C)O] | 1 | 2<br>3.92 | 440 | $^1$H NMR (CDCl$_3$, 400 MHz) δ 7.66 (1 H, d, J = 2.4 Hz), 7.42 (1 H, t, J = 7.9 Hz), 7.24-7.35 (3 H, m), 6.91 (1 H, d, J = 8.8 Hz), 6.85 (1 H, dd, J = 8.6, 2.2 Hz), 5.08 (1 H, t, J = 7.7 Hz), 3.87 (3 H, s), 3.82 (2 H, s), 3.79-3.96 (2 H, m), 2.66-2.77 (1 H, m), 2.27-2.39 (1 H, m), 1.34 (6 H, s). |
| 8 | 34 | 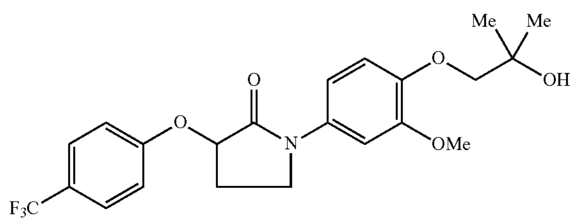 | 1 | 2<br>3.91 | 440 | $^1$H NMR (CDCl$_3$, 400 MHz) δ 7.68 (1 H, d, J = 2.4 Hz), 7.57 (2 H, d, J = 8.3 Hz), 7.17 (2 H, d, J = 8.3 Hz), 6.91 (1 H, d, J = 8.6 Hz), 6.85 (1 H, dd, J = 8.6, 2.4 Hz), 5.11 (1 H, t, J = 7.6 Hz), 3.87 (3 H, s), 3.82 (2 H, s), 3.80-3.98 (2 H, m), 2.66-2.77 (1 H, m), 2.28-2.40 (1 H, m), 1.34 (6 H, s). |
| 9 | 23 | 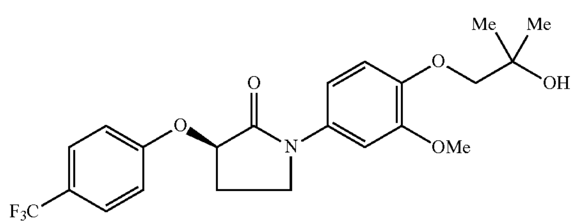 [SMILES: COc1cc(N2CC[C@@H](Oc3ccc(C(F)(F)F)cc3)C2=O)ccc1OCC(C)(C)O] | 2 | 4<br>10.12 | 440 | $^1$H NMR (CDCl$_3$, 400 MHz) δ 7.68 (1 H, d, J = 2.42 Hz), 7.57 (2 H, d, J = 8.58 Hz), 7.17 (2 H, d, J = 8.58 Hz), 6.89-6.95 (1 H, m), 6.82-6.88 (1 H, m), 5.11 (1 H, t, J = 7.59 Hz), 3.87 (3 H, s), 3.83-3.97 (2 H, m), 3.82 (2 H, s), 2.68-2.76 (1 H, m), 2.67 (1 H, m), 2.28-2.40 (1 H, m), 1.34 (6 H, s). |

TABLE A-continued

| Ex # | Ki (nM) | Structure | Synthetic Procedure Used | HPLC Method $t_R$ (min) | MS (M + H) | NMR Data |
|---|---|---|---|---|---|---|
| 10 | 6000 | (structure: pyrrolidinone with 3-(4-trifluoromethylphenoxy) and N-aryl with OMe and OCH₂C(Me)₂OH) | 2 | 4 10.12 | 440 | ¹H NMR (CDCl₃, 400 MHz) δ 7.68 (1 H, d, J = 2.42 Hz), 7.57 (2 H, d, J = 8.36 Hz), 7.17 (2 H, d, J = 8.80 Hz), 6.88-6.94 (1 H, m, J = 8.58 Hz), 6.85 (1 H, dd, J = 8.80, 2.64 Hz), 5.11 (1 H, t, J = 7.59 Hz), 3.87 (3 H, s), 3.85-3.98 (2 H, m), 3.82 (2 H, s), 2.69-2.77 (1 H, m), 2.70 (1 H, s), 2.27-2.42 (1 H, m), 1.34 (6 H, s). |
| 11 | 5000 | (structure: pyrrolidinone with 3-(3-trifluoromethoxyphenoxy) and N-aryl with OMe and OCH₂C(Me)₂OH) | 1 | 1 4.15 | 456 | ¹H NMR (CDCl₃, 400 MHz) δ 7.66 (1 H, d, J = 2.5 Hz), 7.30 (1 H, t, J = 8.1 Hz), 7.04 (1 H, dd, J = 8.4, 2.3 Hz), 6.96 (1 H, s), 6.82-6.92 (3 H, m), 5.03 (1 H, t, J = 7.6 Hz), 3.83-3.93 (5 H, m), 3.81 (2 H, s), 2.65-2.74 (1 H, m), 2.60 (1 H, br s), 2.25-2.36 (1 H, m), 1.33 (6 H, s). |
| 12 | 30 | (structure: pyrrolidinone with 3-(4-iodophenoxy) and N-aryl with OMe and OCH₂C(Me)₂OH) | 3 | 3 3.55 | 499 | ¹H NMR (DMSO-d₆, 500 MHz) δ 7.62 (2 H, d, J = 8.8 Hz), 7.49 (1 H, d, J = 2.2 Hz), 7.01-7.09 (1 H, m), 6.94-7.01 (1 H, m), 6.92 (2 H, d, J = 8.8 Hz), 5.23 (1 H, t, J = 8.0 Hz), 4.57 (1 H, s), 3.78-3.87 (2 H, m), 3.77 (3 H, s), 3.68 (2 H, s), 2.61-2.75 (1 H, m), 2.06 (1 H, dq, J = 12.4, 8.5 Hz), 1.20 (6 H, s). |

TABLE A-continued

| Ex # | Ki (nM) | Structure | Synthetic Procedure Used | HPLC Method $t_R$ (min) | MS (M + H) | NMR Data |
|---|---|---|---|---|---|---|
| 13 | 473 | 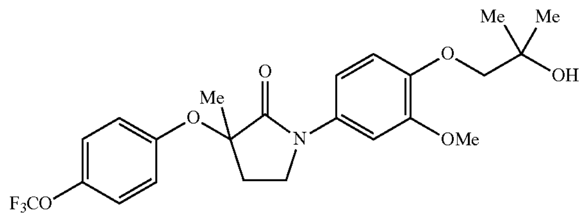 [SMILES: COc1cc(N2CCC(C)(Oc3ccc(OC(F)(F)F)cc3)C2=O)ccc1OCC(C)(C)O] | 4 | 3, 3.60 | 470 | $^1$H NMR (CDCl$_3$, 500 MHz) δ 7.65 (1 H, d, J = 2.8 Hz), 7.10 (4 H, d, q, J = 9.4 Hz), 6.89-6.95 (1 H, m), 6.78-6.89 (1 H, m), 3.89 (3 H, s), 3.83 (2 H, s), 3.77-3.82 (1 H, m), 3.66-3.74 (1 H, m), 2.73 (1 H, s), 2.61 (1 H, ddd, J = 13.3, 7.8, 5.8 Hz), 2.23 (1 H, ddd, J = 13.2, 7.7, 5.5 Hz), 1.61 (3 H, s), 1.35 (6 H, s). |
| 14 | 134 | 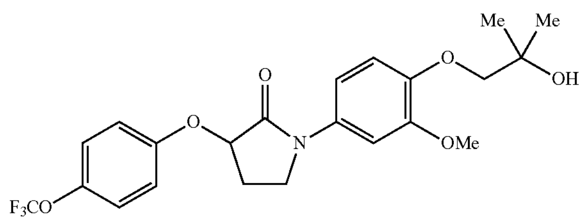 | 1 | 2, 3.94 | 456 | $^1$H NMR (CDCl$_3$, 400 MHz) δ 7.67 (1 H, d, J = 2.54 Hz), 7.16 (2 H, d, J = 8.65 Hz), 7.09 (2 H, d, J = 9.66 Hz), 6.91 (1 H, d, J = 8.65 Hz), 6.84 (1 H, dd, J = 8.65, 2.03 Hz), 5.02 (1 H, t, J = 7.63 Hz), 3.78-3.97 (7 H, 2 singlets overlapping a multiplet), 2.60-2.76 (1 H, m), 2.19-2.39 (1 H, m), 1.34 (6 H, s). |
| 15 | 11 | 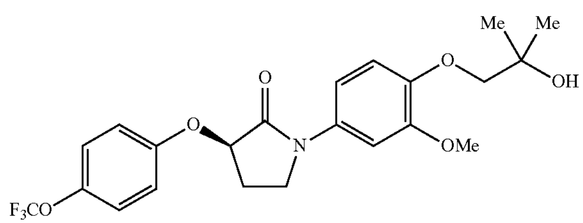 | 2 | 4, 10.6 | 456 | $^1$H NMR (CDCl$_3$, 400 MHz) δ 7.68 (1 H, d, J = 2.42 Hz), 7.13-7.19 (2 H, m), 7.07-7.13 (2 H, m), 6.89-6.94 (1 H, m), 6.84 (1 H, dd, J = 8.58, 2.42 Hz), 5.01 (1 H, t, J = 7.59 Hz), 3.87 (3 H, s), 3.83-3.95 (2 H, m), 3.82 (2 H, s), 2.76 (1 H, s), 2.62-2.73 (1 H, m), 2.26-2.38 (1 H, m), 1.33 (6 H, s). |

TABLE A-continued

| Ex # | Ki (nM) | Structure | Synthetic Procedure Used | HPLC Method $t_R$ (min) | MS (M + H) | NMR Data |
|---|---|---|---|---|---|---|
| 16 | 2335 | 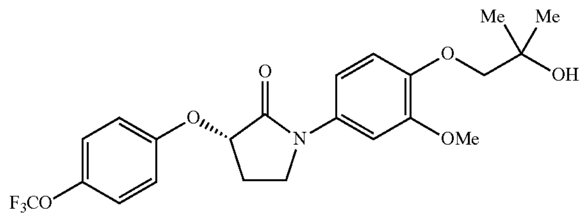 | 2 | 4 10.56 | 456 | $^1$H NMR (CDCl$_3$, 400 MHz) δ 7.68 (1 H, d, J = 2.42 Hz), 7.16 (2 H, d), 7.06-7.13 (2 H, m), 6.88-6.95 (1 H, m), 6.80-6.88 (1 H, m), 5.01 (1 H, t, J = 7.70 Hz), 3.87 (3 H, s), 3.82-3.97 (2 H, m), 3.82 (2 H, s), 2.76 (1 H, s), 2.62-2.74 (1 H, m), 2.25-2.39 (1 H, m), 1.33 (6 H, s). |
| 17 | 402 | 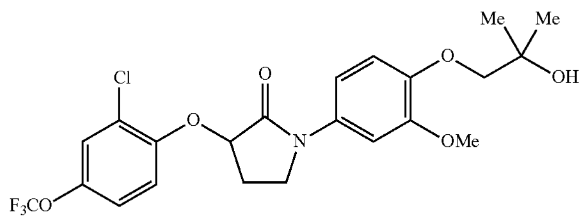 | 1 | 1 4.26 | 490 | $^1$H NMR (CDCl$_3$, 400 MHz) δ 7.65 (1 H, d, J = 2.0 Hz), 7.42 (1 H, d, J = 9.2 Hz), 7.28 (1 H, d, J = 2.5 Hz), 7.11 (1 H, dd, J = 8.9, 2.3 Hz), 6.82-6.94 (2 H, m), 5.00 (1 H, t, J = 7.6 Hz), 3.93-4.01 (1 H, m), 3.87 (3 H, s), 3.81-3.86 (3 H, m), 2.64-2.75 (1 H, m), 2.41-2.53 (1 H, m), 1.34 (6 H, s). |
| 18 | 959 | 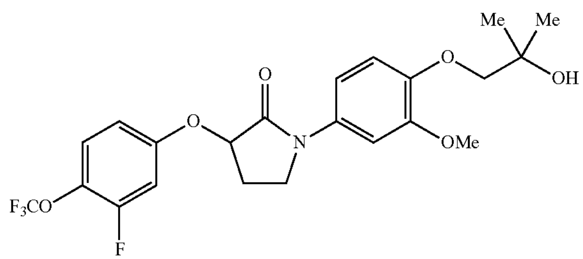 [SMILES: COc1cc(N2CCC(Oc3ccc(OC(F)(F)F)c(F)c3)C2=O)ccc1OCC(C)(C)O] | 1 | 1 4.12 | 474 | $^1$H NMR (CDCl$_3$, 400 MHz) δ 7.65 (1 H, d, J = 2.5 Hz), 7.22 (1 H, t, J = 8.8 Hz), 6.98 (1 H, dd, J = 11.5, 2.7 Hz), 6.87-6.93 (2 H, m), 6.82-6.86 (1 H, m), 5.01 (1 H, t, J = 7.7 Hz), 3.83-3.99 (5 H, m), 3.82 (2 H, s), 2.62-2.76 (1 H, m), 2.27-2.38 (1 H, m), 1.34 (6 H, s). |

TABLE A-continued

| Ex # | Ki (nM) | Structure | Synthetic Procedure Used | HPLC Method $t_R$ (min) | MS (M + H) | NMR Data |
|---|---|---|---|---|---|---|
| 19 | 4 | 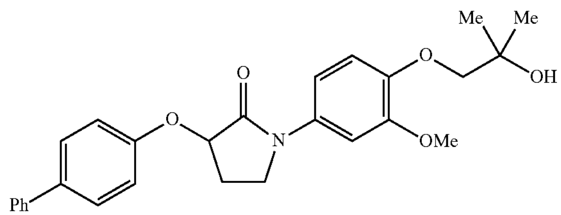 | 3 | 2<br>3.70 | 448 | $^1$H NMR (CDCl$_3$, 400 MHz) δ 7.71 (1 H, d, J = 2.2 Hz), 7.49-7.56 (4 H, m), 7.40 (2 H, t, J = 7.7 Hz), 7.29 (1 H, t, J = 7.4 Hz), 7.14 (2 H, d, J = 8.8 Hz), 6.88-6.92 (1 H, m, J = 8.8 Hz), 6.81-6.86 (1 H, m, J = 8.8, 2.2 Hz), 5.07 (1 H, t, J = 7.4 Hz), 3.87-3.93 (1 H, m), 3.86 (3 H, s), 3.81-3.85 (1 H, m), 3.81 (2 H, s), 2.64-2.75 (2 H, m), 2.25-2.37 (1 H, m), 1.32 (6 H, s). |
| 20 | 493 | 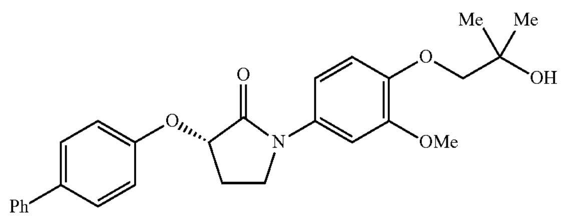 [SMILES: COc1cc(N2CC[C@H](Oc3ccc(-c4ccccc4)cc3)C2=O)ccc1OCC(C)(C)O] | 2 | 3<br>3.71 | 449 | $^1$H NMR (CDCl$_3$, 400 MHz) δ 7.71 (1 H, d, J = 2.2 Hz), 7.49-7.56 (4 H, m), 7.40 (2 H, t, J = 7.7 Hz), 7.29 (1 H, t, J = 7.4 Hz), 7.14 (2 H, d, J = 8.8 Hz), 6.88-6.92 (1 H, m, J = 8.8 Hz), 6.81-6.86 (1 H, m, J = 8.8, 2.2 Hz), 5.07 (1 H, t, J = 7.4 Hz), 3.87-3.93 (1 H, m), 3.86 (3 H, s), 3.81-3.85 (1 H, m), 3.81 (2 H, s), 2.64-2.75 (2 H, m), 2.25-2.37 (1 H, m), 1.32 (6 H, s). |
| 21 | 2 | 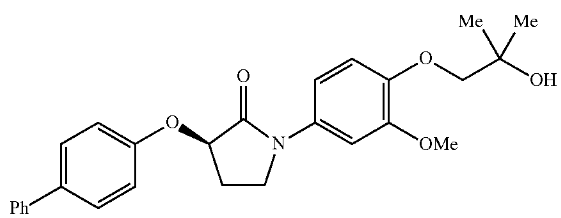 [SMILES: COc1cc(N2CC[C@@H](Oc3ccc(-c4ccccc4)cc3)C2=O)ccc1OCC(C)(C)O] | 2 | 3<br>3.70 | 449 | $^1$H NMR (CDCl$_3$, 400 MHz) δ 7.71 (1 H, d, J = 2.2 Hz), 7.49-7.56 (4 H, m), 7.40 (2 H, t, J = 7.7 Hz), 7.29 (1 H, t, J = 7.4 Hz), 7.14 (2 H, d, J = 8.8 Hz), 6.88-6.92 (1 H, m, J = 8.8 Hz), 6.81-6.86 (1 H, m, J = 8.8, 2.2 Hz), 5.07 (1 H, t, J = 7.4 Hz), 3.86 (3 H, s), 3.81-3.85 (1 H, m), 3.81 (2 H, s), 2.64-2.75 (2 H, m), 2.25-2.37 (1 H, m), 1.32 (6 H, s) |

TABLE A-continued

| Ex # | Ki (nM) | Structure | Synthetic Procedure Used | HPLC Method $t_R$ (min) | MS (M + H) | NMR Data |
|---|---|---|---|---|---|---|
| 22 | 23 | 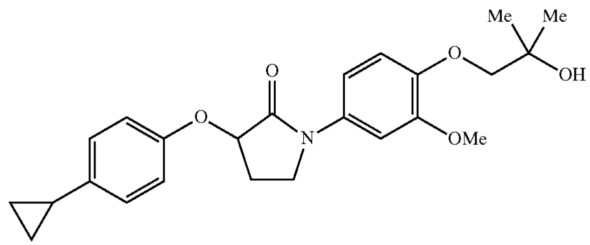 [SMILES: COc1cc(N2CCC(Oc3ccc(C4CC4)cc3)C2=O)ccc1OCC(C)(C)O] | 5 | 3, 3.52 | 413 | $^1$H NMR (DMSO-d$_6$, 500 MHz) δ 7.49 (1 H, d, J = 2.8 Hz), 6.89-7.09 (6 H, m), 5.14 (1 H, t, J = 8.0 Hz), 3.74-3.90 (5 H, m), 3.68 (2 H, s), 2.59-2.72 (1 H, m), 2.03 (1 H, dq, J = 12.6, 8.3 Hz), 1.78-1.93 (1 H, m), 1.20 (6 H, s), 0.82-0.94 (2 H, m), 0.53-0.65 (2 H, m). |
| 23 | 44 | 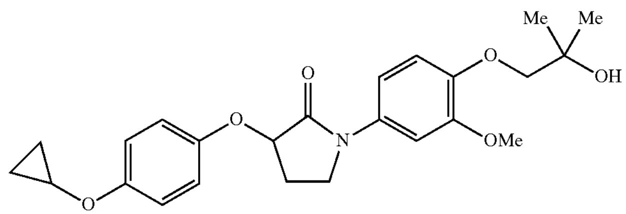 [SMILES: COc1cc(N2CCC(Oc3ccc(OC4CC4)cc3)C2=O)ccc1OCC(C)(C)O] | 1 | 4, 9.84 | 428 | $^1$H NMR (CDCl$_3$, 400 MHz) δ 7.69 (1 H, d, J = 2.42 Hz), 7.01-7.06 (2 H, m), 6.95-7.00 (2 H, m), 6.91 (1 H, d, J = 8.58 Hz), 6.85 (1 H, dd, J = 8.80, 2.64 Hz), 4.93 (1 H, t, J = 7.59 Hz), 3.88 (3 H, s), 3.82 (2 H, s), 3.77-3.94 (2 H, m), 3.65-3.73 (1 H, m), 3.49 (1 H, s), 2.57-2.73 (1 H, m), 2.21-2.38 (1 H, m), 1.34 (6 H, s), 0.69-0.80 (4 H, m). |
| 24 | 9 | 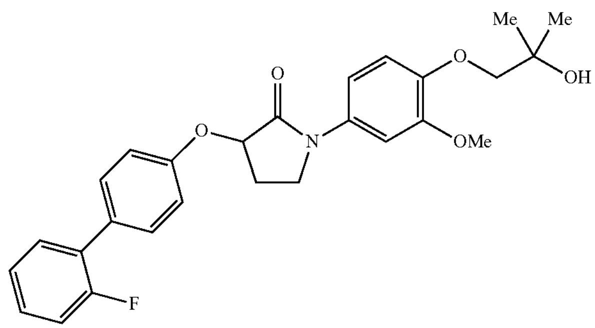 [SMILES: COc1cc(N2CCC(Oc3ccc(-c4ccccc4F)cc3)C2=O)ccc1OCC(C)(C)O] | 6 | 3, 3.69 | 466 | $^1$H NMR (DMSO-d$_6$, 500 MHz) δ 7.47-7.55 (4 H, m), 7.34-7.42 (1 H, m), 7.24-7.32 (2 H, m), 7.18 (2 H, d, J = 8.8 Hz), 7.07 (1 H, dd, J = 8.8, 2.8 Hz), 6.99 (1 H, d, J = 8.8 Hz), 5.31 (1 H, t, J = 8.0 Hz), 4.58 (1 H, s), 3.80-3.93 (2 H, m), 3.78 (3 H, s), 3.69 (2 H, s), 2.67-2.79 (1 H, m), 2.11 (1 H, dq, J = 12.4, 8.5 Hz), 1.20 (6 H, s). |

TABLE A-continued
| Ex # | Ki (nM) | Structure | Synthetic Procedure Used | HPLC Method $t_R$ (min) | MS (M + H) | NMR Data |
|---|---|---|---|---|---|---|
| 25 | 68 | 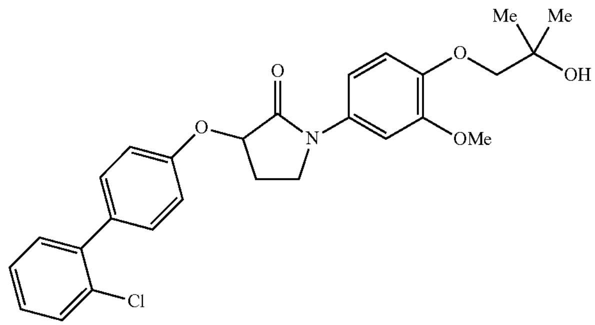 | 6 | 3 3.82 | 482 | $^1$H NMR (DMSO-d$_6$, 500 MHz) δ 7.55 (1 H, d, J = 7.7 Hz), 7.52 (1 H, d, J = 2.8 Hz), 7.34-7.43 (5 H, m), 7.16 (2 H, d, J = 8.8 Hz), 7.07 (1 H, dd, J = 8.8, 2.8 Hz), 6.99 (1 H, d, J = 8.8 Hz), 5.31 (1 H, t, J = 8.0 Hz), 4.58 (1 H, s), 3.80-3.91 (2 H, m), 3.78 (3 H, s), 3.69 (2 H, s), 2.67-2.80 (1 H, m), 2.12 (1 H, dq, J = 12.4, 8.5 Hz), 1.20 (6 H, s). |
| 26 | 81 | 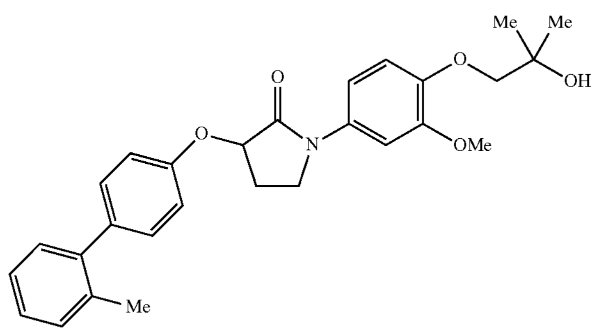 | 6 | 3 3.86 | 462 | $^1$H NMR (DMSO-d$_6$, 500 MHz) δ 7.53 (1 H, d, J = 2.2 Hz), 7.28 (3 H, d, J = 8.8 Hz), 7.21-7.26 (2 H, m), 7.17-7.21 (1 H, m), 7.13 (2 H, d, J = 8.8 Hz), 7.08 (1 H, dd, J = 8.8, 2.8 Hz), 7.00 (1 H, d, J = 8.8 Hz), 5.29 (1 H, t, J = 8.0 Hz), 4.58 (1 H, br. s.), 3.80-3.92 (2 H, m), 3.79 (3 H, s), 3.69 (2 H, s), 2.68-2.81 (1 H, m), 2.25 (3 H, s), 2.07-2.17 (1 H, m), 1.21 (6 H, s). |

TABLE A-continued
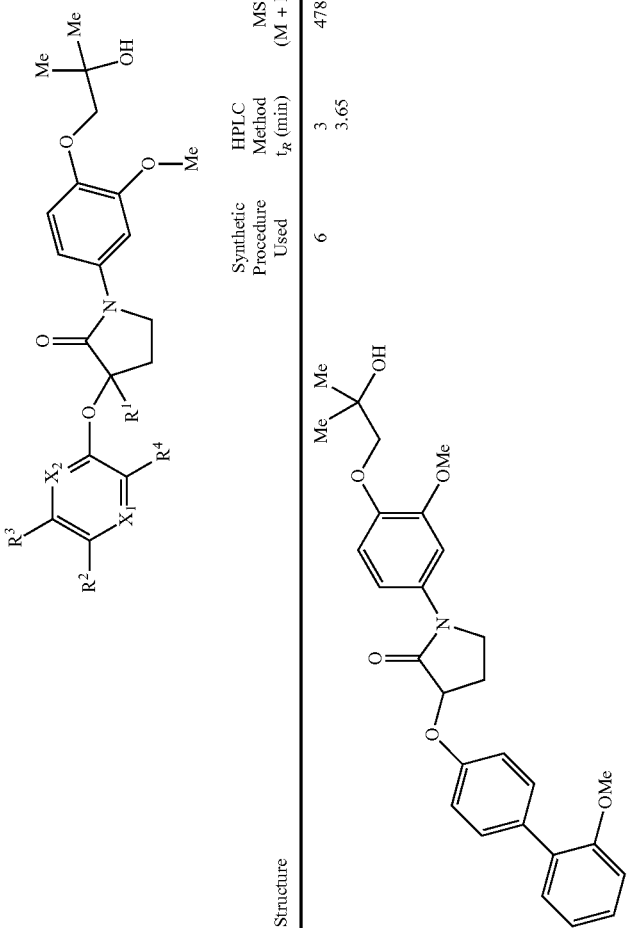
| Ex # | Ki (nM) | Structure | Synthetic Procedure Used | HPLC Method $t_R$ (min) | MS (M + H) | NMR Data |
|---|---|---|---|---|---|---|
| 27 | 238 | 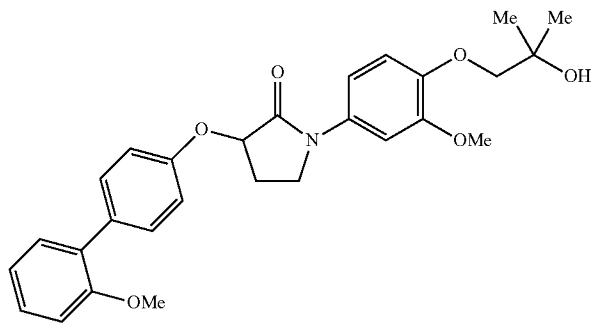 [SMILES: COc1cc(N2CCC(Oc3ccc(-c4ccccc4OC)cc3)C2=O)ccc1OCC(C)(C)O] | 6 | 3, 3.65 | 478 | $^1$H NMR (DMSO-d$_6$, 500 MHz) δ 7.52 (1 H, d, J = 2.2 Hz), 7.41 (2 H, d, J = 8.8 Hz), 7.31 (1 H, t, J = 7.7 Hz), 7.27 (1 H, d, J = 7.2 Hz), 7.04-7.14 (4 H, m), 6.96-7.04 (2 H, m), 5.27 (1 H, t, J = 8.0 Hz), 4.57 (1 H, s), 3.80-3.91 (2 H, m), 3.78 (3 H, s), 3.76 (3 H, s), 3.69 (2 H, s), 2.67-2.81 (1 H, m), 2.03-2.17 (1 H, m), 1.20 (6 H, s). |
| 28 | 956 | 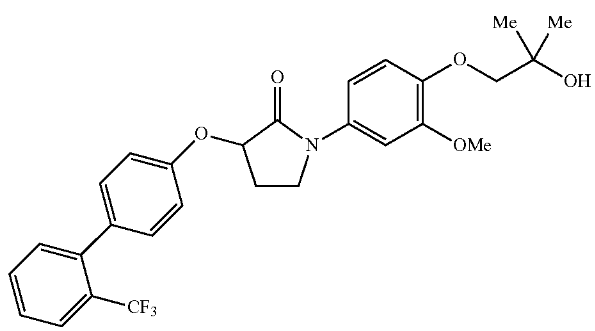 | 6 | 3, 3.82 | 516 | $^1$H NMR (DMSO-d$_6$, 500 MHz) δ 7.82 (1 H, d, J = 8.3 Hz), 7.71 (1 H, t, J = 7.4 Hz), 7.59 (1 H, t, J = 7.4 Hz), 7.52 (1 H, d, J = 2.8 Hz), 7.40 (1 H, d, J = 7.7 Hz), 7.26 (2 H, d, J = 8.3 Hz), 7.13 (2 H, d, J = 8.8 Hz), 7.07 (1 H, dd, J = 8.8, 2.2 Hz), 6.99 (1 H, d, J = 8.8 Hz), 5.30 (1 H, t, J = 8.0 Hz), 3.80-3.91 (2 H, m), 3.78 (3 H, s), 3.69 (2 H, s), 2.67-2.81 (1 H, m), 2.12 (1 H, dq, J = 12.4, 8.5 Hz), 1.20 (6 H, s). |

TABLE A-continued

| Ex # | Ki (nM) | Structure | Synthetic Procedure Used | HPLC Method t_R (min) | MS (M + H) | NMR Data |
|---|---|---|---|---|---|---|
| 29 | 87 | (structure with 3-Cl-4-Ph phenoxy and 3-OMe-4-(2-hydroxy-2-methylpropoxy)phenyl pyrrolidinone) | 6 | 3, 3.88 | 482 | $^1$H NMR (DMSO-d$_6$, 500 MHz) δ 7.51 (1 H, d, J = 2.2 Hz), 7.36-7.48 (5 H, m), 7.33-7.37 (1 H, m), 7.32 (1 H, d, J = 2.2 Hz), 7.14 (1 H, dd, J = 8.5, 2.5 Hz), 7.04-7.09 (1 H, m), 6.95-7.01 (1 H, m), 5.38 (1 H, t, J = 8.0 Hz), 3.79-3.91 (2 H, m), 3.78 (3 H, s), 3.69 (2 H, s), 2.66-2.77 (1 H, m), 2.13 (1 H, dq, J = 12.4, 8.5 Hz), 1.20 (6 H, s). |
| 30 | 12 | (structure with 3-F-4-Ph phenoxy and 3-OMe-4-(2-hydroxy-2-methylpropoxy)phenyl pyrrolidinone) | 6 | 3, 3.78 | 466 | $^1$H NMR (DMSO-d$_6$, 500 MHz) δ 7.42-7.56 (6 H, m), 7.32-7.40 (1 H, m), 6.92-7.18 (4 H, m), 5.35 (1 H, t, J = 8.3 Hz), 3.79-3.93 (2 H, m), 3.78 (3 H, s), 3.69 (2 H, s), 2.69-2.82 (1 H, m), 2.01-2.20 (1 H, m), 1.20 (6 H, s). |

TABLE A-continued
| Ex # | Ki (nM) | Structure | Synthetic Procedure Used | HPLC Method $t_R$ (min) | MS (M + H) | NMR Data |
|---|---|---|---|---|---|---|
| 31 | 34 | 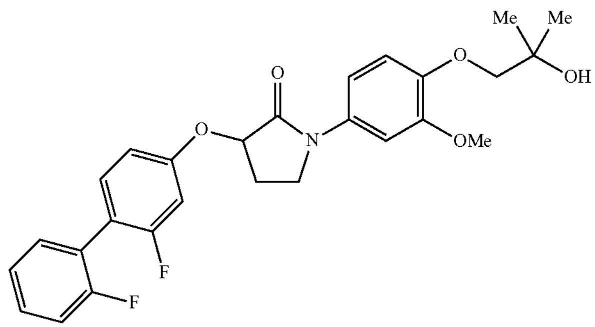 | 6 | 3  3.69 | 485 | $^1$H NMR (DMSO-d$_6$, 500 MHz) δ 7.51 (1 H, d, J = 2.2 Hz), 7.35-7.49 (3 H, m), 7.25-7.34 (2 H, m), 7.11 (1 H, dd, J = 12.1, 2.8 Hz), 7.04 (2 H, ddd, J = 18.0, 8.7, 2.5 Hz), 6.96-7.00 (1 H, m), 5.36 (1 H, t, J = 8.0 Hz), 3.78-3.94 (2 H, m), 3.77 (3 H, s), 3.68 (2 H, s), 2.74 (1 H, dddd, J = 12.7, 7.6, 7.3, 2.2 Hz), 2.12 (1 H, dq, J = 12.4, 8.5 Hz), 1.20 (6 H, s). |
| 32 | 634 | 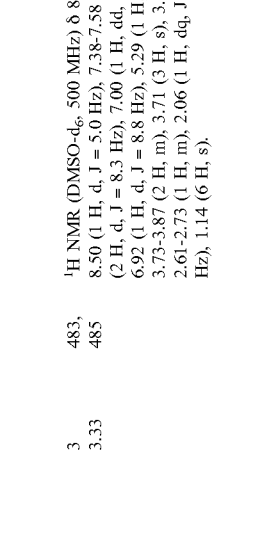 | 6 | 3  3.33 | 483, 485 | $^1$H NMR (DMSO-d$_6$, 500 MHz) δ 8.65 (1 H, s), 8.50 (1 H, d, J = 5.0 Hz), 7.38-7.58 (4 H, m), 7.15 (2 H, d, J = 8.3 Hz), 7.00 (1 H, dd, J = 8.8, 2.8 Hz), 6.92 (1 H, d, J = 8.8 Hz), 5.29 (1 H, t, J = 8.3 Hz), 3.73-3.87 (2 H, m), 3.71 (3 H, s), 3.62 (2 H, s), 2.61-2.73 (1 H, m), 2.06 (1 H, dq, J = 12.4, 8.5 Hz), 1.14 (6 H, s). |

TABLE A-continued
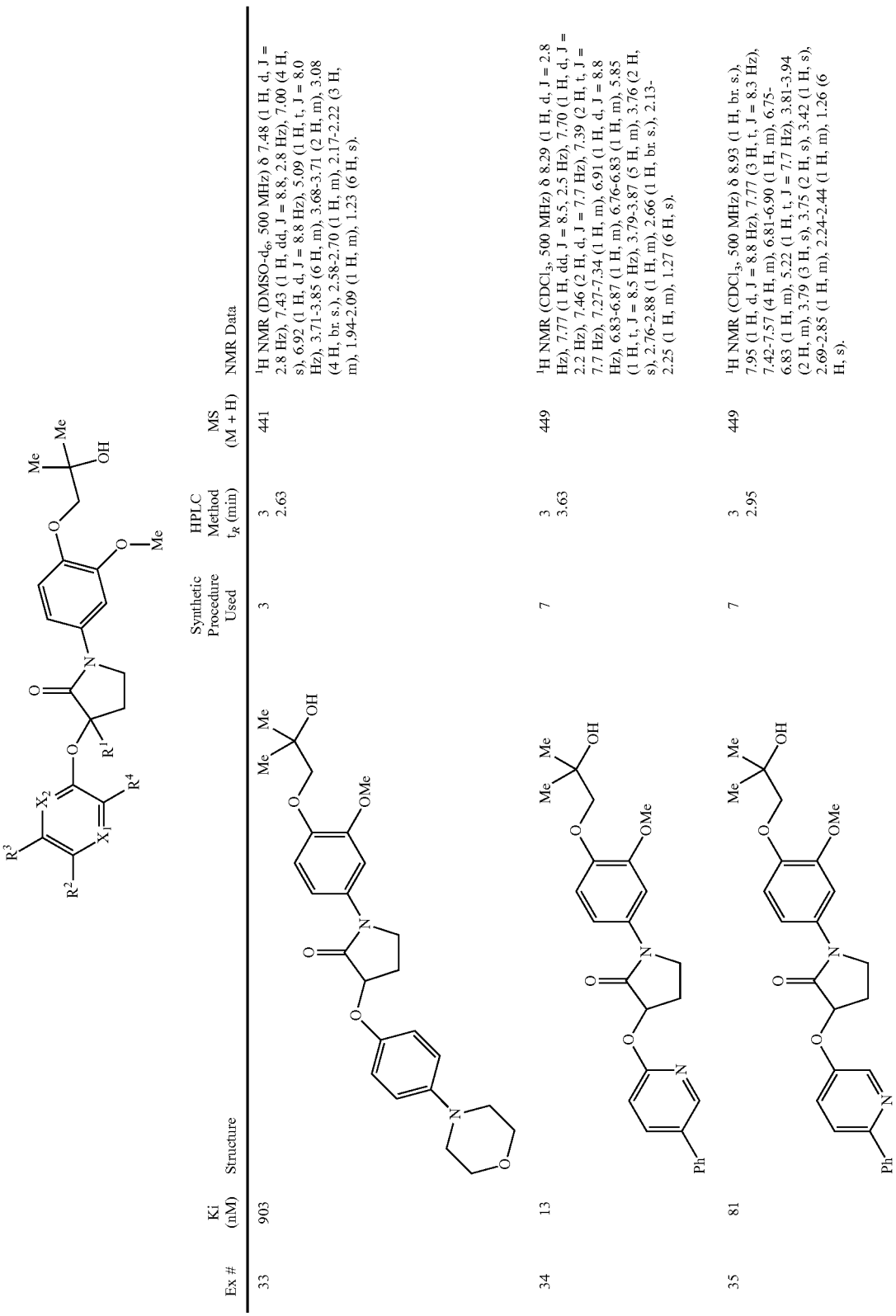
| Ex # | Ki (nM) | Structure | Synthetic Procedure Used | HPLC Method $t_R$ (min) | MS (M + H) | NMR Data |
|---|---|---|---|---|---|---|
| 33 | 903 | 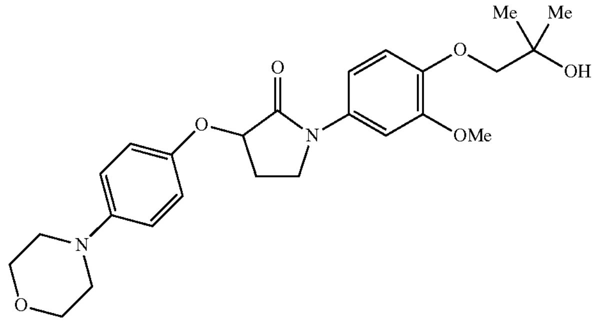 [SMILES: COc1cc(N2CCC(Oc3ccc(N4CCOCC4)cc3)C2=O)ccc1OCC(C)(C)O] | 3 | 3, 2.63 | 441 | $^1$H NMR (DMSO-d$_6$, 500 MHz) δ 7.48 (1 H, d, J = 2.8 Hz), 7.43 (1 H, dd, J = 8.8, 2.8 Hz), 7.00 (4 H, s), 6.92 (1 H, d, J = 8.8 Hz), 5.09 (1 H, t, J = 8.0 Hz), 3.71-3.85 (6 H, m), 3.68-3.71 (2 H, m), 3.08 (4 H, br. s.), 2.58-2.70 (1 H, m), 2.17-2.22 (3 H, m), 1.94-2.09 (1 H, m), 1.23 (6 H, s). |
| 34 | 13 | 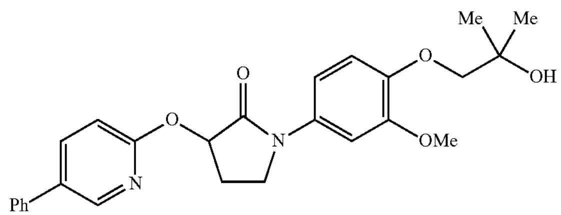 [SMILES: COc1cc(N2CCC(Oc3ccc(-c4ccccc4)cn3)C2=O)ccc1OCC(C)(C)O] | 7 | 3, 3.63 | 449 | $^1$H NMR (CDCl$_3$, 500 MHz) δ 8.29 (1 H, d, J = 2.8 Hz), 7.77 (1 H, dd, J = 8.5, 2.5 Hz), 7.70 (1 H, d, J = 2.2 Hz), 7.46 (2 H, d, J = 7.7 Hz), 7.39 (2 H, t, J = 7.7 Hz), 7.27-7.34 (1 H, m), 6.91 (1 H, d, J = 8.8 Hz), 6.83-6.87 (1 H, m), 6.76-6.83 (1 H, m), 5.85 (1 H, t, J = 8.5 Hz), 3.79-3.87 (5 H, m), 3.76 (2 H, s), 2.76-2.88 (1 H, m), 2.66 (1 H, br. s.), 2.13-2.25 (1 H, m), 1.27 (6 H, s). |
| 35 | 81 | 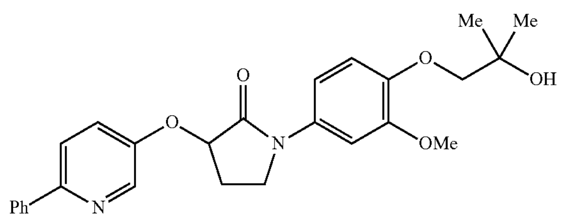 [SMILES: COc1cc(N2CCC(Oc3ccc(-c4ccccc4)nc3)C2=O)ccc1OCC(C)(C)O] | 7 | 3, 2.95 | 449 | $^1$H NMR (CDCl$_3$, 500 MHz) δ 8.93 (1 H, br. s.), 7.95 (1 H, d, J = 8.8 Hz), 7.77 (3 H, t, J = 8.3 Hz), 7.42-7.57 (4 H, m), 6.81-6.90 (1 H, m), 6.75-6.83 (1 H, m), 5.22 (1 H, t, J = 7.7 Hz), 3.81-3.94 (2 H, m), 3.79 (3 H, s), 3.75 (2 H, s), 3.42 (1 H, s), 2.69-2.85 (1 H, m), 2.24-2.44 (1 H, m), 1.26 (6 H, s). |

TABLE A-continued
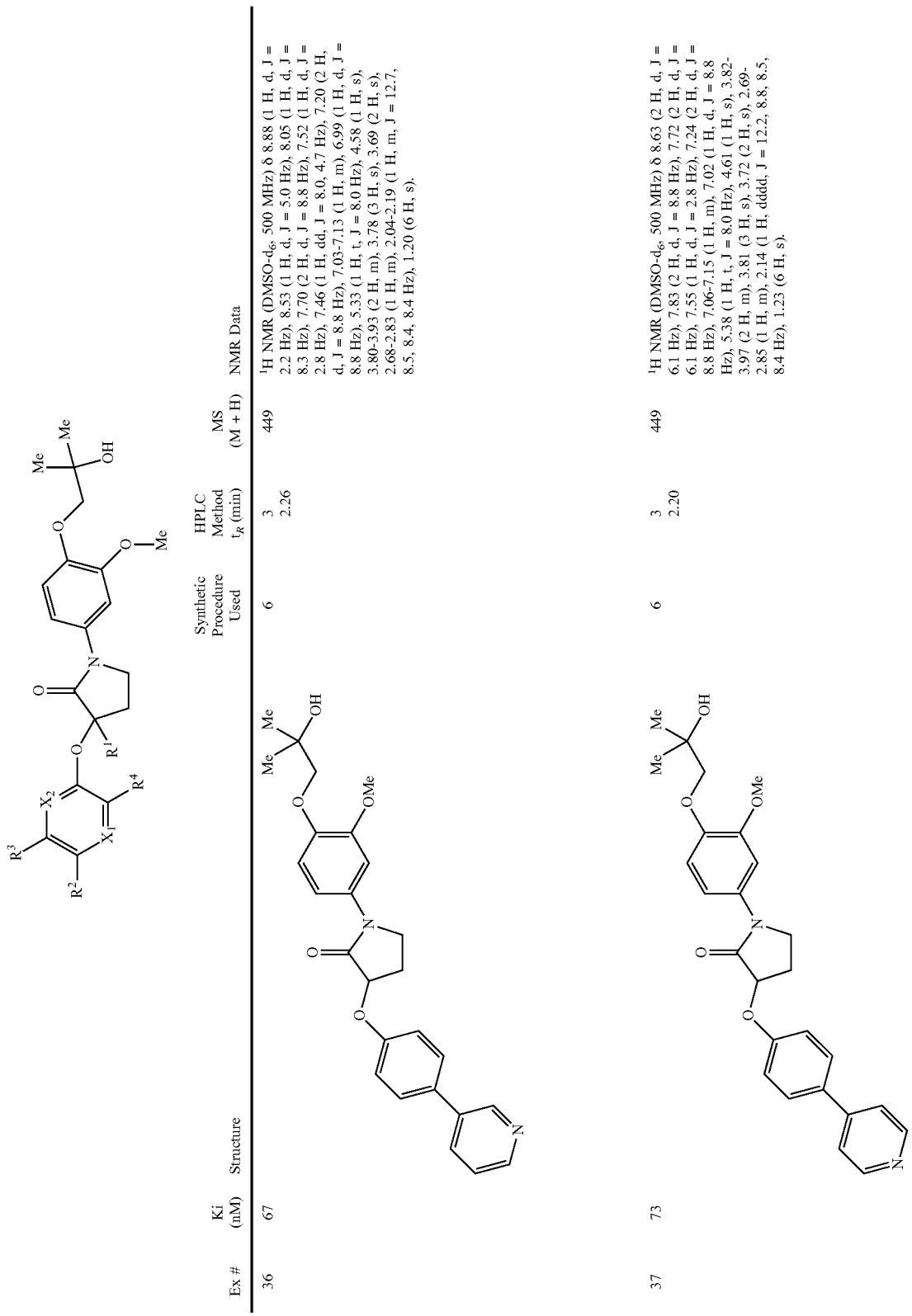
| Ex # | Ki (nM) | Structure | Synthetic Procedure Used | HPLC Method $t_R$ (min) | MS (M + H) | NMR Data |
|---|---|---|---|---|---|---|
| 36 | 67 | 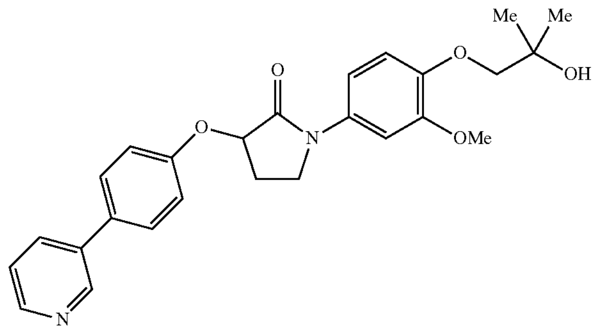 [SMILES: COc1cc(N2CCC(Oc3ccc(-c4cccnc4)cc3)C2=O)ccc1OCC(C)(C)O] | 6 | 3 2.26 | 449 | $^1$H NMR (DMSO-d$_6$, 500 MHz) δ 8.88 (1 H, d, J = 2.2 Hz), 8.53 (1 H, d, J = 5.0 Hz), 8.05 (1 H, d, J = 8.3 Hz), 7.70 (2 H, d, J = 8.8 Hz), 7.52 (1 H, d, J = 2.8 Hz), 7.46 (1 H, dd, J = 8.0, 4.7 Hz), 7.20 (2 H, d, J = 8.8 Hz), 7.03-7.13 (1 H, m), 6.99 (1 H, d, J = 8.8 Hz), 5.33 (1 H, t, J = 8.0 Hz), 4.58 (1 H, s), 3.80-3.93 (2 H, m), 3.78 (3 H, s), 3.69 (2 H, s), 2.68-2.83 (1 H, m), 2.04-2.19 (1 H, m, J = 12.7, 8.5, 8.4, 8.4 Hz), 1.20 (6 H, s). |
| 37 | 73 | 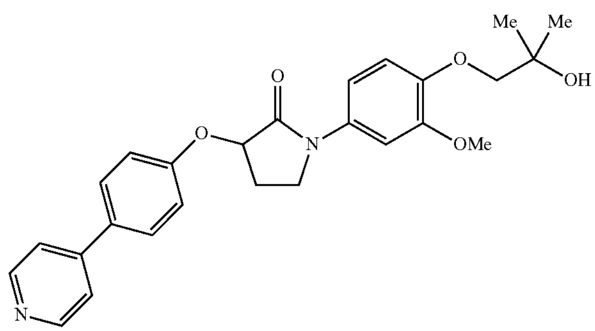 [SMILES: COc1cc(N2CCC(Oc3ccc(-c4ccncc4)cc3)C2=O)ccc1OCC(C)(C)O] | 6 | 3 2.20 | 449 | $^1$H NMR (DMSO-d$_6$, 500 MHz) δ 8.63 (2 H, d, J = 6.1 Hz), 7.83 (2 H, d, J = 8.8 Hz), 7.72 (2 H, d, J = 6.1 Hz), 7.55 (1 H, d, J = 2.8 Hz), 7.24 (2 H, d, J = 8.8 Hz), 7.06-7.15 (1 H, m), 7.02 (1 H, d, J = 8.8 Hz), 5.38 (1 H, t, J = 8.0 Hz), 4.61 (1 H, s), 3.82-3.97 (2 H, m), 3.81 (3 H, s), 3.72 (2 H, s), 2.69-2.85 (1 H, m), 2.14 (1 H, dddd, J = 12.2, 8.8, 8.5, 8.4 Hz), 1.23 (6 H, s). |

TABLE A-continued

| Ex # | Ki (nM) | Structure | Synthetic Procedure Used | HPLC Method $t_R$ (min) | MS (M + H) | NMR Data |
|---|---|---|---|---|---|---|
| 38 | 5 | (structure: pyrrolyl-phenyl) | 3 | 2 / 3.45 | 437 | $^1$H NMR (CDCl$_3$, 500 MHz) δ 7.68 (1 H, d, J = 2.2 Hz), 7.28-7.32 (2 H, m), 7.10-7.16 (2 H, m), 6.99 (2 H, t, J = 2.2 Hz), 6.87-6.92 (1 H, m), 6.81-6.85 (1 H, m), 6.28-6.33 (2 H, m), 5.02 (1 H, t, J = 7.7 Hz), 3.87-3.93 (1 H, m), 3.86 (3 H, s), 3.81-3.85 (1 H, m), 3.80 (2 H, s), 2.63-2.74 (1 H, m), 2.26-2.37 (1 H, m), 2.16 (1 H, br. s.), 1.32 (6 H, s). |
| 39 | 480 | (structure: imidazolyl-phenyl) | 3 | 3 / 2.05 | 438 | $^1$H NMR (CDCl$_3$, 500 MHz) δ 8.95 (1 H, s), 7.52-7.62 (2 H, m), 7.39-7.46 (3 H, m), 7.27 (2 H, d, J = 8.8 Hz), 6.88-6.92 (1 H, m), 6.83-6.88 (1 H, m). |
| 40 | 84 | (structure: azetidinyl-phenyl) | 7 | 3 / 2.32 | 411 | $^1$H NMR (DMSO-d$_6$, 500 MHz) δ 7.46 (1 H, s), 7.41 (1 H, dd, J = 8.8, 2.2 Hz), 6.85-6.97 (3 H, m), 6.27-6.48 (2 H, m), 4.96 (1 H, t, J = 7.7 Hz), 4.62 (1 H, s), 3.65-3.83 (8 H, m), 2.54-2.67 (1 H, m), 2.24 (2 H, quin, J = 7.2 Hz), 2.19 (3 H, s), 1.94-2.08 (1 H, m), 1.22 (6 H, s). |

TABLE A-continued

| Ex # | Ki (nM) | Structure | Synthetic Procedure Used | HPLC Method $t_R$ (min) | MS (M + H) | NMR Data |
|---|---|---|---|---|---|---|
| 41 | 522 | (structure: 3-(4-bromo-3-chlorophenoxy)-1-[4-(2-hydroxy-2-methylpropoxy)-3-methoxyphenyl]pyrrolidin-2-one) | 3 | 3, 3.69 | 486 | $^1$H NMR (DMSO-d$_6$, 500 MHz) δ 7.67 (1 H, d, J = 8.8 Hz), 7.48 (1 H, d, J = 2.2 Hz), 7.41 (1 H, d, J = 2.8 Hz), 7.04 (2 H, td, J = 8.9, 2.5 Hz), 6.94-7.01 (1 H, m), 5.34 (1 H, t, J = 8.3 Hz), 4.57 (1 H, s), 3.78-3.89 (2 H, m), 3.77 (3 H, s), 3.68 (2 H, s), 2.62-2.75 (1 H, m), 2.02-2.19 (1 H, m, J = 12.7, 8.8, 8.5, 8.5 Hz), 1.20 (6 H, s). |
| 42 | 821 | (structure: 3-(4-bromo-3-fluorophenoxy)-1-[4-(2-hydroxy-2-methylpropoxy)-3-methoxyphenyl]pyrrolidin-2-one) | 3 | 3, 3.54 | 471 | $^1$H NMR (DMSO-d$_6$, 500 MHz) δ 7.60 (1 H, t, J = 8.5 Hz), 7.47 (1 H, d, J = 2.2 Hz), 7.19 (1 H, dd, J = 10.7, 2.5 Hz), 7.00-7.07 (1 H, m), 6.95-6.99 (1 H, m), 6.91 (1 H, dd, J = 8.8, 2.8 Hz), 5.30 (1 H, t, J = 8.0 Hz), 4.56 (1 H, s), 3.77-3.89 (2 H, m), 3.76 (3 H, s), 3.67 (2 H, s), 2.64-2.75 (1 H, m), 2.00-2.14 (1 H, m, J = 12.7, 8.8, 8.5, 8.5 Hz), 1.19 (6 H, s). |

TABLE B

| Ex. # | Ki (nM) | Structure | Synthetic Procedure Used | HPLC Method $t_R$ (min) | MS (M + H) | NMR Data |
|---|---|---|---|---|---|---|
| 43 | 19 | (structure: 3-(4-phenylphenoxy)-1-(3,4-dimethoxyphenyl)pyrrolidin-2-one) | 1 | 2, 3.62 | 390 | $^1$H NMR (CDCl$_3$, 500 MHz) δ 7.70 (1 H, s), 7.48-7.57 (4 H, m), 7.40 (2 H, t, J = 7.4 Hz), 7.27-7.33 (1 H, m), 7.14 (2 H, d, J = 8.8 Hz), 6.85 (2 H, s), 5.07 (1 H, t, J = 7.7 Hz), 3.81-3.94 (7 H, m), 2.64-2.78 (1 H, m), 2.21-2.38 (1 H, m). |
| 44 | 4 | (structure with (S)-2-hydroxy-2-cyclopropylethoxy group) | 2 | 3, 3.71 | 460 | $^1$H NMR (DMSO-d$_6$, 500 MHz) δ 7.56-7.66 (4 H, m), 7.51 (1 H, d, J = 2.8 Hz), 7.43 (2 H, t, J = 7.7 Hz), 7.31 (1 H, t, J = 7.4 Hz), 7.15 (2 H, d, J = 8.8 Hz), 7.02-7.08 (1 H, m), 6.94-7.02 (1 H, m), 5.28 (1 H, t, J = 8.0 Hz), 4.82 (1 H, d, J = 5.0 Hz), 3.77-3.95 (4 H, m), 3.76 (3 H, s), 3.26-3.36 (1 H, m), 2.67-2.79 (1 H, m), 2.03-2.17 (1 H, m, J = 12.7, 8.5, 8.4, 8.4 Hz), 0.85-0.96 (1 H, m), 0.34-0.43 (2 H, m), 0.20-0.33 (2 H, m). |
| 45 | 1057 | (structure with (R)-2-hydroxy-2-cyclopropylethoxy group) | 2 | 3, 3.75 | 460 | $^1$H NMR (DMSO-d$_6$, 500 MHz) δ 7.57-7.65 (4 H, m), 7.51 (1 H, d, J = 2.8 Hz), 7.43 (2 H, t, J = 8.0 Hz), 7.31 (1 H, t, J = 7.4 Hz), 7.15 (2 H, d, J = 8.8 Hz), 7.03-7.09 (1 H, m), 6.97-7.02 (1 H, m), 5.29 (1 H, t, J = 8.0 Hz), 4.82 (1 H, d, J = 5.5 Hz), 3.78-3.97 (4 H, m), 3.76 (3 H, s), 3.20-3.44 (1 H, m), 2.64-2.81 (1 H, m), 2.10 (1 H, m, J = 12.4, 8.5 Hz), 0.86-1.01 (1 H, m), 0.33-0.44 (2 H, m), 0.19-0.32 (2 H, m). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 46 | 12 | (structure) | 1 | 2 3.59 | 424 | $^1$H NMR (CDCl$_3$, 500 MHz) δ 7.70 (1 H, d, J = 2.2 Hz), 6.94-7.02 (4 H, m), 6.92 (1 H, d, J = 8.8 Hz), 6.79-6.85 (1 H, m), 4.96 (1 H, t, J = 7.7 Hz), 4.14 (1 H, dd, J = 9.9, 2.7 Hz), 3.95 (1 H, t, J = 9.1 Hz), 3.76-3.90 (4 H, m), 3.28 (1 H, td, J = 8.4, 2.5 Hz), 2.59-2.69 (1 H, m), 2.20-2.31 (1 H, m), 1.77-1.95 (3 H, m), 0.84-0.96 (3 H, m), 0.54-0.63 (3 H, m), 0.47-0.54 (1 H, m), 0.38-0.46 (1 H, m), 0.21-0.30 (1 H, m, J = 9.5, 4.9, 4.8 Hz). |
| 47 | 7 | (structure) | 1 | 3 3.77 | 496 | $^1$H NMR (DMSO-d$_6$, 500 MHz) δ 7.59-7.66 (4 H, m), 7.54 (1 H, d, J = 2.2 Hz), 7.39-7.47 (2 H, m), 7.32 (1 H, t, J = 7.4 Hz), 7.16 (2 H, d, J = 8.8 Hz), 6.99-7.12 (2 H, m), 5.79 (1 H, s), 5.30 (1 H, t, J = 8.0 Hz), 3.92 (2 H, s), 3.80-3.91 (2 H, m), 3.79 (3 H, s), 2.79-2.93 (2 H, m), 2.66-2.79 (1 H, m), 2.53-2.65 (2 H, m), 2.11 (1 H, dddd, J = 12.8, 8.8, 8.5, 8.4 Hz). |
| 48 | 5 | (structure) | 8 | 4 10.09 | 526 | $^1$H NMR (CDCl$_3$, 400 MHz) δ 7.83 (1 H, t, J = 2.42 Hz), 7.52-7.58 (4 H, m), 7.40-7.46 (2 H, m), 7.32 (1 H, t, J = 7.37 7.37 Hz), 7.15-7.20 (2 H, m), 6.97 (1 H, d, J = 8.58 Hz), 6.85 (1 H, dd, J = 8.69, 2.53 Hz), 5.10 (1 H, t, J = 7.59 Hz), 4.53-4.62 (1 H, m), 4.04-4.12 (2 H, m), 3.83-3.98 (5 H, m), 3.49 (1 H, br. s.), 3.29-3.36 (1 H, m), 3.15-3.26 (3 H, m), 2.68-2.79 (1 H, m), 2.31-2.42 (1 H, m), 1.45 (3 H, t, J = 7.48 Hz). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 49 | 6 | 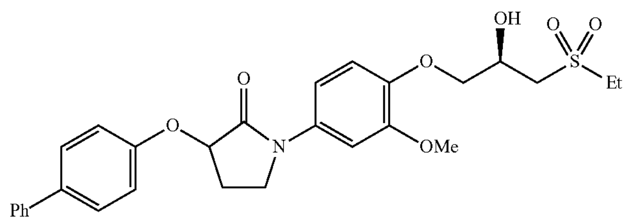 [SMILES: CCS(=O)(=O)C[C@H](O)COc1ccc(N2CCC(Oc3ccc(-c4ccccc4)cc3)C2=O)cc1OC] | 8 | 4 10.05 | 526 | $^1$H NMR (CDCl$_3$, 400 MHz) δ 7.82 (1 H, t, J = 2.42 Hz), 7.52-7.59 (4 H, m), 7.40-7.46 (2 H, m), 7.29-7.36 (1 H, m), 7.14-7.20 (2 H, m), 6.97 (1 H, d, J = 8.80 Hz), 6.85 (1 H, dd, J = 8.69, 2.53 Hz), 5.10 (1 H, t, J = 7.70 Hz), 4.53-4.62 (1 H, m), 4.06-4.12 (2 H, m), 3.82-3.97 (5 H, m), 3.28-3.37 (1 H, m), 3.13-3.26 (3 H, m), 2.69-2.79 (1 H, m, J = 13.23, 7.47, 7.47, 3.52 Hz), 2.31-2.42 (1 H, m), 1.45 (3 H, t, J = 7.48 Hz). |
| 50 | 197 | 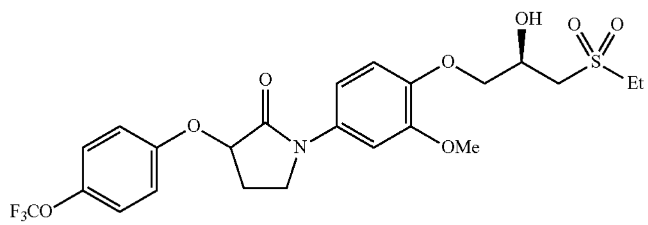 [SMILES: CCS(=O)(=O)C[C@H](O)COc1ccc(N2CCC(Oc3ccc(OC(F)(F)F)cc3)C2=O)cc1OC] | 1 | 4 9.69 | 534 | $^1$H NMR (CDCl$_3$, 400 MHz) δ 7.76 (1 H, t, J = 2.09 Hz), 7.15 (2 H, d, J = 0.44 Hz), 7.07-7.13 (2 H, m), 6.95 (1 H, d, J = 8.80 Hz), 6.82 (1 H, dd, J = 8.58, 2.42 Hz), 5.01 (1 H, t, J = 7.70 Hz), 4.52-4.60 (1 H, m), 4.06 (2 H, dd, J = 5.28, 2.20 Hz), 3.88 (3 H, s), 3.80-3.97 (2 H, m), 3.26-3.35 (1 H, m), 3.12-3.25 (3 H, m), 2.69 (1 H, dddd, J = 13.20, 7.54, 7.43, 3.30 Hz), 2.26-2.39 (1 H, m), 1.89 (1 H, br. s.), 1.43 (3 H, t, J = 7.48 Hz). |
| 51 | 78 | 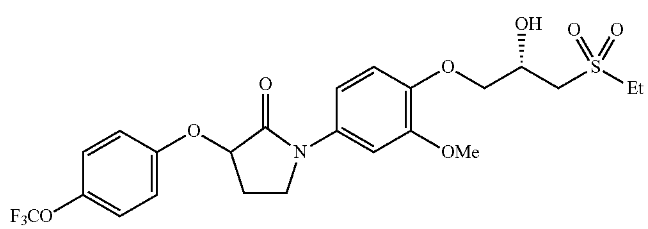 [SMILES: CCS(=O)(=O)C[C@@H](O)COc1ccc(N2CCC(Oc3ccc(OC(F)(F)F)cc3)C2=O)cc1OC] | 1 | 4 9.71 | 534 | $^1$H NMR (CDCl$_3$, 400 MHz) δ 7.78 (1 H, t, J = 2.20 Hz), 7.09-7.22 (4 H, m), 6.96 (1 H, d, J = 8.58 Hz), 6.83 (1 H, dd, J = 8.58, 2.42 Hz), 5.02 (1 H, t, J = 7.70 Hz), 4.54-4.62 (1 H, m), 4.02-4.13 (2 H, m), 3.81-3.98 (5 H, m), 3.28-3.37 (1 H, m), 3.13-3.26 (3 H, m), 2.64-2.77 (1 H, m, J = 13.18, 7.55, 7.55, 3.41 Hz), 2.27-2.41 (1 H, m), 1.39-1.50 (3 H, m). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 52 | 16 | 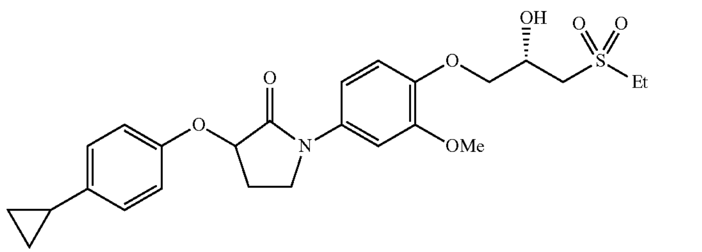 [SMILES: CCS(=O)(=O)C[C@@H](O)COc1ccc(N2CCC(Oc3ccc(C4CC4)cc3)C2=O)cc1OC] | 1 | 4 9.41 | 490 | $^1$H NMR (CDCl$_3$, 400 MHz) δ 7.79 (1 H, t, J = 2.31 Hz), 7.00 (5 H, d, J = 10.56 Hz), 6.82 (1 H, dd, J = 8.69, 2.53 Hz), 4.98 (1 H, t, J = 7.70 Hz), 4.46-4.65 (1 H, m), 4.01-4.11 (2 H, m), 3.88 (3 H, s), 3.77-3.95 (2 H, m), 3.31 (1 H, dd, J = 14.75, 9.02 Hz), 3.12-3.25 (3 H, m), 2.58-2.75 (1 H, m), 2.22-2.35 (1 H, m), 1.82-1.90 (1 H, m), 1.44 (3 H, t, J = 7.48 Hz), 0.86-0.95 (2 H, m), 0.58-0.66 (2 H, m). |
| 53 | 109 | 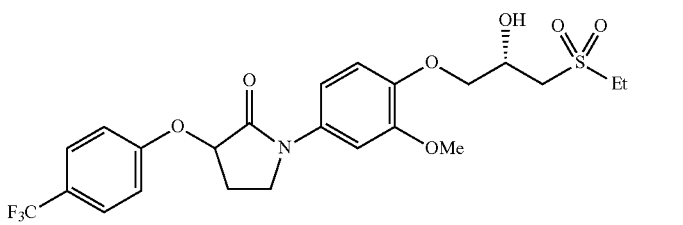 [SMILES: CCS(=O)(=O)C[C@@H](O)COc1ccc(N2CCC(Oc3ccc(C(F)(F)F)cc3)C2=O)cc1OC] | 1 | 4 9.51 | 518 | $^1$H NMR (CDCl$_3$, 400 MHz) δ 7.75 (1 H, t, J = 2.09 Hz), 7.57 (2 H, d, J = 8.58 Hz), 7.17 (2 H, d, J = 8.36 Hz), 6.95 (1 H, d, J = 8.80 Hz), 6.83 (1 H, dd, J = 8.58, 2.42 Hz), 5.11 (1 H, t, J = 7.70 Hz), 4.57 (1 H, dddd, J = 8.83, 5.97, 4.79, 2.86 Hz), 4.00-4.13 (2 H, m), 3.88 (3 H, s), 3.83-3.98 (2 H, m), 3.26-3.38 (1 H, m), 3.12-3.25 (2 H, m), 2.72 (1 H, dddd, J = 13.29, 7.57, 7.43, 3.41 Hz), 2.29-2.40 (1 H, m), 1.43 (3 H, t, J = 7.48 Hz). |
| 54 | 21 | 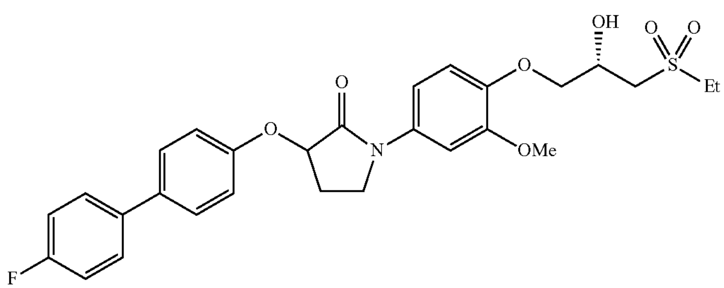 [SMILES: CCS(=O)(=O)C[C@@H](O)COc1ccc(N2CCC(Oc3ccc(-c4ccc(F)cc4)cc3)C2=O)cc1OC] | 1 | 4 10.19 | 544 | $^1$H NMR (CDCl$_3$, 400 MHz) δ 7.81 (1 H, t, J = 2.20 Hz), 7.43-7.54 (4 H, m), 7.07-7.19 (4 H, m), 6.96 (1 H, d, J = 8.80 Hz), 6.85 (1 H, dd, J = 8.58, 2.42 Hz), 5.10 (1 H, t, J = 7.59 Hz), 4.52-4.62 (1 H, m), 4.03-4.13 (2 H, m), 3.82-3.98 (5 H, m), 3.27-3.38 (1 H, m), 3.11-3.27 (3 H, m), 2.73 (1 H, dddd, J = 13.20, 7.48, 7.37, 3.41 Hz), 2.29-2.45 (1 H, m), 1.41-1.50 (3 H, m). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 55 | 38 | 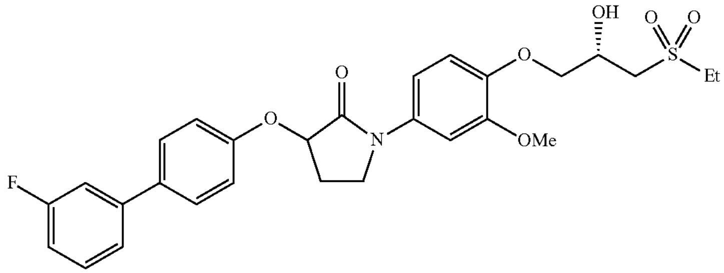 [SMILES: CCS(=O)(=O)C[C@@H](O)COc1ccc(N2CCC(Oc3ccc(-c4cccc(F)c4)cc3)C2=O)cc1OC] | 6 | 4 10.29 | 544 | $^1$H NMR (CDCl$_3$, 400 MHz) δ 7.80 (1 H, t, J = 2.31 Hz), 7.49-7.56 (2 H, m), 7.30-7.42 (2 H, m), 7.21-7.26 (1 H, m), 7.13-7.20 (2 H, m), 6.93-7.05 (2 H, m), 6.84 (1 H, dd, J = 8.58, 2.42 Hz), 5.10 (1 H, t, J = 7.70 Hz), 4.52-4.61 (1 H, m), 4.01-4.14 (2 H, m), 3.89 (3 H, s), 3.83-3.98 (2 H, m), 3.26-3.39 (1 H, m), 3.09-3.25 (3 H, m), 2.73 (1 H, dddd, J = 13.18, 7.50, 7.50, 3.52 Hz), 2.30-2.42 (1 H, m), 1.44 (3 H, t, J = 7.48 Hz). |
| 56 | 71 | 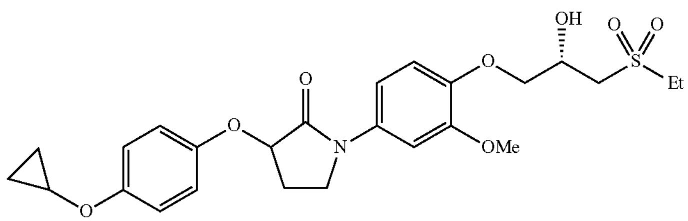 [SMILES: CCS(=O)(=O)C[C@@H](O)COc1ccc(N2CCC(Oc3ccc(OC4CC4)cc3)C2=O)cc1OC] | 1 | 4 8.99 | 506 | $^1$H NMR (CDCl$_3$, 400 MHz) δ 7.80 (1 H, t, J = 2.31 Hz), 6.93-7.07 (5 H, m), 6.83 (1 H, dd, J = 8.80, 2.42 Hz), 4.94 (1 H, t, J = 7.70 Hz), 4.53-4.61 (1 H, m), 4.03-4.11 (2 H, m), 3.87-3.94 (4 H, m), 3.79-3.87 (1 H, m), 3.67-3.73 (1 H, m), 3.28-3.36 (1 H, m), 3.14-3.26 (3 H, m), 2.61-2.72 (1 H, m), 2.25-2.36 (1 H, m), 1.42-1.47 (3 H, m), 0.74-0.78 (4 H, m). |
| 57 | 2 | 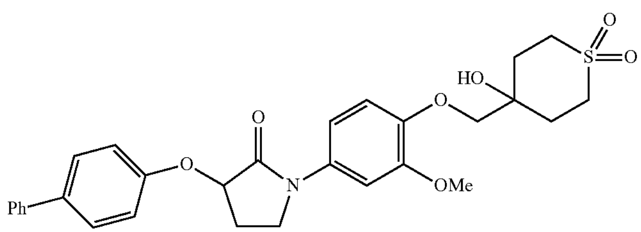 [SMILES: COc1cc(N2CCC(Oc3ccc(-c4ccccc4)cc3)C2=O)ccc1OCC1(O)CCS(=O)(=O)CC1] | 1 | 2 3.47 | 538 | $^1$H NMR (CDCl$_3$, 500 MHz) δ 7.79 (1 H, s), 7.53 (4 H, dd, J = 7.7, 5.5 Hz), 7.40 (2 H, t, J = 7.7 Hz), 7.26-7.33 (1 H, m), 7.14 (2 H, d, J = 8.8 Hz), 6.91 (1 H, d, J = 8.2 Hz), 6.79-6.84 (2 H, m), 5.07 (1 H, t, J = 7.4 Hz), 3.88-3.94 (2 H, m), 3.86 (3 H, s), 3.85 (2 H, s), 3.41-3.53 (2 H, m), 2.92 (2 H, d, J = 12.1 Hz), 2.66-2.76 (1 H, m), 2.29-2.38 (1 H, m), 2.22-2.29 (2 H, m), 2.11-2.22 (2 H, m), 1.77 (1 H, d, J = 2.7 Hz). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 58 | 9 | 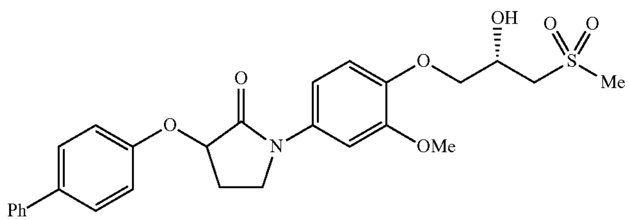 [SMILES: COc1cc(N2CCC(Oc3ccc(-c4ccccc4)cc3)C2=O)ccc1OC[C@H](O)CS(C)(=O)=O] | 9 | 4, 9.88 | 512 | $^1$H NMR (CDCl$_3$, 400 MHz) δ 7.82 (1 H, t, J = 2.42 Hz), 7.50-7.59 (4 H, m), 7.42 (2 H, t, J = 7.59 Hz), 7.28-7.35 (1 H, m), 7.12-7.19 (2 H, m), 6.93-7.01 (1 H, m), 6.84 (1 H, dd, J = 8.69, 2.53 Hz), 5.09 (1 H, t, J = 7.70 Hz), 4.51-4.62 (1 H, m), 4.01-4.11 (2 H, m), 3.89 (3 H, s), 3.82-3.98 (2 H, m), 3.30-3.39 (1 H, m), 3.17-3.25 (1 H, m), 3.06-3.12 (3 H, m), 2.73 (1 H, dddd, J = 13.18, 7.50, 7.50, 3.52 Hz), 2.29-2.41 (1 H, m). |
| 59 | 18 | 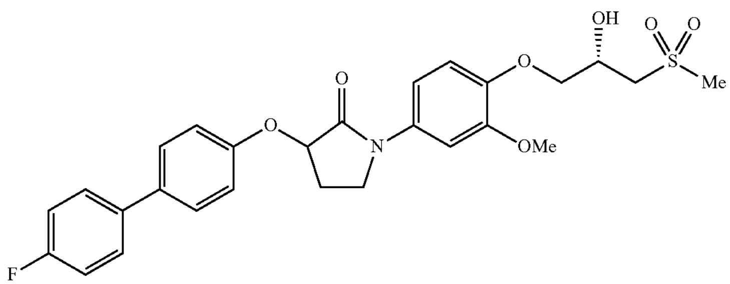 [SMILES: COc1cc(N2CCC(Oc3ccc(-c4ccc(F)cc4)cc3)C2=O)ccc1OC[C@H](O)CS(C)(=O)=O] | 9 | 4, 9.96 | 530 | $^1$H NMR (CDCl$_3$, 400 MHz) δ 7.81 (1 H, t, J = 2.31 Hz), 7.44-7.53 (4 H, m), 7.15 (2 H, d, J = 8.80 Hz), 7.10 (2 H, t, J = 8.80 Hz), 6.96 (1 H, d, J = 8.80 Hz), 6.84 (1 H, dd, J = 8.58, 2.42 Hz), 5.09 (1 H, t, J = 7.59 Hz), 4.49-4.63 (1 H, m), 4.00-4.14 (2 H, m), 3.89 (3 H, s), 3.82-3.98 (3 H, m), 3.44-3.55 (1 H, m), 3.34 (1 H, dd, J = 14.75, 9.24 Hz), 3.17-3.25 (1 H, m), 3.08 (3 H, s). |
| 60 | 17 | 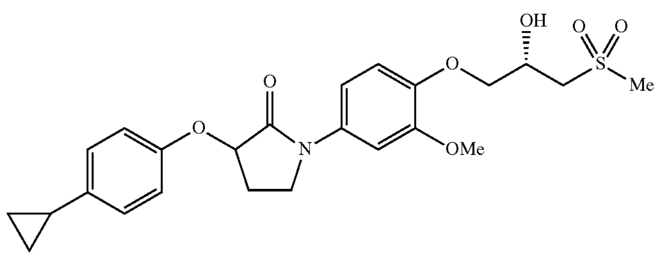 | 9 | 4, 9.18 | 476 | $^1$H NMR (CDCl$_3$, 400 MHz) δ 7.79 (1 H, t, J = 2.31 Hz), 7.00-7.05 (2 H, m, J = 9.02 Hz), 6.97 (2 H, d, J = 9.02 Hz), 6.94 (1 H, d, J = 8.80 Hz), 6.82 (1 H, dd, J = 8.69, 2.53 Hz), 4.99 (1 H, t, J = 7.59 Hz), 4.56 (1 H, dddd, J = 9.05, 6.52, 4.24, 2.64 Hz), 3.99-4.10 (2 H, m), 3.88 (3 H, s), 3.77-3.95 (2 H, m), 3.34 (1 H, dd, J = 14.75, 9.24 Hz), 3.17-3.24 (1 H, m), 3.08 (3 H, s), 2.67 (1 H, dddd, J = 13.23, 7.41, 7.41, 3.41 Hz), 2.29 (1 H, m), 1.82-1.90 (1 H, m), 0.86-0.94 (2 H, m), 0.59-0.65 (2 H, m). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 61 | 65 | (structure with F$_3$CO-phenyl and methylsulfonyl-methoxyphenyl groups) | 9 | 4 9.49 | 520 | $^1$H NMR (CDCl$_3$, 400 MHz) δ 7.77 (1 H, t, J = 2.20 Hz), 7.16 (2 H, d, J = 8.80 Hz), 7.07-7.13 (2 H, m), 6.95 (1 H, d, J = 8.58 Hz), 6.83 (1 H, dd, J = 8.80, 2.42 Hz), 5.01 (1 H, t, J = 7.59 Hz), 4.49-4.63 (1 H, m), 3.99-4.12 (2 H, m), 3.88 (3 H, s), 3.81-3.96 (2 H, m), 3.34 (1 H, dd, J = 14.75, 9.24 Hz), 3.21 (1 H, dd, J = 14.75, 1.54 Hz), 3.08 (3 H, s), 2.69 (1 H, dddd, J = 13.26, 7.54, 7.37, 3.30 Hz), 2.27-2.39 (1 H, m). |
| 62 | 11 | (structure with Ph-phenyl and methylsulfonyl-methoxyphenyl groups) | 1 | 4 9.76 | 512 | $^1$H NMR (CDCl$_3$, 400 MHz) δ 7.82 (1 H, t, J = 2.42 Hz), 7.51-7.59 (4 H, m), 7.42 (2 H, t, J = 7.70 Hz), 7.30-7.35 (1 H, m), 7.12-7.20 (2 H, m), 6.96 (1 H, d, J = 8.80 Hz), 6.84 (1 H, dd, J = 8.69, 2.53 Hz), 5.09 (1 H, t, J = 7.59 Hz), 4.57 (1 H, dddd, J = 9.05, 6.46, 4.18, 2.53 Hz), 4.00-4.11 (2 H, m), 3.89 (3 H, s), 3.83-3.97 (2 H, m), 3.34 (1 H, dd, J = 14.75, 9.24 Hz), 3.21 (1 H, ddd, J = 14.75, 2.42, 0.88 Hz), 3.08 (3 H, s), 2.73 (1 H, dddd, J = 13.20, 7.54, 7.43, 3.52 Hz), 2.29-2.41 (1 H, m). |
| 63 | 38 | (structure with 4-fluorobiphenyl and OMe-phenyl groups) | 1 | 4 9.85 | 530 | $^1$H NMR (CDCl$_3$, 400 MHz) δ 7.81 (1 H, t, J = 2.42 Hz), 7.45-7.53 (4 H, m), 7.13-7.18 (2 H, m), 7.06-7.13 (2 H, m), 6.96 (1 H, d, J = 8.58 Hz), 6.84 (1 H, dd, J = 8.69, 2.53 Hz), 5.09 (1 H, t, J = 7.70 Hz), 4.50-4.62 (1 H, m), 4.00-4.13 (2 H, m), 3.89 (3 H, s), 3.82-3.98 (2 H, m), 3.28-3.39 (1 H, m), 3.21 (1 H, ddd, J = 14.75, 2.42, 1.10 Hz), 3.08 (3 H, s), 2.73 (1 H, dddd, J = 13.29, 7.51, 7.37, 3.52 Hz), 2.29-2.41 (1 H, m). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 64 | 32 | (4-cyclopropylphenoxy pyrrolidinone linked to N-phenyl with OMe and OCH2CH(OH)CH2S(O)2Me substituents) | 1 | 4 9.13 | 476 | $^1$H NMR (CDCl$_3$, 400 MHz) δ 7.79 (1 H, t, J = 2.42 Hz), 7.00-7.04 (2 H, m), 6.96-7.00 (2 H, m), 6.95 (1 H, d, J = 8.58 Hz), 6.82 (1 H, dd, J = 8.69, 2.53 Hz), 4.99 (1 H, t, J = 7.59 Hz), 4.56 (1 H, dddd, J = 9.11, 6.52, 4.07, 2.53 Hz), 3.99-4.13 (2 H, m), 3.88 (3 H, s), 3.78-3.94 (2 H, m), 3.34 (1 H, dd, J = 14.53, 9.02 Hz), 3.21 (1 H, dd, J = 14.75, 2.42, 1.10 Hz), 3.08 (3 H, s), 2.67 (1 H, dddd, J = 13.09, 7.48, 7.37, 3.52 Hz), 2.22-2.35 (1 H, m), 1.84-1.90 (1 H, m), 0.87-0.94 (2 H, m), 0.58-0.65 (2 H, m). |
| 65 | 8 | (4-trifluoromethoxyphenoxy pyrrolidinone linked to N-phenyl with OMe and OCH2CH2S(O)2Me substituents) | 10 | 4 10.34 | 490 | $^1$H NMR (CDCl$_3$, 400 MHz) δ 7.78 (1 H, d, J = 2.42 Hz), 7.15-7.21 (2 H, m), 7.08-7.15 (1 H, m), 6.88-6.95 (2 H, m), 6.83 (1 H, dd, J = 8.69, 2.53 Hz), 5.02 (1 H, t, J = 7.59 Hz), 4.40-4.49 (2 H, m), 3.82-3.97 (5 H, m), 3.46 (2 H, t, J = 5.28 Hz), 3.18 (3 H, s), 2.70 (1 H, dddd, J = 13.26, 7.54, 7.37, 3.30 Hz), 2.29-2.40 (1 H, m). |
| 66 | 2 | (biphenyloxy pyrrolidinone linked to N-phenyl with OMe and OCH2CH2S(O)2Me substituents) | 10 | 4 10.70 | 482 | $^1$H NMR (CDCl$_3$, 400 MHz) δ 7.81 (1 H, d, J = 2.42 Hz), 7.50-7.59 (4 H, m), 7.42 (2 H, t, J = 7.59 Hz), 7.28-7.35 (1 H, m), 7.16 (2 H, d, J = 8.80 Hz), 6.91 (1 H, d, J = 8.58 Hz), 6.83 (1 H, dd, J = 8.80, 2.42 Hz), 5.09 (1 H, t, J = 7.59 Hz), 4.44 (2 H, t, J = 5.28 Hz), 3.87 (3 H, s), 3.82-3.97 (2 H, m), 3.45 (2 H, t, J = 5.06 Hz), 3.17 (3 H, s), 2.73 (1 H, dddd, J = 13.20, 7.54, 7.43, 3.52 Hz), 2.30-2.41 (1 H, m). |

TABLE B-continued
| Ex. # | Ki (nM) | Structure | Synthetic Procedure Used | HPLC Method $t_R$ (min) | MS (M + H) | NMR Data |
|---|---|---|---|---|---|---|
| 67 | 6 | 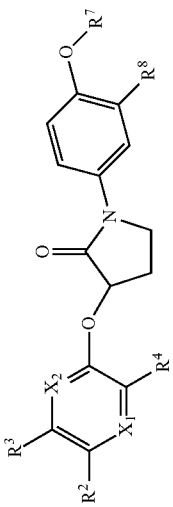 | 11 | 4 10.44 | 500 | $^1$H NMR (CDCl$_3$, 400 MHz) δ 7.82 (1 H, d, J = 2.42 Hz), 7.52 (2 H, dd, J = 8.80, 1.54 Hz), 7.42 (1 H, td, J = 7.81, 1.76 Hz), 7.28-7.33 (1 H, m), 7.10-7.23 (4 H, m), 6.90-6.95 (1 H, m), 6.82-6.86 (1 H, m), 5.11 (1 H, t, J = 7.59 Hz), 4.42-4.48 (2 H, m), 3.84-3.98 (5 H, m), 3.47 (2 H, t, J = 5.17 Hz), 3.19 (3 H, s), 2.74 (1 H, dddd, J = 13.15, 7.48, 7.32, 3.52 Hz), 2.30-2.42 (1 H, m). |
| 68 | 5 | 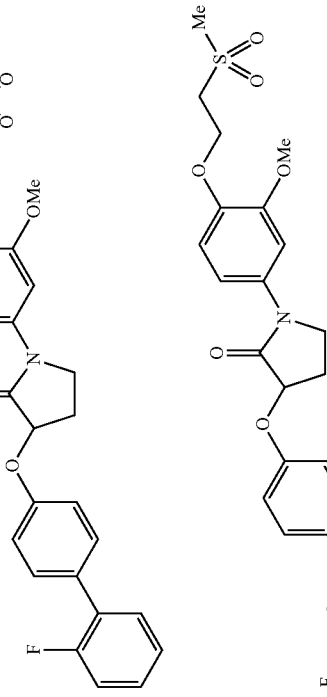 | 11 | 4 10.57 | 500 | $^1$H NMR (CDCl$_3$, 400 MHz) δ 7.81 (1 H, d, J = 2.42 Hz), 7.50-7.57 (2 H, m), 7.30-7.44 (2 H, m), 7.22-7.25 (1 H, m), 7.15-7.20 (2 H, m), 6.98-7.05 (1 H, m), 6.90-6.95 (1 H, m), 6.81-6.87 (1 H, m), 5.11 (1 H, t, J = 7.59 Hz), 4.41-4.49 (2 H, m), 3.83-4.00 (5 H, m), 3.47 (2 H, t, J = 5.06 Hz), 3.18 (3 H, s), 2.68-2.80 (1 H, m, J = 13.26, 7.46, 7.46, 3.52 Hz), 2.29-2.44 (1 H, m). |
| 69 | 5 | 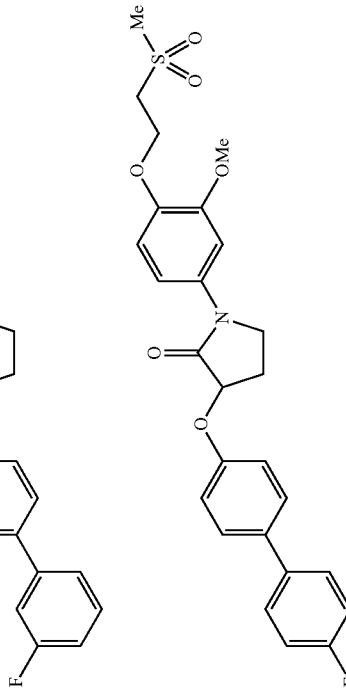 | 1 | 4 10.61 | 500 | $^1$H NMR (CDCl$_3$, 400 MHz) δ 7.81 (1 H, d, J = 2.42 Hz), 7.46-7.58 (4 H, m), 7.05-7.22 (4 H, m), 6.89-6.97 (1 H, m), 6.78-6.89 (1 H, m), 5.09 (1 H, t, J = 7.59 Hz), 4.39-4.49 (2 H, m), 3.90-3.98 (2 H, m), 3.84-3.90 (3 H, m), 3.46 (2 H, t, J = 5.06 Hz), 3.18 (3 H, s), 2.67-2.79 (1 H, m, J = 13.20, 7.48, 7.48, 3.52 Hz), 2.30-2.42 (1 H, m). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 70 | 7 | 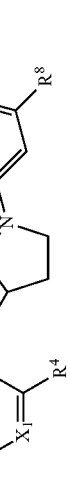 | 1 | 4 9.89 | 446 | $^1$H NMR (CDCl$_3$, 400 MHz) δ 7.80 (1 H, d, J = 2.42 Hz), 6.97-7.07 (4 H, m), 6.87-6.95 (1 H, m), 6.82 (1 H, dd, J = 8.58, 2.42 Hz), 4.99 (1 H, t, J = 7.59 Hz), 4.40-4.48 (2 H, m), 3.78-3.95 (5 H, m), 3.46 (2 H, t, J = 5.06 Hz), 3.18 (3 H, s), 2.62-2.74 (1 H, m, J = 13.26, 7.46, 7.46, 3.52 Hz), 2.24-2.36 (1 H, m), 1.87 (1 H, tt, J = 8.47, 5.06 Hz), 0.85-0.97 (2 H, m), 0.58-0.68 (2 H, m). |
| 71 | 3 | 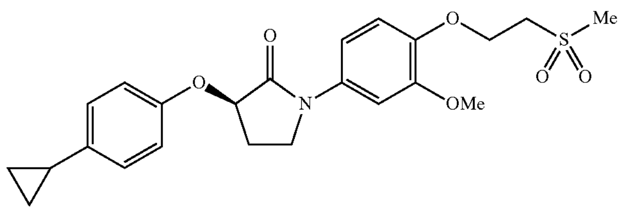 [SMILES: COc1cc(N2CC[C@@H](Oc3ccc(C4CC4)cc3)C2=O)ccc1OCCS(C)(=O)=O] | 12 | 4 9.85 | 446 | $^1$H NMR (CDCl$_3$, 400 MHz) δ 7.80 (1 H, d, J = 2.42 Hz), 6.96-7.06 (4 H, m), 6.88-6.94 (1 H, m), 6.80-6.85 (1 H, m), 4.99 (1 H, t, J = 7.59 Hz), 4.41-4.48 (2 H, m), 3.79-3.94 (5 H, m), 3.46 (2 H, t, J = 5.06 Hz), 3.18 (3 H, s), 2.63-2.73 (1 H, m, J = 13.07, 7.44, 7.44, 3.52 Hz), 2.24-2.35 (1 H, m), 1.82-1.92 (1 H, m, J = 8.42, 8.42, 5.17, 5.06 Hz), 0.88-0.95 (2 H, m), 0.60-0.67 (2 H, m). |
| 72 | 7 | 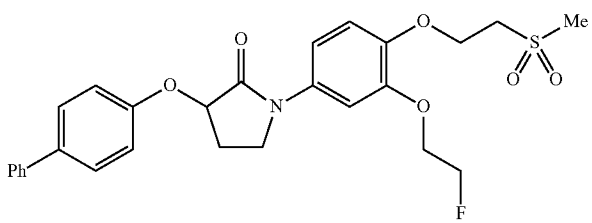 [SMILES: CS(=O)(=O)CCOc1ccc(N2CCC(Oc3ccc(-c4ccccc4)cc3)C2=O)cc1OCCF] | 9 | 4 10.84 | 514 | $^1$H NMR (CDCl$_3$, 400 MHz) δ 7.90 (1 H, d, J = 2.42 Hz), 7.55-7.62 (4 H, m), 7.46 (2 H, t, J = 7.59 Hz), 7.32-7.38 (1 H, m), 7.19 (2 H, dt, J = 8.80, 1.98 Hz), 6.96 (1 H, d, J = 8.80 Hz), 6.88 (1 H, dd, J = 8.80, 2.64 Hz), 5.13 (1 H, t, J = 7.70 Hz), 4.83 (1 H, t, J = 4.07 Hz), 4.71 (1 H, d, J = 3.74 Hz), 4.45-4.50 (2 H, m), 4.33 (1 H, q, J = 3.89 Hz), 4.26 (1 H, q, J = 3.89 Hz), 3.84-4.02 (2 H, m), 3.49 (2 H, t, J = 5.06 Hz), 3.24 (3 H, s), 2.76 (1 H, dddd, J = 13.18, 7.51, 7.37, 3.41 Hz), 2.32-2.46 (1 H, m). |

TABLE B-continued

| Ex. # | Ki (nM) | Structure | Synthetic Procedure Used | HPLC Method $t_R$ (min) | MS (M + H) | NMR Data |
|---|---|---|---|---|---|---|
| 73 | 87 | 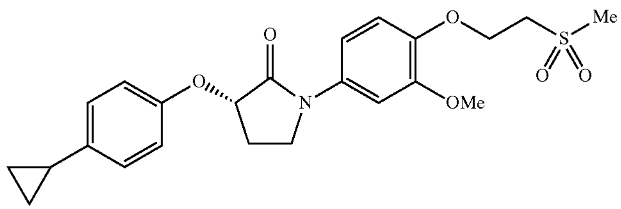 [SMILES: COc1cc(N2CC[C@H](Oc3ccc(C4CC4)cc3)C2=O)ccc1OCCS(C)(=O)=O] | 12 | 4 9.88 | 446 | $^1$H NMR (CDCl$_3$, 400 MHz) δ 7.80 (1 H, d, J = 2.64 Hz), 6.96-7.08 (4 H, m), 6.88-6.94 (1 H, m), 6.79-6.86 (1 H, m), 4.99 (1 H, t, J = 7.59 Hz), 4.40-4.49 (2 H, m), 3.77-3.95 (5 H, m), 3.46 (2 H, t, J = 5.06 Hz), 3.18 (3 H, s), 2.62-2.74 (1 H, m, J = 13.12, 7.47, 7.47, 3.41 Hz), 2.22-2.36 (1 H, m), 1.87 (1 H, tt, J = 8.47, 5.06 Hz), 0.87-0.95 (2 H, m), 0.60-0.67 (2 H, m). |
| 74 | 64 | 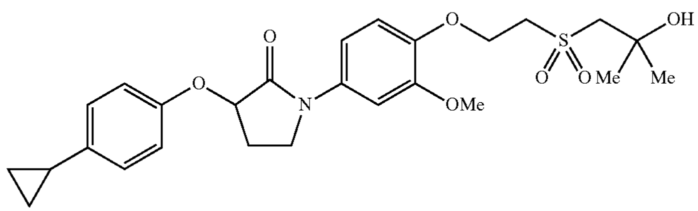 [SMILES: COc1cc(N2CCC(Oc3ccc(C4CC4)cc3)C2=O)ccc1OCCS(=O)(=O)CC(C)(C)O] | 9 | 4 9.93 | 504 | $^1$H NMR (CDCl$_3$, 400 MHz) δ 7.85 (1 H, d, J = 2.20 Hz), 7.00-7.05 (2 H, m), 6.95-7.00 (2 H, m), 6.85 (1 H, d, J = 8.58 Hz), 6.80 (1 H, dd, J = 8.80, 2.42 Hz), 4.99 (1 H, t, J = 7.59 Hz), 4.35-4.49 (2 H, m), 3.88 (3 H, s), 3.78-3.93 (2 H, m), 3.62-3.67 (2 H, m), 3.44 (2 H, s), 2.67 (1 H, dddd, J = 13.18, 7.51, 7.37, 3.41 Hz), 2.23-2.35 (1 H, m), 1.86 (1 H, tt, J = 8.50, 5.03 Hz), 1.47 (6 H, s), 0.86-0.94 (2 H, m), 0.59-0.65 (2 H, m). |
| 75 | 13 | 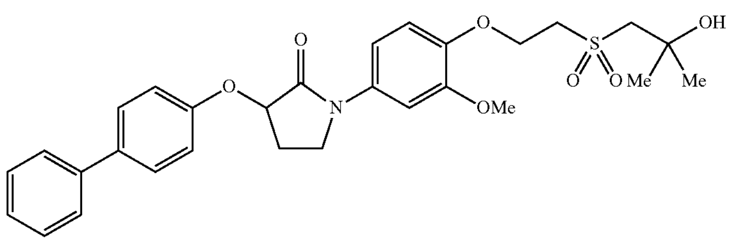 [SMILES: COc1cc(N2CCC(Oc3ccc(-c4ccccc4)cc3)C2=O)ccc1OCCS(=O)(=O)CC(C)(C)O] | 9 | 4 10.57 | 540 | $^1$H NMR (CDCl$_3$, 400 MHz) δ 7.86 (1 H, d, J = 2.20 Hz), 7.50-7.59 (4 H, m), 7.42 (2 H, t, J = 7.70 Hz), 7.28-7.35 (1 H, m), 7.16 (2 H, d, J = 8.80 Hz), 6.87 (1 H, d, J = 8.80 Hz), 6.82 (1 H, dd, J = 8.80, 2.42 Hz), 5.09 (1 H, t, J = 7.70 Hz), 4.39-4.46 (2 H, m), 3.89 (3 H, s), 3.82-3.97 (2 H, m), 3.62-3.68 (2 H, m), 3.44 (2 H, s), 2.73 (1 H, dddd, J = 13.20, 7.48, 7.37, 3.41 Hz), 2.29-2.42 (1 H, m), 1.48 (6 H, s). |

TABLE C

| Ex. # | Ki (nM) | Structure | Synthetic Procedure Used | HPLC Method | $t_R$ (min) | MS (M + H) | NMR Data |
|---|---|---|---|---|---|---|---|
| 76 | 26 | (structure) | 1 | 4 | 11.12 | 424 | $^1$H NMR (CDCl$_3$, 400 MHz) δ 7.57 (2 H, d, J = 8.58 Hz), 7.48 (1 H, d, J = 2.42 Hz), 7.41 (1 H, dd, J = 8.80, 2.64 Hz), 7.18 (2 H, d, J = 8.58 Hz), 6.82 (1 H, d, J = 8.80 Hz), 5.10 (1 H, t, J = 7.48 Hz), 3.83-3.96 (2 H, m), 3.80(2 H, s), 2.67-2.76 (1 H, m, J = 13.18, 7.55, 7.55, 3.63 Hz), 2.30-2.39 (1 H, m), 2.29 (3 H, s), 1.38 (6 H, s). |
| 77 | 15 | (structure) | 3 | 3 | 3.73 | 440 | $^1$H NMR (CDCl$_3$, 400 MHz) δ 7.40 (1 H, d, J = 2.2 Hz), 7.33 (1 H, dd, J = 8.8, 2.8 Hz), 6.99-7.11 (4 H, m), 6.74 (1 H, d, J = 8.8 Hz), 4.93 (1 H, t, J = 7.4 Hz), 3.74-3.90 (2 H, m), 3.72 (2 H, s), 2.50-2.70 (1 H, m), 2.18-2.31 (4 H, m), 2.12 (1 H, s), 1.30 (6 H, s). |
| 78 | 6000 | (structure) | 2 | 3 | 3.73 | 440 | $^1$H NMR (DMSO-d$_6$, 500 MHz) δ 7.48 (1 H, s), 7.43 (1 H, dd, J = 8.8, 2.8 Hz), 7.31 (2 H, d, J = 8.3 Hz), 7.12-7.22 (2 H, m), 6.91 (1 H, d, J = 8.8 Hz), 5.25 (1 H, t, J = 8.0 Hz), 4.63 (1 H, s), 3.74-3.86 (2 H, m), 3.69 (2 H, s), 2.64-2.74 (1 H, m), 2.20 (3 H, s), 2.02-2.14 (1 H, m), 1.23 (6 H, s). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 79 | 11 | (3-(4-(trifluoromethoxy)phenoxy)pyrrolidin-2-one with 4-(2-hydroxy-2-methylpropoxy)-3-methylphenyl on N) | 2 | 3<br>3.72 | 440 | $^1$H NMR (DMSO-d$_6$, 500 MHz) δ 7.48 (1 H, s), 7.43 (1 H, dd, J = 8.8, 2.8 Hz), 7.31 (2 H, d, J = 8.8 Hz), 7.13-7.20 (2 H, m), 6.91 (1 H, d, J = 8.8 Hz), 5.25 (1 H, t, J = 8.0 Hz), 4.60-4.65 (1 H, m), 3.75-3.87 (2 H, m), 3.69 (2 H, s), 2.62-2.74 (1 H, m), 2.20 (3 H, s), 2.02-2.14 (1 H, m), 1.23 (6 H, s). |
| 80 | 4 | (3-(4-phenylphenoxy)pyrrolidin-2-one with 4-(2-hydroxy-2-methylpropoxy)-3-methylphenyl on N) | 3 | 3<br>3.86 | 432 | $^1$H NMR (CDCl$_3$, 500 MHz) δ 7.45-7.58 (6 H, m), 7.40 (4 H, t, J = 8.0 Hz), 7.26-7.32 (1 H, m), 7.14 (2 H, d, J = 8.2 Hz), 6.80 (1 H, d, J = 8.8 Hz), 5.04 (1 H, t, J = 7.7 Hz), 3.79-3.93 (2 H, m), 3.78 (2 H, s), 2.62-2.75 (1 H, m), 2.28-2.37 (1 H, m), 2.26 (3 H, s), 2.19 (1 H, d), 1.35 (6 H, s). |
| 81 | 22 | (3-(4-(trifluoromethyl)phenoxy)pyrrolidin-2-one with 4-(2-hydroxy-2-methylpropoxy)-3-methylphenyl on N) | 3 | 2<br>4.44 | 438 | $^1$H NMR (CDCl$_3$, 500 MHz) δ 7.40 (1 H, d, J = 2.5 Hz), 7.32 (1 H, dd, J = 9.1, 2.5 Hz), 7.14 (2 H, d, J = 8.2 Hz), 6.99 (2 H, d, J = 8.2 Hz), 6.73 (1 H, d, J = 9.1 Hz), 4.94 (1 H, t, J = 7.4 Hz), 3.77-3.85 (1 H, m), 3.72-3.77 (1 H, m), 3.71 (2 H, s), 3.23 (2 H, q, J = 10.8 Hz), 2.59 (1 H, dd, J = 13.2, 3.8 Hz), 2.20-2.26 (1 H, m), 2.19 (3 H, s), 1.29 (6 H, s). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 82 | 11 | (4-cyclopropylphenoxy pyrrolidinone with 2-hydroxy-2-methylpropoxy-3-methylphenyl group) | 3 | 3 3.70 | 396 | $^1$H NMR (DMSO-d$_6$, 500 MHz) δ 7.46 (1 H, s), 7.42 (1 H, dd, J = 8.8, 2.8 Hz), 6.97-7.04 (2 H, m), 6.82-6.97 (3 H, m), 5.11 (1 H, t, J = 8.0 Hz), 4.62 (1 H, br. s.), 3.72-3.84 (2 H, m), 3.68 (2 H, s), 2.57-2.72 (1 H, m), 2.19 (3 H, s), 2.01 (1 H, dq, J = 12.7, 8.3 Hz), 1.75-1.93 (1 H, m), 1.22 (6 H, s), 0.82-0.94 (2 H, m), 0.49-0.66 (2 H, m). |
| 83 | 168 | (S)-enantiomer analog | 2 | 3 3.70 | 396 | $^1$H NMR (DMSO-d$_6$, 500 MHz) δ 7.46 (1 H, s), 7.42 (1 H, dd, J = 8.8, 2.8 Hz), 6.97-7.05 (2 H, m), 6.84-6.96 (3 H, m), 5.11 (1 H, t, J = 8.0 Hz), 4.62 (1 H, s), 3.71-3.83 (2 H, m), 3.68 (2 H, s), 2.58-2.70 (1 H, m), 2.19 (3 H, s), 1.95-2.08 (1 H, m), 1.79-1.93 (1 H, m), 1.22 (6 H, s), 0.87 (2 H, m), 0.58 (2 H, m). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 84 | 5 | (structure with cyclopropyl-phenoxy pyrrolidinone) | 2 | 3, 3.69 | 396 | $^1$H NMR (DMSO-d$_6$, 500 MHz) δ 7.46 (1 H, s), 7.42 (1 H, dd, J = 8.8, 2.2 Hz), 6.97-7.03 (2 H, m), 6.85-IS 6.95 (3 H, m), 5.11 (1 H, t, J = 8.0 Hz), 4.62 (1 H, s), 3.72-3.82 (2 H, m), 3.68 (2 H, s), 2.58-2.68 (1 H, m), 2.19 (3 H, s), 1.95-2.09 (1 H, m), 1.79-1.91 (1 H, m), 1.22 (6 H, s), 0.82-0.92 (2 H, m), 0.55-0.61 (2 H, m). |
| 85 | 22 | (structure with iodo-phenoxy pyrrolidinone) | 3 | 3, 3.75 | 482 | $^1$H NMR (DMSO-d$_6$, 500 MHz) δ 7.61 (2 H, d, J = 8.8 Hz), 7.46 (1 H, s), 7.34-7.44 (1 H, m), 6.84-10 6.99 (3 H, m), 5.20 (1 H, t, J = 8.0 Hz), 4.62 (1 H, s), 3.72-3.85 (2 H, m), 3.68 (2 H, s), 2.58-2.75 (1 H, m), 2.19 (3 H, s), 1.93-2.10 (1 H, m), 1.21 (6 H, s). |
| 86 | 5000 | (structure with trifluoromethyl-pyridinyloxy pyrrolidinone) | 3 | 3, 2.91 | 425 | $^1$H NMR (DMSO-d$_6$, 500 MHz) δ 8.39 (1 H, s), 7.72 (1 H, dd, J = 9.9, 2.8 Hz), 7.46 (1 H, d, J = 2.2 Hz), 7.40 (1 H, dd, J = 8.8, 2.8 Hz), 6.91 (1 H, d, J = 8.8 Hz), 6.57 (1 H, d, J = 9.9 Hz), 5.36 (1 H, t, J = 9.4 Hz), 4.62 (1 H, s), 3.76-3.95 (2 H, m), 3.68 (2 H, s), 2.30-2.48 (2 H, m), 2.19 (3 H, s), 1.22 (6 H, s). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 87 | 7000 | (structure with 6-Br pyridine) | 3 | 3, 3.21 | 435 | $^1$H NMR (DMSO-d$_6$, 500 MHz) δ 8.23 (1 H, d, J = 2.8 Hz), 7.50-7.62 (2 H, m), 7.46 (1 H, s), 7.41 (1 H, dd, J = 8.8, 2.8 Hz), 6.90 (1 H, d, J = 8.8 Hz), 5.35 (1 H, t, J = 8.0 Hz), 4.62 (1 H, s), 3.72-3.93 (2 H, m), 3.68 (2 H, s), 2.65-2.76 (1 H, m), 2.19 (3 H, s), 2.06-2.16 (1 H, m), 1.21 (6 H, s). |
| 88 | 45 | (structure with 6-Ph pyridine) | 6 | 3, 3.17 | 433 | $^1$H NMR (DMSO-d$_6$, 500 MHz) δ 8.47 (1 H, d, J = 3.3 Hz), 8.02 (2 H, d, J = 7.2 Hz), 7.93 (1 H, d, J = 8.8 Hz), 7.63 (1 H, dd, J = 9.1, 3.0 Hz), 7.41-7.52 (4 H, m), 7.37 (1 H, t, J = 7.4 Hz), 6.91 (1 H, d, J = 8.8 Hz), 5.39 (1 H, t, J = 8.3 Hz), 4.62 (1 H, s), 3.77-3.90 (2 H, m), 3.69 (2 H, s), 2.67-2.79 (1 H, m), 2.20 (3 H, s), 2.07-2.18 (1 H, m), 1.22 (6 H, s). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 89 | 37 | [structure: pyrrolidinone with 4-(pyridin-4-yl)phenoxy group and 2-hydroxy-2-methylpropoxy-3-methylphenyl group] | 6 | 3 2.47 | 433 | $^1$H NMR (DMSO-d$_6$, 500 MHz) δ 8.78 (2 H, d, J = 5.5 Hz), 8.12 (2 H, d, J = 5.0 Hz), 7.98 (2 H, d, J = 8.8 Hz), 7.49 (1 H, d, J = 2.8 Hz), 7.38-7.48 (1 H, m), 7.28 (2 H, d, J = 8.8 Hz), 6.92 (1 H, d, J = 8.8 Hz), 5.40 (1 H, t, J = 8.0 Hz), 3.78-3.94 (2 H, m), 3.70 (2 H, s), 2.69-2.82 (1 H, m), 2.21 (3 H, s), 1.99-2.19 (1 H, m), 1.23 (6 H, s). |
| 90 | 10 | [structure: pyrrolidinone with 4-phenylphenoxy group and (3,3-difluoro-1-hydroxycyclobutyl)methoxy-3-methylphenyl group] | 1 | 4 11.90 | 480 | $^1$H NMR (CDCl$_3$, 400 MHz) δ 7.51-7.60 (4 H, m), 7.39-7.48 (3 H, m), 7.29-7.37 (1 H, m), 7.14-7.21 (2 H, m), 6.86 (1 H, d, J = 8.80 Hz), 5.08 (1 H, t, J = 7.37 Hz), 4.06 (2 H, s), 3.80-3.99 (2 H, m), 2.65-2.94 (6 H, m), 2.30-2.41 (1 H, m), 2.27 (3 H, s). |
| 91 | 7 | [structure: pyrrolidinone with 4-phenylphenoxy group and 2-hydroxy-3-(ethylsulfonyl)propoxy-3-methylphenyl group] | 8 | 4 10.57 | 510 | $^1$H NMR (CDCl$_3$, 400 MHz) δ 7.52-7.59 (5 H, m), 7.39-7.46 (3 H, m), 7.29-7.36 (1 H, m), 7.15-7.20 (2 H, m), 6.83 (1 H, d, J = 8.80 Hz), 5.08 (1 H, t, J = 7.48 Hz), 4.69 (1 H, br. s.), 4.01-4.11 (2 H, m), 3.81-3.97 (2 H, m), 3.27-3.39 (2 H, m), 3.14-3.26 (2 H, m), 3.13 (1 H, br. s.), 2.66-2.77 (1 H, m), 2.28-2.40 (1 H, m), 2.26 (3 H, s), 1.46 (3 H, t, J = 7.48 Hz). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 92 | 22 | 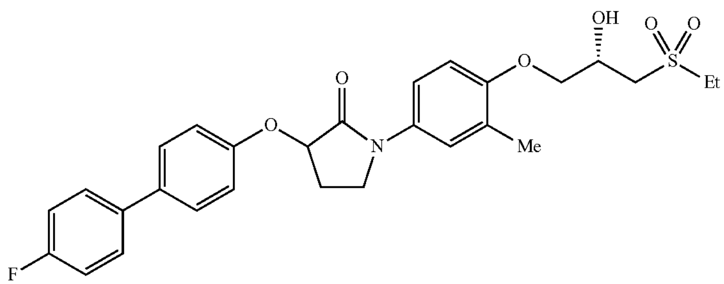 [SMILES: CCS(=O)(=O)C[C@@H](O)COc1ccc(N2CCC(Oc3ccc(-c4ccc(F)cc4)cc3)C2=O)cc1C] | 1 | 4 10.68 | 528 | $^1$H NMR (CDCl$_3$, 400 MHz) δ 7.44-7.54 (5 H, m), 7.42 (1 H, dd, J = 8.80, 2.64 Hz), 7.13-7.18 (2 H, m), 7.06-7.13 (2 H, m), 6.82 (1 H, d, J = 9.02 Hz), 5.06 (1 H, t, J = 7.48 Hz), 4.61-4.71 (1 H, m), 3.99-4.11 (2 H, m), 3.79-3.96 (2 H, m), 3.25-3.37 (2 H, m), 3.12-3.25 (2 H, m), 2.70 (1 H, dddd, J = 13.23, 7.52, 7.52, 3.63 Hz), 2.28-2.39 (1 H, m), 2.25 (3 H, s), 1.45 (3 H, t, J = 7.48 Hz). |
| 93 | 57 | 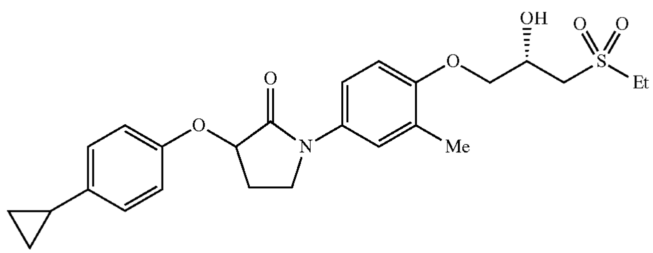 [SMILES: CCS(=O)(=O)C[C@@H](O)COc1ccc(N2CCC(Oc3ccc(C4CC4)cc3)C2=O)cc1C] | 1 | 4 10.03 | 474 | $^1$H NMR (CDCl$_3$, 400 MHz) δ 7.50-7.53 (1 H, m), 7.42 (1 H, dd, J = 8.69, 2.53 Hz), 6.95-7.06 (4 H, m), 6.82 (1 H, d, J = 8.80 Hz), 4.97 (1 H, t, J = 7.48 Hz), 4.62-4.73 (1 H, m), 4.00-4.10 (2 H, m), 3.77-3.92 (2 H, m), 3.26-3.38 (2 H, m), 3.13-3.27 (2 H, m), 2.58-2.70 (1 H, m, J = 13.18, 7.55, 7.55, 3.63 Hz), 2.26-2.33 (1 H, m), 2.25 (3 H, s), 1.82-1.91 (1 H, m, J = 8.42, 8.42, 5.17, 5.06 Hz), 1.46 (3 H, t, J = 7.48 Hz), 0.87-0.94 (2 H, m), 0.60-0.66 (2 H, m). |
| 94 | 714 | 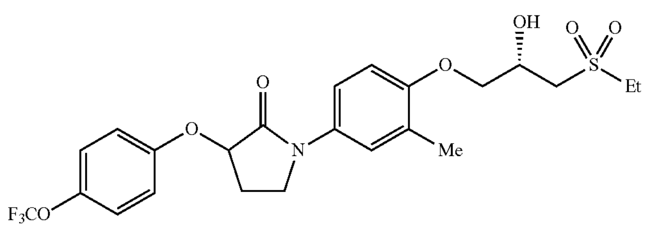 [SMILES: CCS(=O)(=O)C[C@@H](O)COc1ccc(N2CCC(Oc3ccc(OC(F)(F)F)cc3)C2=O)cc1C] | 1 | 4 10.19 | 518 | $^1$H NMR (CDCl$_3$, 400 MHz) δ 7.49-7.54 (1 H, m), 7.37-7.44 (1 H, m), 7.10-7.20 (4 H, m), 6.83 (1 H, d, J = 8.80 Hz), 5.00 (1 H, t, J = 7.37 Hz), 4.64-4.74 (1 H, m), 4.01-4.12 (2 H, m), 3.79-3.97 (2 H, m), 3.27-3.38 (2 H, m), 3.14-3.26 (2 H, m), 2.62-2.75 (1 H, m, J = 13.20, 7.59, 7.59, 3.74 Hz), 2.27-2.40 (1 H, m), 2.25 (3 H, s), 1.46 (3 H, t, J = 7.48 Hz). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 95 | 15 | 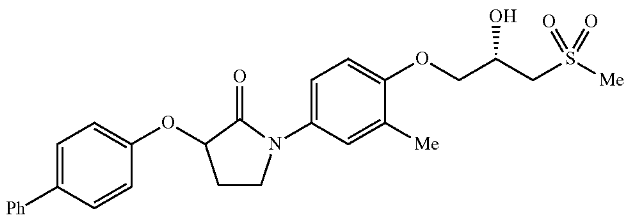 [SMILES: Cc1cc(N2CCC(Oc3ccc(-c4ccccc4)cc3)C2=O)ccc1OC[C@H](O)CS(C)(=O)=O] | 1 | 4 10.38 | 496 | $^1$H NMR (CDCl$_3$, 400 MHz) δ 7.50-7.59 (5 H, m), 7.38-7.46 (3 H, m), 7.28-7.34 (1 H, m), 7.13-7.19 (2 H, m), 6.82 (1 H, d, J = 8.80 Hz), 5.07 (1 H, t, J = 7.48 Hz), 4.61-4.72 (1 H, m), 4.00-4.07 (2 H, m), 3.80-3.96 (2 H, m), 3.24-3.41 (2 H, m), 3.09 (3 H, s), 2.97-3.06 (1 H, m), 2.71 (1 H, dddd, J = 13.23, 7.52, 7.52, 3.85 Hz), 2.28-2.40 (1 H, m), 2.25 (3 H, s). |
| 96 | 22 | 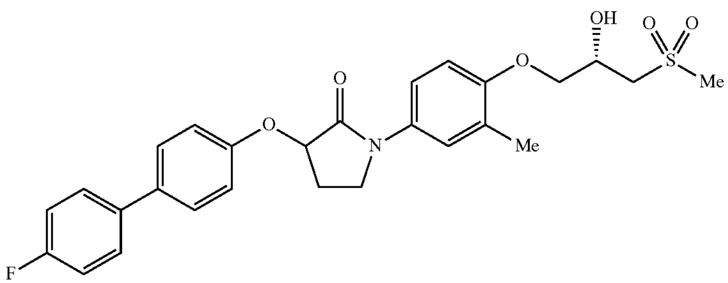 [SMILES: Cc1cc(N2CCC(Oc3ccc(-c4ccc(F)cc4)cc3)C2=O)ccc1OC[C@H](O)CS(C)(=O)=O] | 1 | 4 10.48 | 514 | $^1$H NMR (CDCl$_3$, 400 MHz) δ 7.45-7.54 (5 H, m), 7.43 (1 H, dd, J = 8.69, 2.53 Hz), 7.13-7.18 (2 H, m), 7.06-7.13 (2 H, m), 6.83 (1 H, d, J = 9.02 Hz), 5.06 (1 H, t, J = 7.48 Hz), 4.63-4.72 (1 H, m), 4.02-4.08 (2 H, m), 3.81-3.96 (2 H, m), 3.37 (1 H, dd, J = 14.31, 9.24 Hz), 3.25-3.32 (1 H, m), 3.09 (3 H, s), 2.98 (1 H, d, J = 3.96 Hz), 2.64-2.77 (1 H, m), 2.28-2.40 (1 H, m), 2.25 (3 H, s). |
| 97 | 79 | 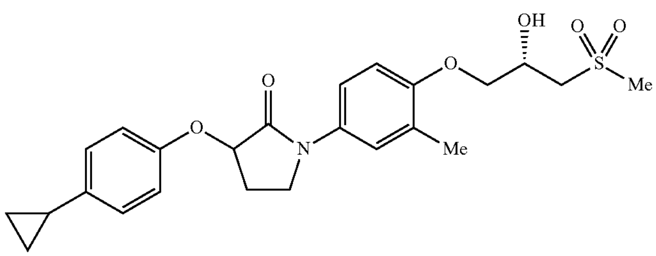 [SMILES: Cc1cc(N2CCC(Oc3ccc(C4CC4)cc3)C2=O)ccc1OC[C@H](O)CS(C)(=O)=O] | 1 | 4 9.74 | 460 | $^1$H NMR (CDCl$_3$, 400 MHz) δ 7.47-7.53 (1 H, m), 7.43 (1 H, dd, J = 8.80, 2.64 Hz), 6.96-7.06 (4 H, m), 6.82 (1 H, d, J = 8.80 Hz), 4.97 (1 H, t, J = 7.48 Hz), 4.62-4.72(1 H, m), 3.99-4.09 (2 H, m), 3.75-3.93 (2 H, m), 3.24-3.42 (2 H, m), 3.09 (3 H, s), 2.60-2.71 (1 H, m), 2.26-2.34 (1 H, m), 2.25 (3 H, s), 1.87 (1 H, tt, J = 8.39, 5.14 Hz), 0.88-0.94 (2 H, m), 0.60-0.66 (2 H, m). |

TABLE C-continued

[Structure header showing core scaffold with R2, R3, R4, X1, X2, R7, Me and pyrrolidinone-O linkage]

| Ex. # | Ki (nM) | Structure | Synthetic Procedure Used | HPLC Method $t_R$ (min) | MS (M + H) | NMR Data |
|---|---|---|---|---|---|---|
| 98 | 1427 | [Structure with 4-CF3-phenoxy group on pyrrolidinone and methylsulfonyl-hydroxypropoxy-methylphenyl] | 1 | 4 9.83 | 488 | $^1$H NMR (CDCl$_3$, 400 MHz) δ 7.56 (2 H, d, J = 8.58 Hz), 7.49 (1 H, s), 7.41 (1 H, dd, J = 8.80, 2.42 Hz), 7.17 (2 H, d, J = 8.58 Hz), 6.81 (1 H, d, J = 8.80 Hz), 5.09 (1 H, t, J = 7.37 Hz), 4.60-4.72 (1 H, m), 3.97-4.08 (2 H, m), 3.80-3.96 (2 H, m), 3.36 (1 H, dd, J = 14.75, 9.02 Hz), 3.27 (1 H, dd, J = 14.75, 1.76 Hz), 3.08 (3 H, s), 3.04 (1 H, t, J = 3.85 Hz), 2.70 (1 H, dddd, J = 13.26, 7.51, 7.51, 3.85 Hz), 2.27-2.39 (1 H, m), 2.24 (3 H, s). |
| 99 | 19 | [Structure with 4'-fluorobiphenyloxy group and methylsulfonyl-hydroxypropoxy-methylphenyl] | 1 | 4 10.38 | 514 | $^1$H NMR (CDCl$_3$, 400 MHz) δ 7.45-7.54 (5 H, m), 7.43 (1 H, dd, J = 8.91, 2.53 Hz), 7.13-7.18 (2 H, m), 7.06-7.13 (2 H, m), 6.82 (1 H, d, J = 9.02 Hz), 5.06 (1 H, t, J = 7.37 Hz), 4.62-4.72 (1 H, m), 4.00-4.10 (2 H, m), 3.77-3.96 (2 H, m), 3.32-3.41 (1 H, m, J = 14.53, 8.80 Hz), 3.28 (1 H, dd, J = 14.53, 1.54 Hz), 3.09 (3 H, s), 2.99 (1 H, d, J = 2.64 Hz), 2.70 (1 H, dddd, J = 13.29, 7.57, 7.43, 3.63 Hz), 2.34 (1 H, dddd, J = 13.15, 8.42, 7.26, 7.26 Hz), 2.25 (3 H, s). |
| 100 | 42 | [Structure with 4-cyclopropyl-phenoxy group and methylsulfonyl-hydroxypropoxy-methylphenyl] | 1 | 4 9.57 | 460 | $^1$H NMR (CDCl$_3$, 400 MHz) δ 7.49 (1 H, d, J = 2.64 Hz), 7.42 (1 H, dd, J = 8.80, 2.86 Hz), 6.95-7.04 (4 H, m), 6.81 (1 H, d, J = 8.80 Hz), 4.97 (1 H, t, J = 7.37 Hz), 4.62-4.71 (1 H, m), 4.04 (2 H, m), 3.76-3.91 (2 H, m), 3.32-3.41 (1 H, m), 3.24-3.32 (1 H, m), 3.09 (3 H, s), 2.59-2.70 (1 H, m, J = 13.18, 7.50, 7.50, 3.74 Hz), 2.24 (3 H, s), 2.21-2.33 (1 H, m), 1.81-1.91 (1 H, m), 0.86-0.93 (2 H, m), 0.59-0.65 (1 H, m). |

TABLE C-continued

| Ex. # | Ki (nM) | Structure | Synthetic Procedure Used | HPLC Method | $t_R$ (min) | MS (M + H) | NMR Data |
|---|---|---|---|---|---|---|---|
| 101 | 77 | 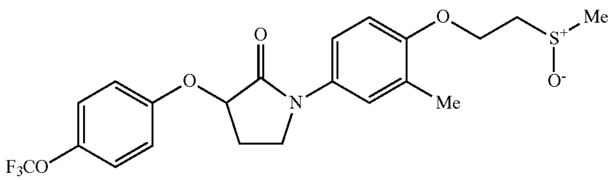 | 13 | 5 | 15.52 | 458 | $^1$H NMR (CDCl$_3$, 400 MHz) δ 7.51 (1 H, d, J = 2.64 Hz), 7.39 (1 H, dd, J = 8.80, 2.64 Hz), 7.09-7.19 (4 H, m), 6.87 (1 H, d, J = 8.80 Hz), 5.01 (1 H, t, J = 7.48 Hz), 4.42-4.47 (2 H, m), 3.80-3.94 (2 H, m), 3.19-3.28 (1 H, m), 3.07-3.13 (1 H, m), 2.72 (3 H, s), 2.64-2.71 (1 H, m), 2.26-2.37 (1 H, m), 2.24 (3 H, s). |
| 102 | 6 | 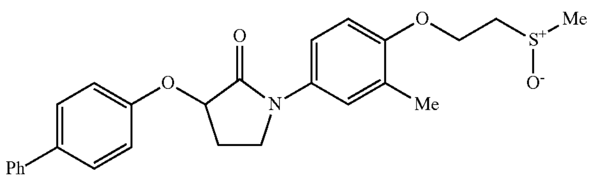 [SMILES: Cc1cc(N2CCC(Oc3ccc(-c4ccccc4)cc3)C2=O)ccc1OCC[S+](C)[O-]] | 13 | 4 | 9.82 | 450 | $^1$H NMR (CDCl$_3$, 400 MHz) δ 7.52-7.59 (5 H, m), 7.40-7.46 (3 H, m), 7.32 (1 H, t, J = 7.48 Hz), 7.15-7.20 (2 H, m), 6.88 (1 H, d, J = 8.80 Hz), 5.08 (1 H, t, J = 7.48 Hz), 4.42-4.47 (2 H, m), 3.82-3.96 (2 H, m), 3.20-3.28 (1 H, m), 3.07-3.14 (1 H, m), 2.67-2.77 (4 H, m), 2.29-2.41 (1 H, m), 2.25 (3 H, s). |
| 103 | 40 | 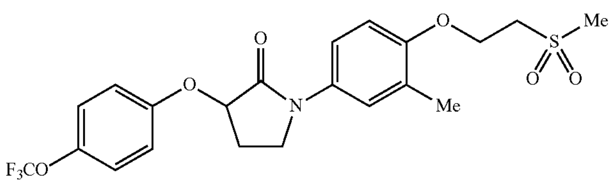 [SMILES: Cc1cc(N2CCC(Oc3ccc(OC(F)(F)F)cc3)C2=O)ccc1OCCS(C)(=O)=O] | 9 | 5 | 15.54 | 474 | $^1$H NMR (CDCl$_3$, 400 MHz) δ 7.56 (1 H, d, J = 2.86 Hz), 7.40 (1 H, dd, J = 8.80, 2.86 Hz), 7.08-7.22 (4 H, m), 6.87 (1 H, d, J = 8.80 Hz), 5.01 (1 H, t, J = 7.48 Hz), 4.41-4.50 (2 H, m), 3.79-3.97 (2 H, m), 3.49 (2 H, t, J = 5.17 Hz), 3.10 (3 H, s), 2.63-2.76 (1 H, m, J = 13.20, 7.54, 7.54, 3.63 Hz), 2.27-2.41 (1 H, m), 2.25 (3 H, s). |
| 104 | 1 | 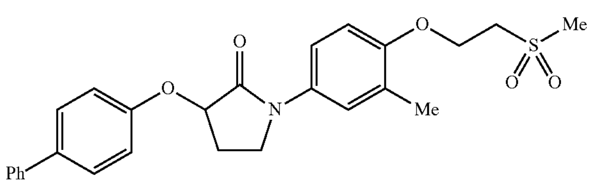 | 9 | 5 | 16.07 | 466 | $^1$H NMR (CDCl$_3$, 400 MHz) δ 7.51-7.62 (5 H, m), 7.38-7.48 (3 H, m), 7.29-7.35 (1 H, m), 7.14-7.21 (2 H, m), 6.87 (1 H, d, J = 9.02 Hz), 5.09 (1 H, t, J = 7.48 Hz), 4.42-4.49 (2 H, m), 3.81-3.97 (2 H, m), 3.49 (2 H, t, J = 5.17 Hz), 3.10 (3 H, s), 2.67-2.79 (1 H, m, J = 13.18, 7.50, 7.50, 3.74 Hz), 2.29-2.43 (1 H, m), 2.25 (3 H, s). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 105 | 2 | 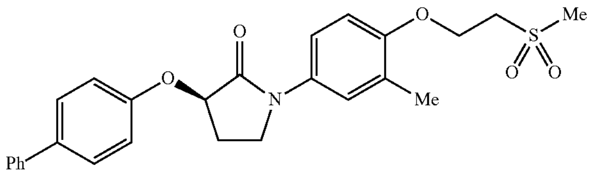 | 14 | 4 10.90 | 466 | $^1$H NMR (CDCl$_3$, 400 MHz) δ 7.49-7.62 (5 H, m), 7.40-7.48 (3 H, m), 7.29-7.36 (1 H, m), 7.14-7.20 (2 H, m), 6.87 (1 H, d, J = 9.02 Hz), 5.08 (1 H, t, J = 7.48 Hz), 4.40-4.49 (2 H, m), 3.79-3.98 (2 H, m), 3.49 (2 H, t, J = 5.06 Hz), 3.10 (3 H, s), 2.65-2.79 (1 H, m, J = 13.26, 7.57, 7.57, 3.74 Hz), 2.29-2.43 (1 H, m, J = 13.20, 8.58, 7.26, 7.26 Hz), 2.26 (3 H, s). |
| 106 | 636 | 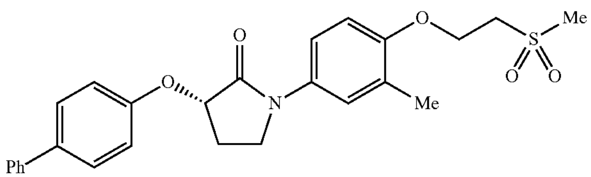 [SMILES: Cc1cc(N2CCC(Oc3ccc(-c4ccccc4)cc3)C2=O)ccc1OCCS(C)(=O)=O] | 14 | 4 10.90 | 466 | $^1$H NMR (CDCl$_3$, 400 MHz) δ 7.51-7.60 (5 H, m), 7.40-7.47 (3 H, m), 7.30-7.37 (1 H, m), 7.13-7.21 (2 H, m), 6.87 (1 H, d, J = 8.80 Hz), 5.08 (1 H, t, J = 7.48 Hz), 4.40-4.50 (2 H, m), 3.79-3.99 (2 H, m), 3.49 (2 H, t, J = 5.06 Hz), 3.10 (3 H, s), 2.65-2.79 (1 H, m, J = 13.18, 7.55, 7.55, 3.63 Hz), 2.29-2.45 (1 H, m), 2.26 (3 H, s). |
| 107 | 5 | 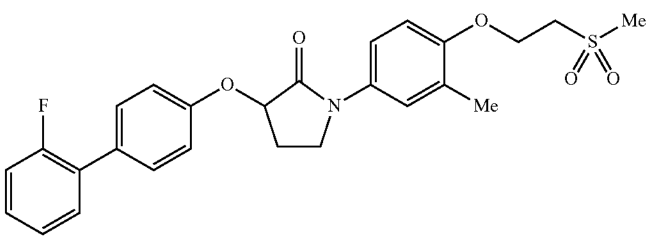 [SMILES: Cc1cc(N2CCC(Oc3ccc(-c4ccccc4F)cc3)C2=O)ccc1OCCS(C)(=O)=O] | 9 | 4 10.97 | 484 | $^1$H NMR (CDCl$_3$, 400 MHz) δ 7.58 (1 H, d, J = 2.20 Hz), 7.48-7.54 (2 H, m), 7.38-7.47 (2 H, m), 7.28-7.33 (1 H, m), 7.11-7.23 (4 H, m), 6.88 (1 H, d, J = 8.80 Hz), 5.09 (1 H, t, J = 7.48 Hz), 4.43-4.49 (2 H, m), 3.82-3.97 (2 H, m), 3.49 (2 H, t, J = 5.28 Hz), 3.10 (3 H, s), 2.67-2.78 (1 H, m, J = 13.18, 7.50, 7.50, 3.74 Hz), 2.29-2.42 (1 H, m), 2.26 (3 H, s). |
| 108 | 5 | 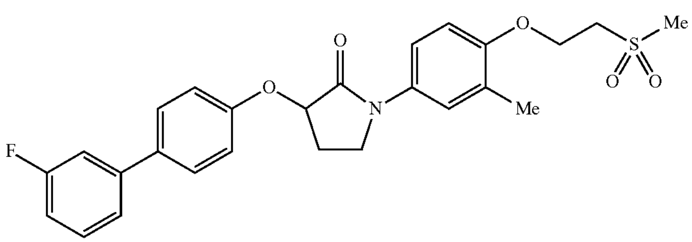 [SMILES: Cc1cc(N2CCC(Oc3ccc(-c4cccc(F)c4)cc3)C2=O)ccc1OCCS(C)(=O)=O] | 9 | 4 11.11 | 484 | $^1$H NMR (CDCl$_3$, 400 MHz) δ 7.57 (1 H, d, J = 2.20 Hz), 7.50-7.55 (2 H, m), 7.23-7.45 (4 H, m), 7.15-7.20 (2 H, m), 6.98-7.04 (1 H, m), 6.88 (1 H, d, J = 9.02 Hz), 5.09 (1 H, t, J = 7.48 Hz), 4.42-4.50 (2 H, m), 3.81-3.98 (2 H, m), 3.49 (2 H, t, J = 5.28 Hz), 3.10 (3 H, s), 2.67-2.79 (1 H, m, J = 13.29, 7.50, 7.50, 3.85 Hz), 2.29-2.43 (1 H, m), 2.26 (3 H, s). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 109 | 6 | (structure) | 9 | 4 11.08 | 484 | $^1$H NMR (CDCl$_3$, 400 MHz) δ 7.57 (1 H, d, J = 2.20 Hz), 7.46-7.53 (4 H, m), 7.43 (1 H, dd, J = 8.80, 2.64 Hz), 7.07-7.19 (4 H, m), 6.88 (1 H, d, J = 8.80 Hz), 5.07 (1 H, t, J = 7.48 Hz), 4.41-4.50 (2 H, m), 3.80-3.96 (2 H, m), 3.49 (2 H, t, J = 5.06 Hz), 3.10 (3 H, s), 2.64-2.77 (1 H, m, J = 13.26, 7.46, 7.46, 3.74 Hz), 2.28-2.43 (1 H, m), 2.26 (3 H, s). |
| 110 | 3 | (structure) | 14 | 4 11.06 | 484 | $^1$H NMR (CDCl$_3$, 400 MHz) δ 7.57 (1 H, d, J = 2.42 Hz), 7.45-7.54 (4 H, m), 7.43 (1 H, dd, J = 8.80, 2.64 Hz), 7.06-7.20 (4 H, m), 6.88 (1 H, d, J = 8.80 Hz), 5.07 (1 H, t, J = 7.48 Hz), 4.42-4.49 (2 H, m), 3.81-3.98 (2 H, m), 3.49 (2 H, t, J = 5.28 Hz), 3.10 (3 H, s), 2.65-2.77 (1 H, m, J = 13.18, 7.50, 7.50, 3.74 Hz), 2.29-2.41 (1 H, m), 2.26 (3 H, s). |
| 111 | 1742 | (structure) | 14 | 4 11.12 | 484 | $^1$H NMR (CDCl$_3$, 400 MHz) δ 7.57 (1 H, d, J = 2.20 Hz), 7.45-7.54 (4 H, m), 7.43 (1 H, dd, J = 8.91, 2.53 Hz), 7.08-7.20 (4 H, m), 6.87 (1 H, d, J = 8.80 Hz), 5.07 (1 H, t, J = 7.48 Hz), 4.42-4.49 (2 H, m), 3.81-3.98 (2 H, m), 3.49 (2 H, t, J = 5.06 Hz), 3.10 (3 H, s), 2.65-2.79 (1 H, m, J = 13.18, 7.55, 7.55, 3.63 Hz), 2.28-2.42 (1 H, m), 2.26 (3 H, s). |

TABLE C-continued

| Ex. # | Ki (nM) | Structure | Synthetic Procedure Used | HPLC Method $t_R$ (min) | MS (M + H) | NMR Data |
|---|---|---|---|---|---|---|
| 112 | 31 | 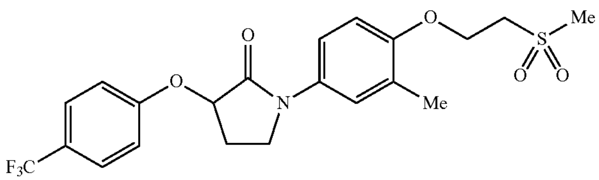 [SMILES: Cc1cc(N2CCC(Oc3ccc(C(F)(F)F)cc3)C2=O)ccc1OCCS(C)(=O)=O] | 9 | 4 10.31 | 458 | $^1$H NMR (CDCl$_3$, 400 MHz) δ 7.54-7.62 (3 H, m), 7.40 (1 H, dd, J = 8.80, 2.64 Hz), 7.18 (2 H, d, J = 8.58 Hz), 6.87 (1 H, d, J = 8.80 Hz), 5.10 (1 H, t, J = 7.37 Hz), 4.42-4.49 (2 H, m), 3.81-3.99 (2 H, m), 3.49 (2 H, t, J = 5.28 Hz), 3.10 (3 H, s), 2.66-2.78 (1 H, m, J = 13.29, 7.55, 7.55, 3.74 Hz), 2.29-2.41 (1 H, m), 2.25 (3 H, s). |
| 113 | 55 | 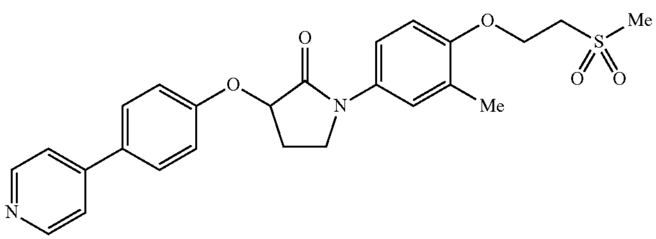 [SMILES: Cc1cc(N2CCC(Oc3ccc(-c4ccncc4)cc3)C2=O)ccc1OCCS(C)(=O)=O] | 15 | 4 5.19 | 467 | $^1$H NMR (CDCl$_3$, 400 MHz) δ 8.63 (2 H, d, J = 4.62 Hz), 7.55-7.66 (3 H, m), 7.48 (2 H, d, J = 5.94 Hz), 7.42 (1 H, dd, J = 8.80, 2.64 Hz), 7.19-7.25 (2 H, m), 6.87 (1 H, d, J = 9.02 Hz), 5.12 (1 H, t, J = 7.48 Hz), 4.43-4.49 (2 H, m), 3.83-3.98 (2 H, m), 3.49 (2 H, t, J = 5.28 Hz), 3.10 (3 H, s), 2.68-2.79 (1 H, m, J = 13.20, 7.48, 7.48, 3.74 Hz), 2.31-2.42 (1 H, m), 2.25 (3 H, s). |
| 114 | 7 | 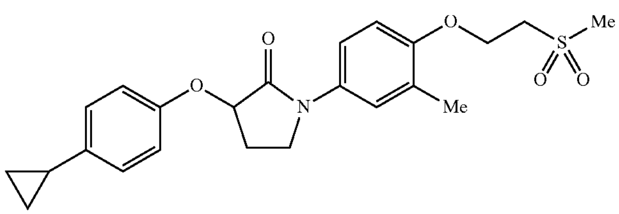 [SMILES: Cc1cc(N2CCC(Oc3ccc(C4CC4)cc3)C2=O)ccc1OCCS(C)(=O)=O] | 9 | 4 10.30 | 430 | $^1$H NMR (CDCl$_3$, 400 MHz) δ 7.56 (1 H, d, J = 2.20 Hz), 7.42 (1 H, dd, J = 8.80, 2.42 Hz), 6.96-7.06 (4 H, m), 6.86 (1 H, d, J = 8.80 Hz), 4.97 (1 H, t, J = 7.48 Hz), 4.42-4.49 (2 H, m), 3.77-3.92 (2 H, m), 3.48 (2 H, t, J = 5.28 Hz), 3.09 (3 H, s), 2.61-2.71 (1 H, m, J = 13.15, 7.51, 7.51, 3.74 Hz), 2.26-2.35 (1 H, m), 2.25 (3 H, s), 1.82-1.92 (1 H, m, J = 8.42, 8.42, 5.17, 5.06 Hz), 0.87-0.94 (2 H, m), 0.59-0.66 (2 H, m). |

TABLE D

| Ex. # | Ki (nM) | Structure | Synthetic Procedure Used | HPLC Method $t_R$ (min) | MS (M + H) | NMR Data |
|---|---|---|---|---|---|---|
| 115 | 11 | (F₃CO-phenyl, OMe, CH₂C(Me)₂OH) | 16 | 3 / 3.51 | 436 | ¹H NMR (CDCl₃, 400 MHz) δ 7.71 (1 H, s), 7.17-7.26 (4 H, m), 6.92-6.97 (2 H, m), 5.93 (1 H, s), 4.31 (2 H, d, J = 2.8 Hz), 3.90 (3 H, s), 3.82-3.85 (2 H, m), 1.35 (6 H, s). |
| 116 | 3 | (cyclopropyl-phenyl, OMe, CH₂C(Me)₂OH) | 16 | 3 / 3.54 | 410 | ¹H NMR (DMSO-d₆, 500 MHz) δ 7.49 (1 H, d, J = 2.2 Hz), 7.18 (1 H, dd, J = 8.8, 2.8 Hz), 7.10-7.15 (2 H, m), 7.04-7.10 (2 H, m), 6.98(1 H, d, J = 8.8 Hz), 6.18 (1 H, t, J = 2.5 Hz), 4.40 (2 H, d, J = 2.2 Hz), 3.78 (3 H, s), 3.68 (2 H, s), 1.88-2.04 (1 H, m), 1.20 (6 H, s), 0.89-1.01 (2 H, m), 0.61-0.72 (2 H, m). |
| 117 | 25 | (F₃CO-phenyl, Me, CH₂C(Me)₂OH) | 16 | 2 / 3.68 | 438 | ¹H NMR (CDCl₃, 400 MHz) δ 7.41-7.54 (2 H, m), 7.14-7.26 (4 H, m), 6.83 (1 H, d, J = 8.8 Hz), 5.88 (1 H, t, J = 2.5 Hz), 4.27 (2 H, d, J = 2.8 Hz), 3.80 (2 H, s), 2.29 (3 H, s), 2.20 (1 H, s), 1.34-1.40 (6 H, m). |
| 118 | 9 | (cyclopropyl-phenyl, Me, CH₂C(Me)₂OH) | 16 | 3 / 3.72 | 394 | ¹H NMR (CDCl₃, 500 MHz) δ 7.46-7.55 (2 H, m), 7.10 (4 H, s), 6.83 (1 H, d, J = 8.8 Hz), 5.74 (1 H, t, J = 2.2 Hz), 4.23 (2 H, d, J = 2.2 Hz), 3.81 (2 H, s), 2.30 (3 H, s), 1.86-1.98 (1 H, m), 1.38 (6 H, s), 0.94-1.03 (2 H, m), 0.66-0.74 (2 H, m). |
| 119 | 4 | (cyclopropyl-phenyl, OMe, CH₂C(Me)(OH)CH₂OH) | 17 | 3 / 3.23 | 426 | ¹H NMR (DMSO-d₆, 500 MHz) δ 7.49 (1 H, d, J = 2.2 Hz), 7.18 (1 H, dd, J = 8.8, 2.8 Hz), 7.10-7.15 (2 H, m), 7.04-7.10 (2 H, m), 6.98 (1 H, d, J = 8.8 Hz), 6.12-6.23 (1 H, m), 4.39 (2 H, d, J = 2.8 Hz), 3.69-3.84 (5 H, m), 3.28-3.41 (2 H, m), 1.85-2.03 (1 H, m), 1.13 (3 H, s), 0.88-0.99 (2 H, m), 0.60-0.71 (2 H, m). |

TABLE D-continued

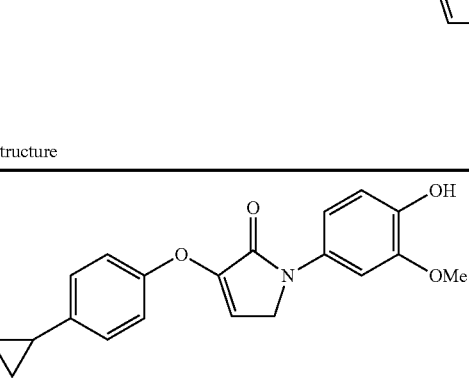

| Ex. # | Ki (nM) | Structure | Synthetic Procedure Used | HPLC Method $t_R$ (min) | MS (M + H) | NMR Data |
|---|---|---|---|---|---|---|
| 120 | 10 | 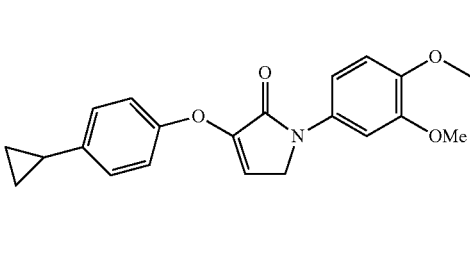 | 17 | 3 3.21 | 338 | $^1$H NMR (CD$_2$Cl$_2$, 500 MHz) δ 7.57 (1 H, d, J = 2.2 Hz), 7.09-7.16 (2 H, m), 7.02-7.10 (2 H, m), 6.83-6.95 (2 H, m), 5.83 (1 H, s), 4.25 (2 H, d, J = 2.2 Hz), 3.92 (3 H, s), 1.83-2.01 (1 H, m), 0.92-1.05 (2 H, m), 0.62-0.77 (2 H, m). |
| 121 | 2 | 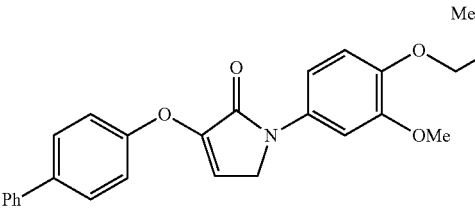 | 16 | 3 3.55 | 422 | $^1$H NMR (DMSO-d$_6$, 500 MHz) δ ppm 7.42 (1 H, d, J = 2.2 Hz), 7.11 (1 H, dd, J = 8.8, 2.7 Hz), 7.03-7.08 (2 H, m), 6.98-7.03 (2 H, m), 6.93 (1 H, d, J = 8.8 Hz), 6.12 (1 H, s), 4.33 (2 H, d, J = 2.2 Hz), 3.77-3.90 (2 H, m), 3.71 (3 H, s), 3.48 (3 H, br. s.), 3.20-3.26 (1 H, m), 1.81-1.92 (1 H, m), 0.82-0.94 (3 H, m), 0.53-0.64 (2 H, m), 0.28-0.35 (2 H, m), 0.17-0.28 (2 H, m). |
| 122 | 3 | 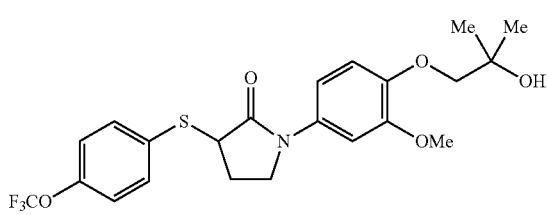 [SMILES: COc1cc(N2CC=C(Oc3ccc(OC(F)(F)F)cc3)C2=O)ccc1OCC(C)(C)O] | 16 | 3 3.69 | 446 | $^1$H NMR (DMSO-d$_6$, 500 MHz) δ 7.67 (2 H, d, J = 8.8 Hz), 7.62 (2 H, d, J = 8.3 Hz), 7.47 (1 H, d, J = 2.2 Hz), 7.42 (2 H, t, J = 7.7 Hz), 7.27-7.35 (1 H, m), 7.23 (2 H, d, J = 8.3 Hz), 7.15 (1 H, dd, J = 8.8, 2.8 Hz), 6.94 (1 H, d, J = 8.8 Hz), 6.40 (1 H, s), 4.42 (2 H, d, J = 2.2 Hz), 3.74 (3 H, s), 3.64 (2 H, s), 1.16 (6 H, s). |

Example 123

1-(4-(2-hydroxy-2-methylpropoxy)-3-methoxyphenyl)-3-((4-(trifluoromethoxy)phenyl)thio)pyrrolidin-2-one

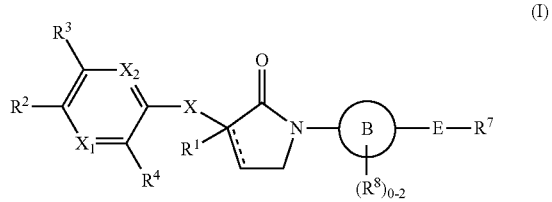

4-(trifluoromethoxy)benzenethiol (43 mg, 0.22 mmol) was added to a mixture of 3-bromo-1-(4-(2-hydroxy-2-methylpropoxy)-3-methoxyphenyl)pyrrolidin-2-one (72 mg, 0.2 mmol) and AMBERLITE® IRA-400 (20 mg, 0.01 mmol) in aq. 30% KOH (0.19 mL, 1.0. mmol) and DCM (4.0 mL) prepared from 1-(4-amino-2-methoxyphenoxy)-2-methylpropan-2-ol (43 mg, 0.2 mmol) and NEt$_3$ (0.029 ml, 0.208 mmol), and 2,4-dibromobutanoyl chloride (0.027 ml, 0.2 mmol) following Procedure 3. The reaction mixture was stirred at rt for 20 min, diluted with water (2 mL), and extracted with DCM (3×4 mL). The combined organic layers were washed with 1 N HCl (4 mL) and brine, dried over anhydrous Na$_2$SO$_4$, and concentrated. The crude product was purified by flash chromatography (silica gel, EtOAc/hexanes 0-60% gradient) to afford Example 123 (50 mg, 0.106 mmol 53% yield) as an colourless oil.

What is claimed is:

1. A compound of Formula (I):

(I)

or a stereoisomer, a tautomer, or a pharmaceutically acceptable salt thereof, wherein:

141

═══ is independently a single or double bond; provided
that when ═══ is a single bond, $R^1$ is H or $C_{1-4}$ alkyl;
and when ═══ is a double bond $R^1$ is absent;
X is O;
$X_1$ is independently N or $CR^5$;
$X_2$ is independently N or $CR^6$;
provided that $X_1$ and $X_2$ are not both N;
ring B is $C_{3-6}$ carbocycle;
E is independently O;
$R^2$, at each occurrence, is independently selected from H, halogen, $C_{1-6}$ alkyl, $C_{1-6}$ alkoxy, $C_{1-6}$ haloalkyl, $C_{1-6}$ haloalkoxy, $R^9$, or —O—$R^9$;
$R^3$, $R^4$, $R^5$ and $R^6$, at each occurrence, are independently selected from H, halogen, $C_{1-6}$ alkyl, $C_{1-6}$ alkoxy, $C_{1-6}$ haloalkyl, or $C_{1-6}$ haloalkoxy;
$R^7$ is independently selected from $C_{1-8}$ alkyl substituted with 0-3 $R^a$, or

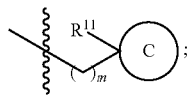

ring C is 3 to 6-membered heterocycle containing carbon 37 atoms and 1-2 heteroatoms selected from the group consisting of O, and $S(O)_p$; wherein said heterocycle is substituted with 0-3 $R^c$;
$R^8$, at each occurrence, is independently selected from H, $C_{1-6}$ alkyl, $C_{1-6}$ alkoxy; halogen, $C_{1-6}$ haloalkyl, or $C_{1-6}$ haloalkoxy;
$R^9$, at each occurrence, is independently a $C_{3-6}$ carbocycle or a 3- to 6-membered heterocycle containing carbon atoms and 1-4 heteroatoms selected from the group consisting of N, $NR^e$, O, and $S(O)_p$; wherein said carbocycle and heterocycle are each substituted with 0-3 $R^b$;
$R^{11}$, at each occurrence, is independently H or $OR^d$;
$R^a$, at each occurrence, is independently selected from $OR^d$, $C_{3-6}$ cycloalkyl, $SO(C_{1-4}$ alkyl), or $SO_2(C_{1-4}$ alkyl);
$R^b$, at each occurrence, is independently selected from halogen, OH, CN, $C_{1-4}$ alkyl, $C_{1-4}$ alkoxy, or $C_{1-4}$ haloalkyl;
$R^c$, at each occurrence, is independently selected from halogen, $OR^d$, $CH_2OR^d$, $C_{1-4}$ alkyl, $C_{1-4}$ alkoxy, or $C_{1-4}$ haloalkyl;
$R^d$, at each occurrence, is independently H;
m, at each occurrence, is independently 0, 1, 2, or 3; and
p, at each occurrence, is independently 0, 1 or 2.

2. A compound according to claim 1, wherein:
═══ is independently a single or double bond; provided that when ═══ is a single bond, $R^1$ is H or $C_{1-2}$ alkyl; and when ═══ is a double bond $R^1$ is absent;
$X_1$ is independently N or $CR^5$;
$X_2$ is independently N or $CR^6$;
provided that $X_1$ and $X_2$ are not both N;
ring B is phenylene;
$R^2$, at each occurrence, is independently at selected from $C_{1-6}$ alkyl, $C_{1-6}$ alkoxy, $C_{1-6}$ haloalkyl, $C_{1-6}$ haloalkoxy, $R^9$, or —O—$R^9$;
$R^3$, $R^4$, $R^5$ and $R^6$, at each occurrence, are independently selected from H, halogen, $C_{1-4}$ alkyl, $C_{1-4}$ alkoxy, $C_{1-2}$ haloalkyl, or $C_{1-2}$ haloalkoxy;
$R^7$ is independently selected from $C_{1-6}$ alkyl substituted with 0-3 $R^a$,

142

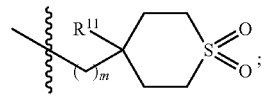

$R^{11}$, at each occurrence, is independently H or $OR^d$; and
m, at each occurrence, is independently 0, 1 or 2.

3. A compound according to claim 1, wherein the compound is of Formula (II):

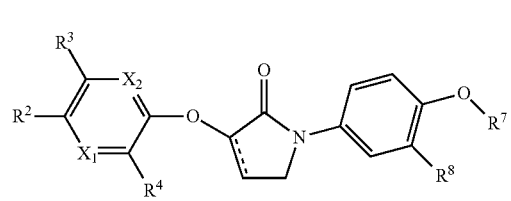

or a stereoisomer, a tautomer, or a pharmaceutically acceptable salt thereof, wherein:
═══ is a single or double bond;
$X_1$ is independently N or $CR^5$;
$X_2$ is independently N or $CR^6$;
provided that $X_1$ and $X_2$ are not both N;
$R^2$, at each occurrence, is independently at selected from H, halogen, $CF_3$, $CH_2CF_3$, $OCF_3$, $C_{1-4}$ alkoxy, cyclopropyl, cyclopropyloxy, phenyl, 2-$C_{1-4}$ alkyl-phenyl, 2-$C_{1-4}$ alkoxy-phenyl, 2-halo-phenyl, 3-halo-phenyl, 4-halo-phenyl, 2-$CF_3$-phenyl, azetidin-1-yl, pyrrol-1-yl, imidazol-1-yl, morpholin-1-yl, pyrid-3-yl, pyrid-4-yl, or 3-halo-pyrid-4-yl;
$R^3$, $R^4$, $R^5$ and $R^6$, at each occurrence, are independently selected from H, halogen, $C_{1-4}$ alkyl, $C_{1-4}$ alkoxy, $C_{1-2}$ haloalkyl, or $C_{1-2}$ haloalkoxy;
$R^7$ is independently selected from $C_{1-4}$ alkyl, —$CH_2C(C_{1-2}$ alkyl$)_2$OH, —$CH_2C(C_{1-2}$ alkyl$)(CH_2OH)OH$, —$CH_2CH_2SO(C_{1-2}$ alkyl), —$CH_2CH_2SO_2(C_{1-2}$ alkyl), —$CH_2CH(OH)CH_2SO_2(C_{1-2}$ alkyl),

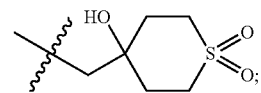 [SMILES: *CC1(O)CCS(=O)(=O)CC1]

and
$R^8$ is independently $C_{1-4}$ alkyl substituted with 0-1 halogen or $C_{1-4}$ alkoxy with 0-1 halogen.

4. A compound according to claim 1, wherein the compound is of Formula (IIa):

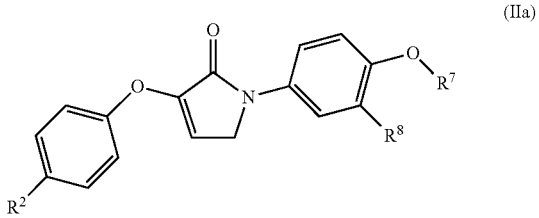

or a stereoisomer, a tautomer, or a pharmaceutically acceptable salt thereof, wherein:

R² is independently selected from OCF₃, cyclopropyl, or phenyl;
R⁷ is independently selected from —CH₂C(C₁₋₂ alkyl)₂OH, or —CH₂C(C₁₋₂ alkyl)(CH₂OH)OH
R⁸ is independently C₁₋₄ alkyl or C₁₋₄ alkoxy.

5. A compound according to claim 4, wherein:
R² is independently selected from OCF₃, cyclopropyl, or phenyl;
R⁷ is independently selected from —CH₂C(Me)₂OH, —CH₂C(Me)(CH₂OH)OH, or —CH₂C(Me)₂OC(O)CH₂NH₂; and
R⁸ is independently Me or OMe.

6. A compound according to claim 4, wherein:
R², R⁷, and R⁸ are selected from the group consisting of

| R² | R⁷ | R⁸ |
|---|---|---|
| OCF₃ | —CH₂C(Me)₂OH | OMe |
| cyclopropyl | —CH₂C(Me)₂OH | OMe |
| OCF₃ | —CH₂C(Me)₂OH | Me |
| cyclopropyl | —CH₂C(Me)₂OH | Me |
| cyclopropyl | —CH₂C(Me)(CH₂OH)OH | OMe |
| cyclopropyl | 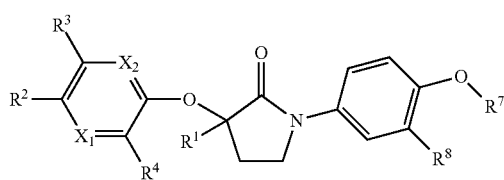 | OMe |
| phenyl | —CH₂C(Me)₂OH | OMe |

7. A compound according to claim 1, wherein the compound is of Formula (IIb),

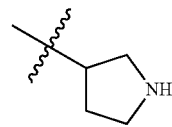 [SMILES: *C1CCNC1]

(IIb)

or a stereoisomer, a tautomer, or a pharmaceutically acceptable salt thereof, wherein:
X₁ is independently N or CR⁵;
X₂ is independently N or CR⁶;
provided that X₁ and X₂ are not both N;
R¹ is independently H or C₁₋₂ alkyl;
R², at each occurrence, is independently selected from halogen, CF₃, CH₂CF₃, OCF₃, C₁₋₄ alkoxy, cyclopropyl, cyclopropyloxy, phenyl, 2-C₁₋₄ alkyl-phenyl, 2-C₁₋₄ alkoxy-phenyl, 2-halo-phenyl, 3-halo-phenyl, 4-halo-phenyl, 2-CF₃-phenyl, azetidin-1-yl, pyrrol-1-yl, imidazol-1-yl, morpholin-1-yl, pyrid-3-yl, pyrid-4-yl, or 3-halo-pyrid-4-yl;
R³, R⁴, R⁵ and R⁶, at each occurrence, are independently selected from H, halogen, C₁₋₄ alkyl, C₁₋₄ alkoxy, or C₁₋₂ haloalkyl;
R⁷ is independently selected from —CH₂C(C₁₋₂ alkyl)₂OH, —CH₂CH₂SO(C₁₋₂ alkyl), —CH₂CH₂SO₂(C₁₋₂ alkyl), —CH₂CH(OH)CH₂SO₂(C₁₋₂ alkyl), or

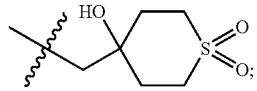

and
R⁸ is independently selected from C₁₋₄ alkyl, C₁₋₄ alkoxy or —OCH₂CH₂F.

8. A compound according to claim 7, wherein:
R¹ is independently at selected from the group consisting of H and Me;
R², at each occurrence, is independently selected from OMe, Cl, I, CF₃, CH₂CF₃, OCF₃, cyclopropyl, cyclopropyloxy, phenyl, 2-Me-phenyl, 2-F-phenyl, 3-F-phenyl, 4-F-phenyl, 2-Cl-phenyl, azetidin-1-yl, pyrrol-1-yl, pyrid-3-yl, or pyrid-4-yl;
R³, R⁴, R⁵ and R⁶, at each occurrence, are independently selected from H, F, Cl, Me, OMe, CF₃, or OCF₃;
R⁷ is independently selected from —CH₂C(Me)₂OH, —CH₂CH₂SO₂Me, —CH₂CH₂SOMe, —CH₂CH(OH)CH₂SO₂Me, —CH₂CH(OH)CH₂SO₂Et, or

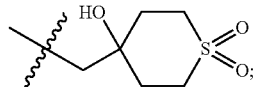 [SMILES: *CC1(O)CCS(=O)(=O)CC1]

and
R⁸ is independently selected from Me, OMe or —OCH₂CH₂F.

9. A compound according to claim 1, wherein the compound is selected from the group consisting of

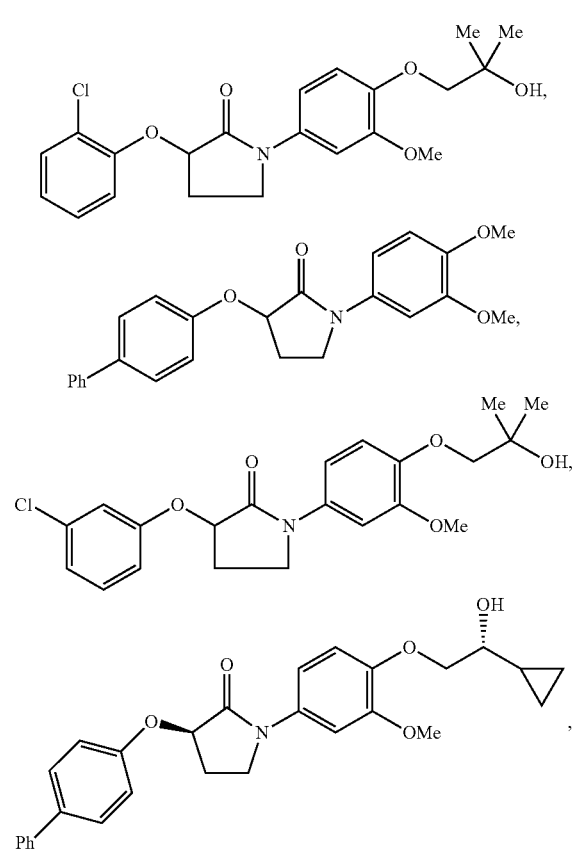

-continued
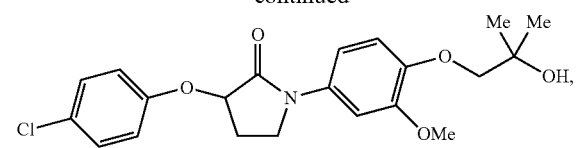
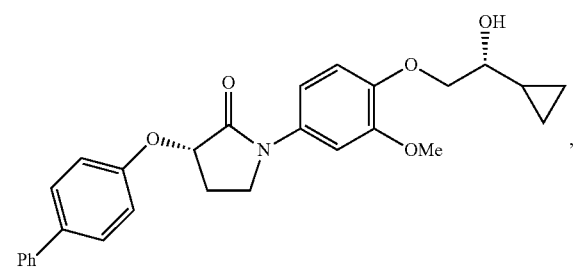
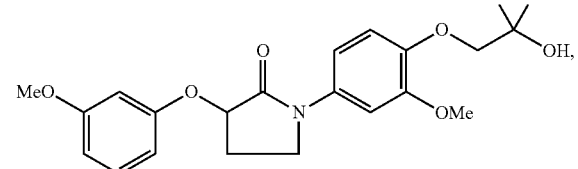
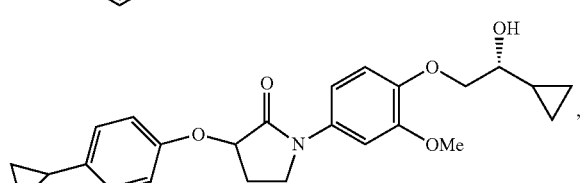
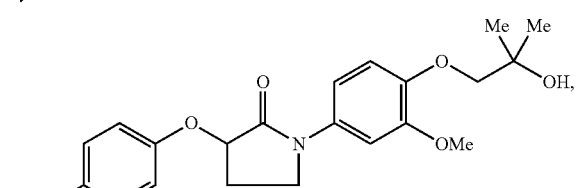
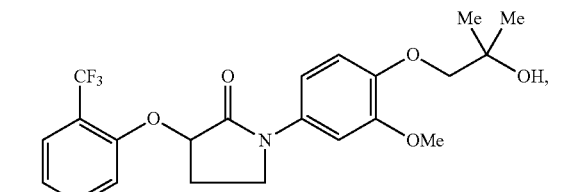
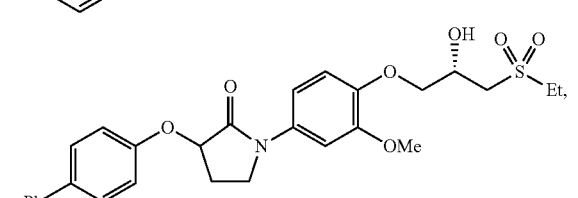
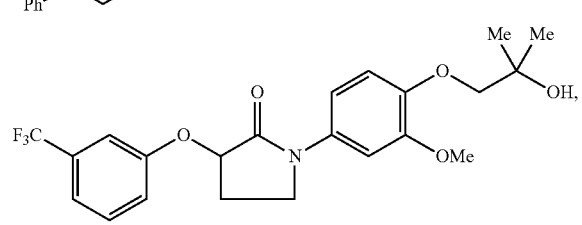
-continued
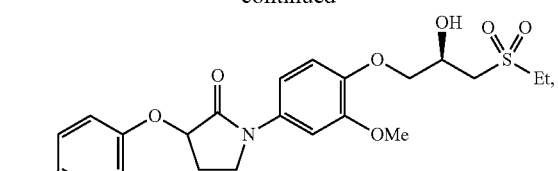
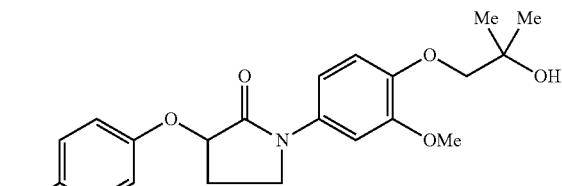
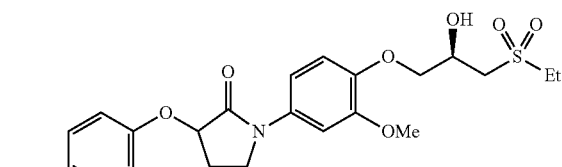
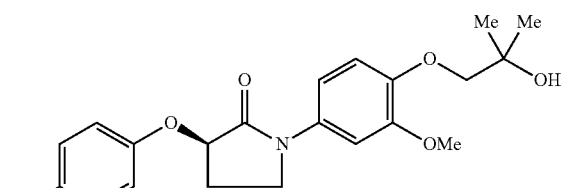
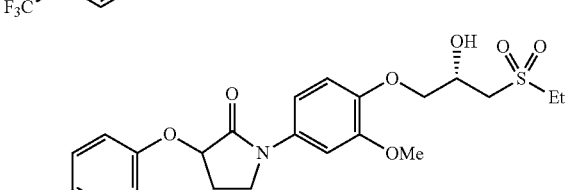
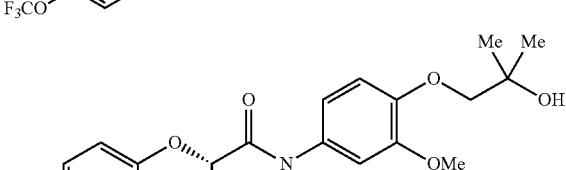
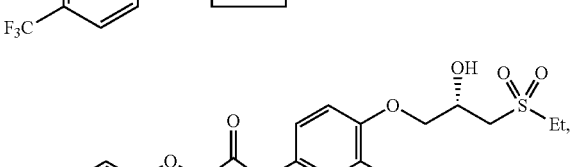
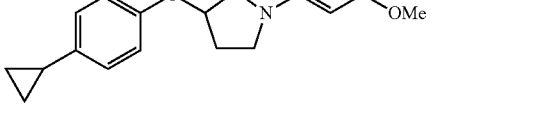
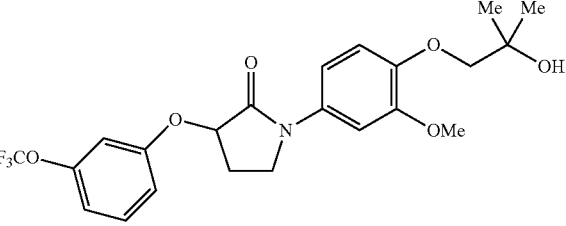

-continued
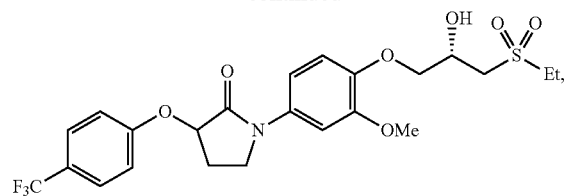
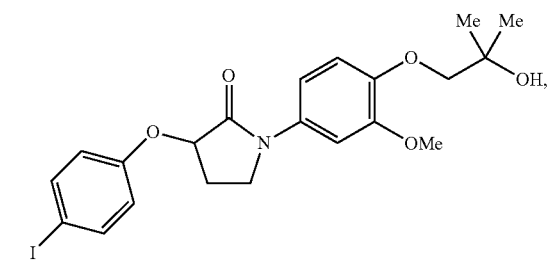
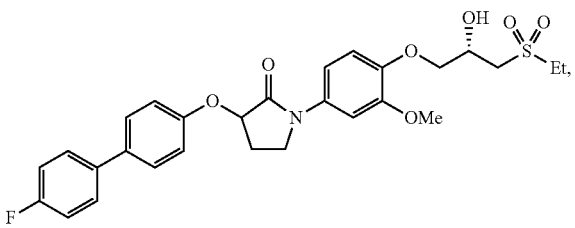
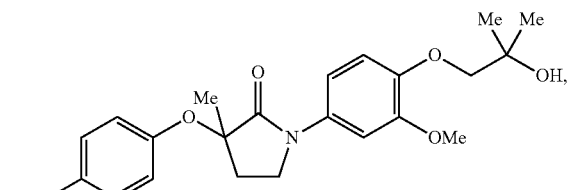
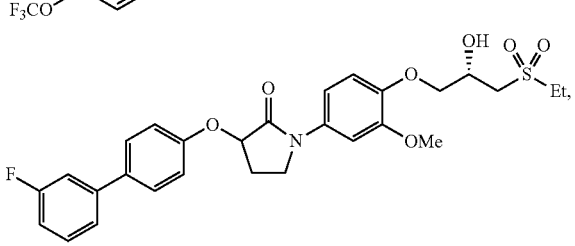
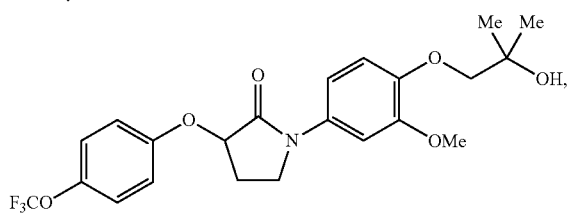
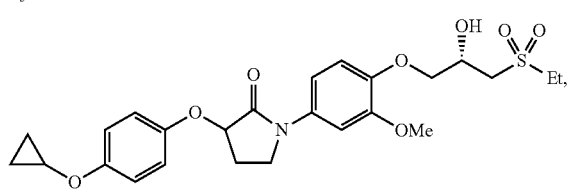
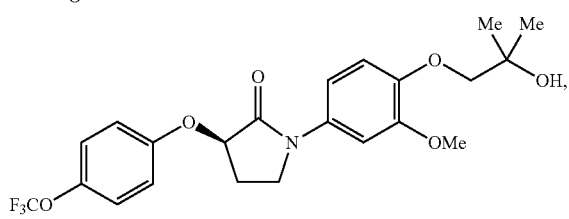
-continued
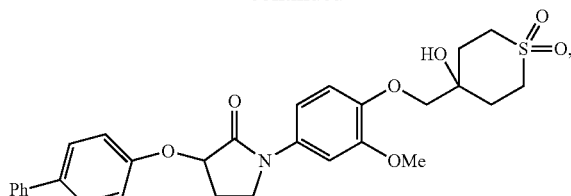
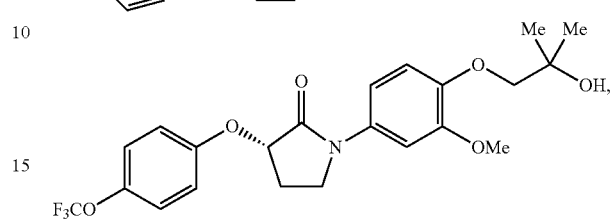
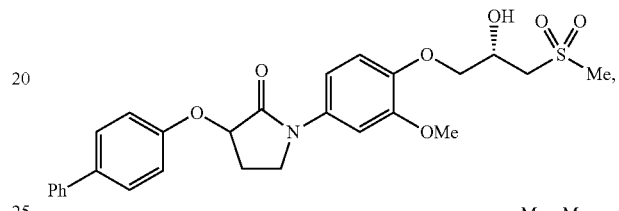
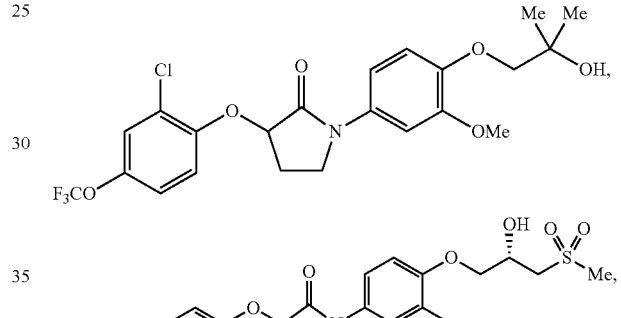
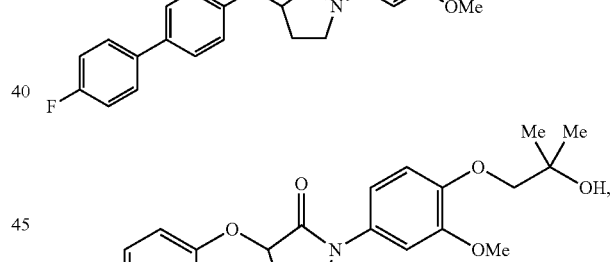
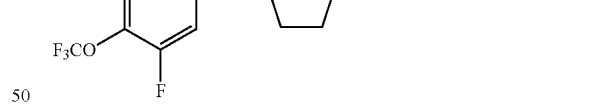
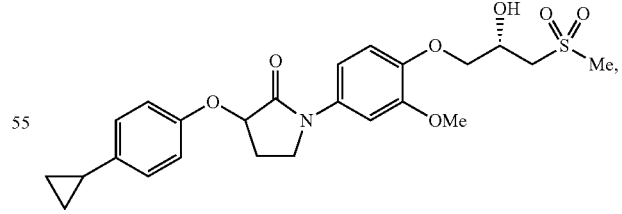
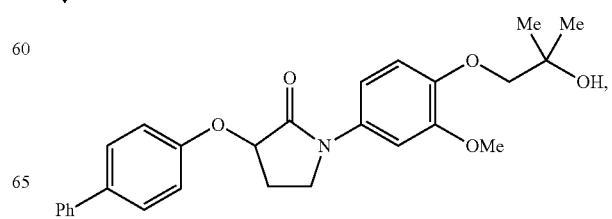

149
-continued
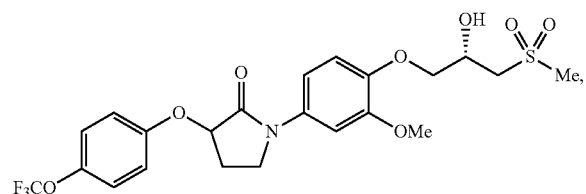
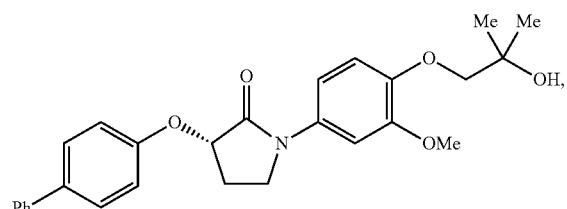
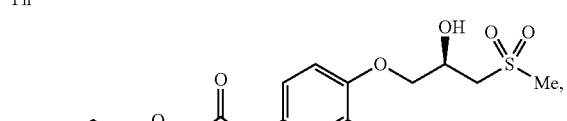
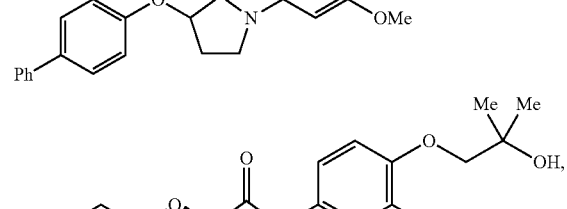
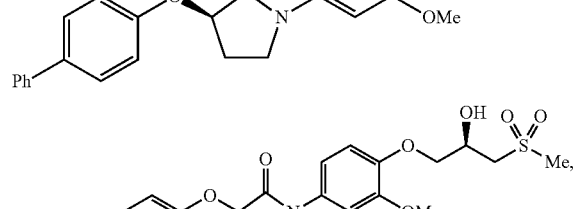
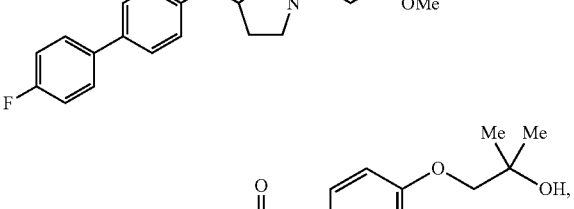
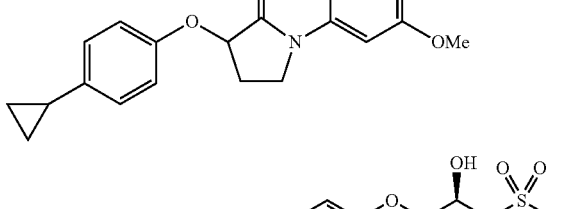
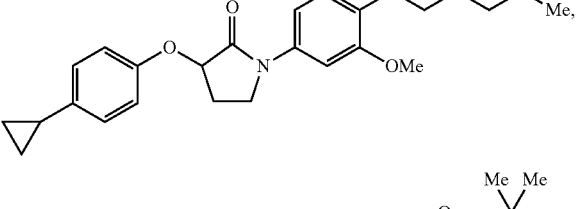
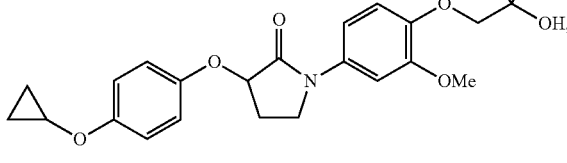
150
-continued
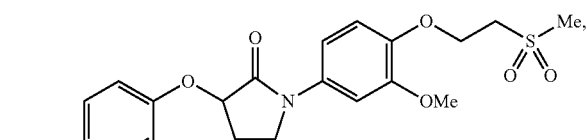
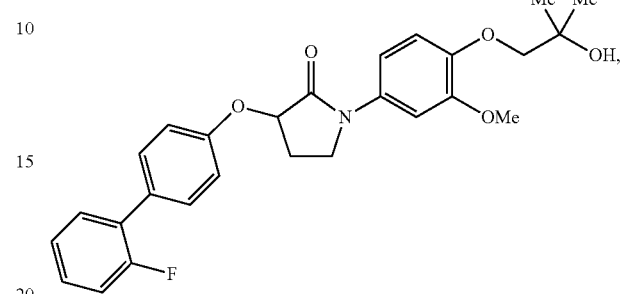
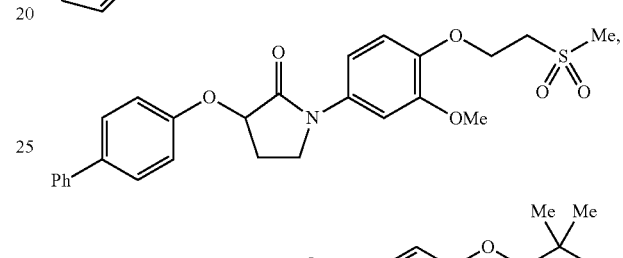
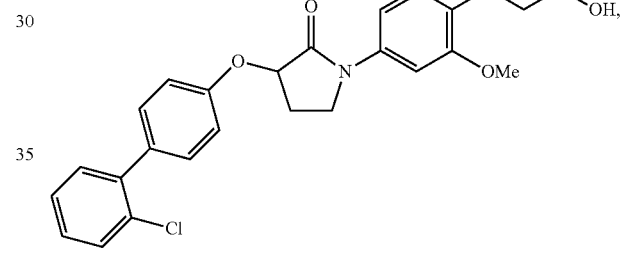
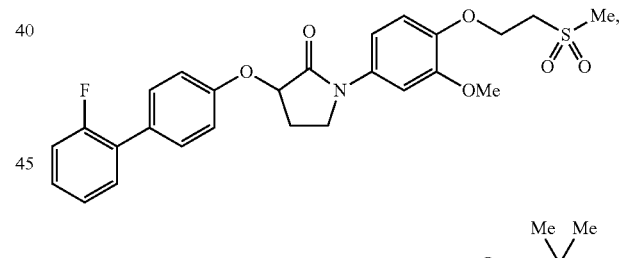
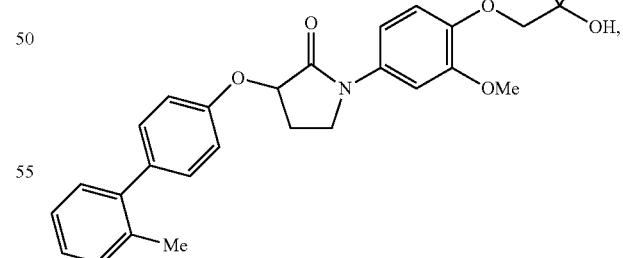
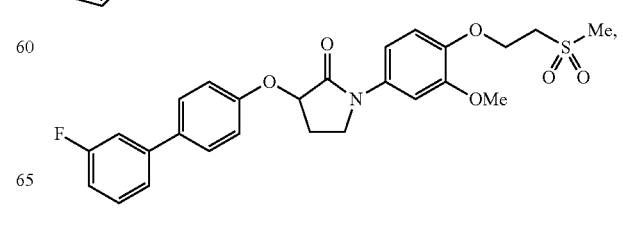

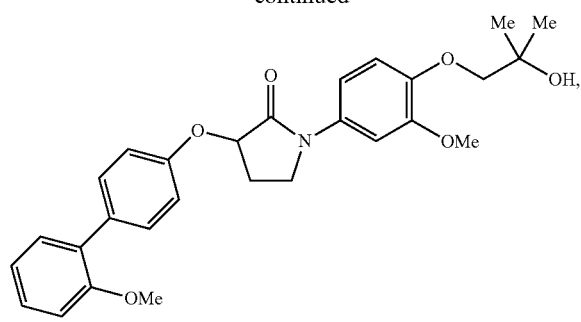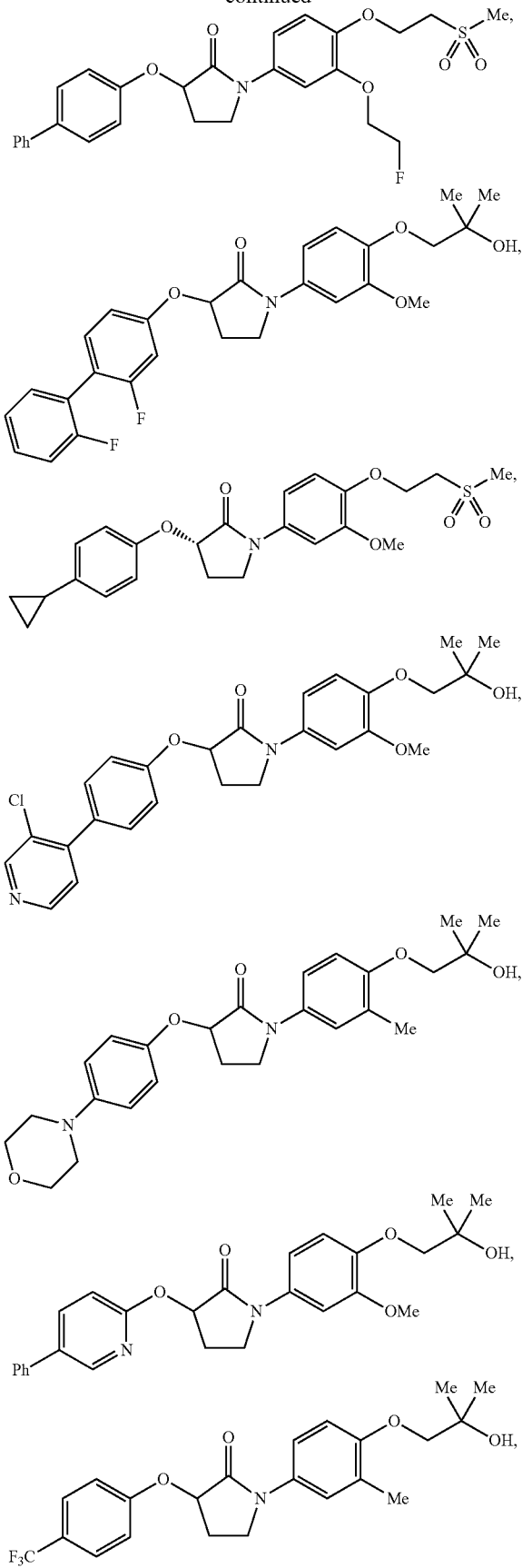

153
-continued
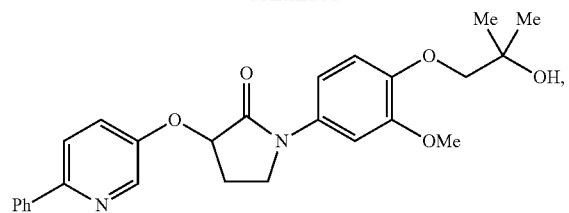
154
-continued
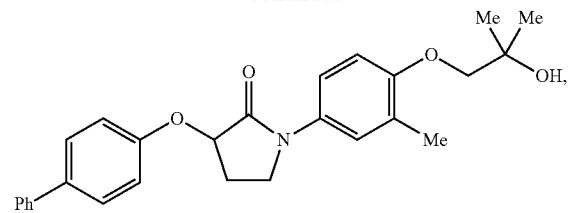

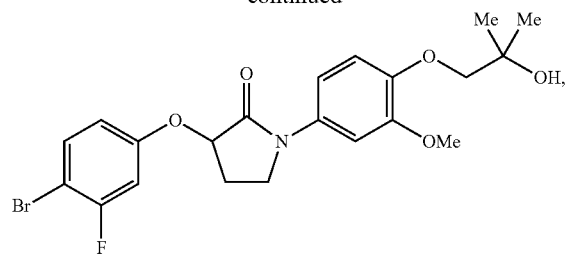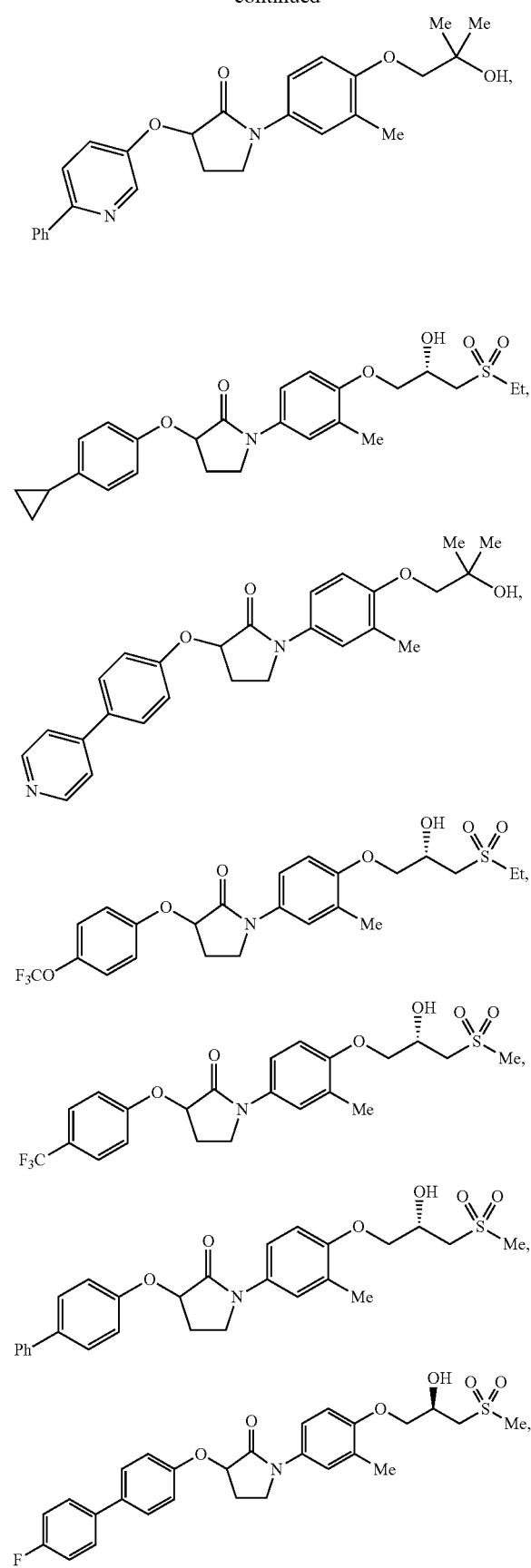

157
-continued
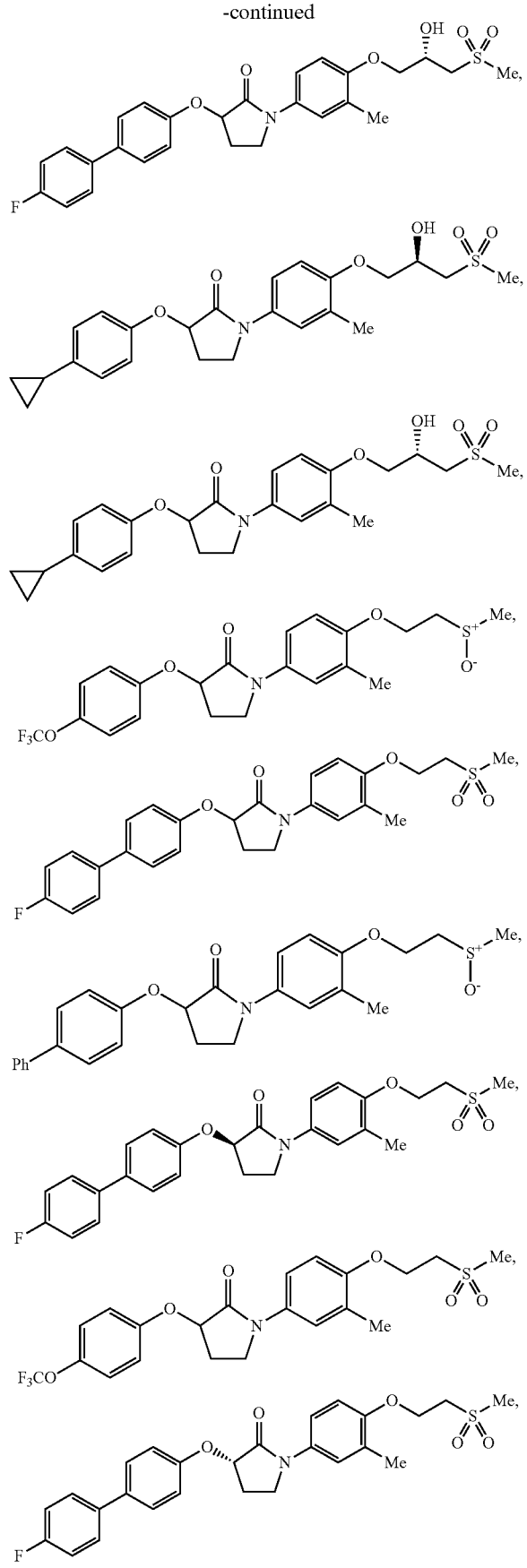
158
-continued
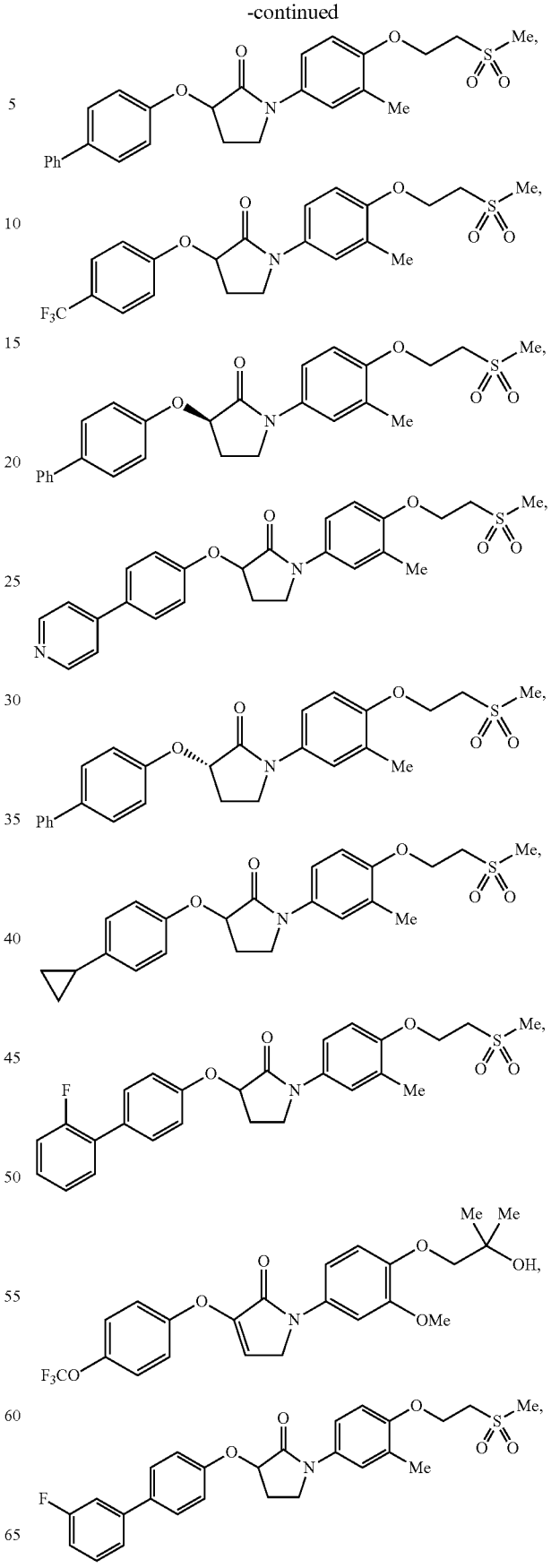

159
-continued
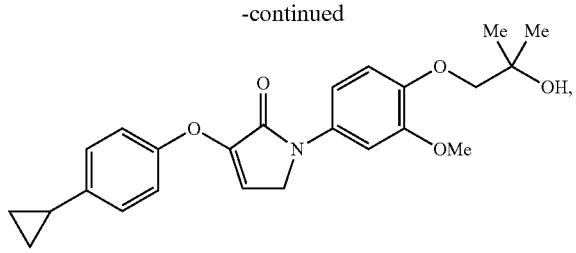
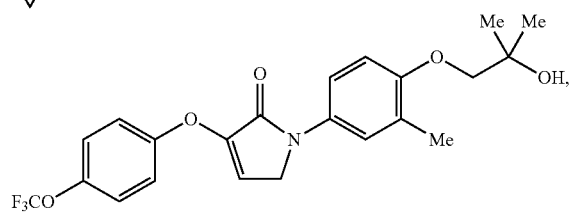
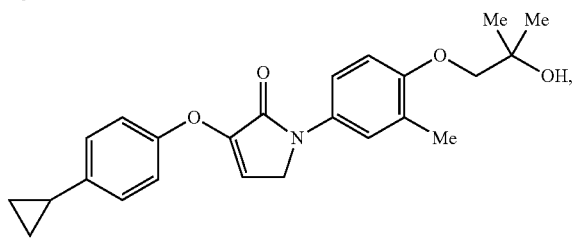
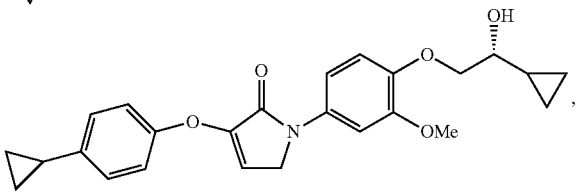
160
-continued
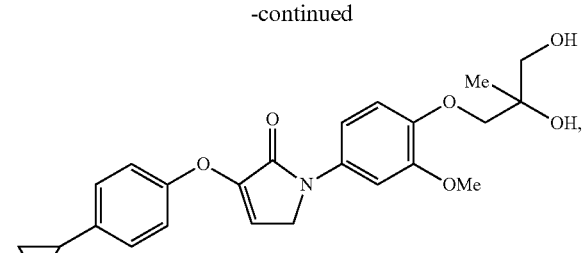
and
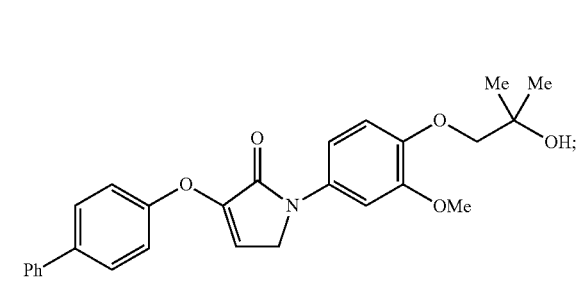
or a stereoisomer, a tautomer, or a pharmaceutically acceptable salt thereof.
10. A pharmaceutical composition, comprising a pharmaceutically acceptable carrier and a compound of claim 1.
* * * * *

UNITED STATES PATENT AND TRADEMARK OFFICE
CERTIFICATE OF CORRECTION

PATENT NO.       : 9,586,900 B2  
APPLICATION NO.  : 14/425507  
DATED            : March 7, 2017  
INVENTOR(S)      : Saleem Ahmad et al.

Page 1 of 1

It is certified that error appears in the above-identified patent and that said Letters Patent is hereby corrected as shown below:

In the Claims

Claim 1, Column 141, Line 26, after "carbon" delete "37".

Claim 1, Column 141, Line 30, delete "alkoxy; halogen," and insert -- alkoxy, --, therefor.

Claim 1, Column 141, Line 40, after "$OR^d$," insert -- $C_{1-4}$ alkyl, --.

Claim 1, Column 141, Line 43, after "halogen," delete "OH, CN,".

Claim 1, Column 141, Line 67, after "$R^a$," insert -- or --.

Claim 3, Column 142, Line 42 (Approx.), after "alkyl)," insert -- or --.

Claim 4, Column 143, Line 43, delete "alkyl) (CH$_2$OH)OH" and insert -- alkyl)(CH$_2$OH)OH; --, therefor.

Signed and Sealed this  
Twenty-third Day of January, 2018

Joseph Matal  
*Performing the Functions and Duties of the*  
*Under Secretary of Commerce for Intellectual Property and*  
*Director of the United States Patent and Trademark Office*